United States Patent
Lee et al.

(10) Patent No.: US 12,410,261 B2
(45) Date of Patent: *Sep. 9, 2025

(54) ANTI-HER2 ANTIBODY OR ANTIGEN-BINDING FRAGMENT THEREOF, AND CHIMERIC ANTIGEN RECEPTOR COMPRISING SAME

(71) Applicant: GC Cell Corporation, Yongin-si (KR)

(72) Inventors: Jong Seo Lee, Yongin-si (KR); Kyu Tae Kim, Yongin-si (KR); Young Ha Lee, Yongin-si (KR); In Sik Hwang, Yongin-si (KR); Bong Kook Ko, Yongin-si (KR); Eunji Choi, Yongin-si (KR); You-Sun Kim, Yongin-si (KR); Jeongmin Kim, Yongin-si (KR); Miyoung Jung, Yongin-si (KR); Hoyong Lim, Yongin-si (KR); Sungyoo Cho, Yongin-si (KR)

(73) Assignee: GC Cell Corporation, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/618,414

(22) Filed: Mar. 27, 2024

(65) Prior Publication Data

US 2024/0270872 A1 Aug. 15, 2024

Related U.S. Application Data

(60) Continuation of application No. 18/298,310, filed on Apr. 10, 2023, now Pat. No. 11,970,547, which is a division of application No. 16/881,650, filed on May 22, 2020, now Pat. No. 11,649,294, which is a continuation-in-part of application No. 16/764,276, filed as application No. PCT/KR2018/013928 on Nov. 14, 2018, now Pat. No. 12,116,417.

(30) Foreign Application Priority Data

Nov. 14, 2017 (KR) .......................... 10-2017-0151841

(51) Int. Cl.
| | |
|---|---|
| *C07K 16/32* | (2006.01) |
| *A61K 38/17* | (2006.01) |
| *A61K 40/15* | (2025.01) |
| *A61K 40/31* | (2025.01) |
| *A61K 40/42* | (2025.01) |
| *A61P 35/00* | (2006.01) |
| *C07K 14/705* | (2006.01) |
| *C12N 5/0783* | (2010.01) |

(52) U.S. Cl.
CPC ............ *C07K 16/32* (2013.01); *A61K 38/177* (2013.01); *A61K 40/15* (2025.01); *A61K 40/31* (2025.01); *A61K 40/4205* (2025.01); *A61P 35/00* (2018.01); *C07K 14/705* (2013.01); *C12N 5/0646* (2013.01); *A61K 2239/31* (2023.05); *A61K 2239/38* (2023.05); *A61K 2239/49* (2023.05); *A61K 2239/53* (2023.05); *C07K 2317/565* (2013.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 5,783,186 A | 7/1998 | Arakawa et al. |
| 5,821,337 A | 10/1998 | Carter et al. |
| 7,674,460 B2 | 3/2010 | Serrero |
| 7,741,465 B1 | 6/2010 | Eshhar et al. |
| 8,314,213 B2 | 11/2012 | Bernett et al. |
| 8,404,811 B2 | 3/2013 | Ye et al. |
| 9,079,976 B2 | 7/2015 | Shirwan et al. |
| 9,394,368 B2 | 7/2016 | Brogdon et al. |
| 9,624,276 B2 | 4/2017 | Young et al. |
| 9,777,064 B2 | 10/2017 | Wang et al. |
| 9,845,362 B2 | 12/2017 | Mukherjee |
| 10,124,023 B2 | 11/2018 | Brentjens et al. |
| 10,174,116 B2 | 1/2019 | Lee et al. |
| 10,273,280 B2 | 4/2019 | Ma et al. |
| 10,736,918 B2 | 8/2020 | Jensen et al. |
| 11,091,532 B2 | 8/2021 | Puléet al. |

(Continued)

FOREIGN PATENT DOCUMENTS

| | | |
|---|---|---|
| CA | 2402930 | 3/2004 |
| CN | 104177499 | 12/2014 |

(Continued)

OTHER PUBLICATIONS

Qin et al. (Incorporation of a hinge domain improves the expansion of chimeric antigen receptor T cells. J Hematol Oncol 10, 68, Mar. 2017). (Year: 2017).*

(Continued)

*Primary Examiner* — Zachariah Lucas
*Assistant Examiner* — Sarah A Alsomairy
(74) *Attorney, Agent, or Firm* — Fish & Richardson P.C.

(57) ABSTRACT

The present disclosure relates to a novel anti-HER2 antibody or an antigen-binding fragment thereof used in the prevention or treatment of cancer, a chimeric antigen receptor including the same, and uses thereof. The antibody of the present disclosure is an antibody that specifically binds to HER2 which is highly expressed in cancer cells (particularly, breast cancer or gastric cancer cells), and binds to an epitope that is different from an epitope to which trastuzumab binds.

20 Claims, 26 Drawing Sheets

Specification includes a Sequence Listing.

(56) References Cited

U.S. PATENT DOCUMENTS

| | | | |
|---|---|---|---|
| 11,197,919 B2 * | 12/2021 | Priceman | A61K 39/464406 |
| 11,649,294 B2 | 5/2023 | Lee et al. | |
| 11,970,547 B2 | 4/2024 | Lee et al. | |
| 12,116,417 B2 | 10/2024 | Lee et al. | |
| 2004/0043401 A1 | 3/2004 | Sadelain et al. | |
| 2009/0285837 A1 | 11/2009 | Kao et al. | |
| 2010/0183604 A1 | 7/2010 | Ohta et al. | |
| 2014/0199334 A1 | 7/2014 | Sasikumar et al. | |
| 2014/0255363 A1 | 9/2014 | Metelitsa et al. | |
| 2014/0294898 A1 | 10/2014 | Miller et al. | |
| 2014/0322275 A1 | 10/2014 | Brogdon et al. | |
| 2015/0125491 A1 | 5/2015 | Sasikumar et al. | |
| 2016/0130357 A1 | 5/2016 | Mukherjee | |
| 2016/0158285 A1 | 6/2016 | Cooper et al. | |
| 2016/0340391 A1 | 11/2016 | Miller et al. | |
| 2016/0340406 A1 | 11/2016 | Zhao et al. | |
| 2017/0051068 A1 | 2/2017 | Pillarisetti et al. | |
| 2017/0107216 A1 | 4/2017 | Wu et al. | |
| 2017/0151281 A1 | 6/2017 | Wagner et al. | |
| 2017/0174679 A1 | 6/2017 | Lajkiewicz et al. | |
| 2017/0190786 A1 | 7/2017 | Fendly et al. | |
| 2017/0252432 A1 | 9/2017 | Allen et al. | |
| 2017/0313759 A1 | 11/2017 | Batuwangala | |
| 2017/0335281 A1 | 11/2017 | Loew et al. | |
| 2017/0362253 A1 | 12/2017 | Xiao et al. | |
| 2018/0057486 A1 | 3/2018 | Wu et al. | |
| 2018/0079824 A1 | 3/2018 | Ahmed et al. | |
| 2018/0326032 A1 | 11/2018 | Priceman et al. | |
| 2019/0037831 A1 | 2/2019 | Hwang et al. | |
| 2019/0336533 A1 | 11/2019 | Hwang et al. | |
| 2020/0038441 A1 | 2/2020 | Klingemann et al. | |
| 2020/0102366 A1 | 4/2020 | Cooper et al. | |
| 2020/0108096 A1 | 4/2020 | Min et al. | |
| 2020/0399397 A1 | 12/2020 | Lee et al. | |
| 2021/0008105 A1 | 1/2021 | Martin | |
| 2021/0040216 A1 | 2/2021 | Chui et al. | |
| 2021/0060070 A1 | 3/2021 | Coughlin | |
| 2021/0147803 A1 | 5/2021 | Hwang et al. | |
| 2021/0179733 A1 | 6/2021 | Lee et al. | |
| 2022/0133663 A1 | 5/2022 | Splichal | |
| 2023/0025506 A1 | 1/2023 | Hwang et al. | |
| 2023/0303716 A1 | 9/2023 | Lee et al. | |
| 2024/0366663 A1 | 11/2024 | Kim et al. | |
| 2024/0409665 A1 | 12/2024 | Lee et al. | |
| 2025/0073264 A1 | 3/2025 | Lim et al. | |

FOREIGN PATENT DOCUMENTS

| | | |
|---|---|---|
| CN | 105246504 | 1/2016 |
| CN | 105925536 | 9/2016 |
| EP | 3567049 A2 | 11/2019 |
| JP | 2010006705 | 1/2010 |
| JP | 2013534809 | 9/2013 |
| JP | 2016508725 | 3/2016 |
| JP | 2016518368 | 6/2016 |
| KR | 10-1453462 | 10/2014 |
| KR | 10-2015-0048783 | 5/2015 |
| KR | 10-2016-0015195 | 2/2016 |
| KR | 10-2016-0022857 | 3/2016 |
| KR | 10-2016-0062760 | 6/2016 |
| WO | WO 1994/000136 | 1/1994 |
| WO | WO 2006/033700 | 9/2006 |
| WO | WO 2011/127297 | 10/2011 |
| WO | WO 2013/094988 | 6/2013 |
| WO | WO 2014/130657 | 8/2014 |
| WO | WO 2014/185704 | 11/2014 |
| WO | WO 2015/033299 | 3/2015 |
| WO | WO 2015/033301 | 3/2015 |
| WO | WO 2015/033303 | 3/2015 |
| WO | WO 2015/034820 | 3/2015 |
| WO | WO 2015/036927 | 3/2015 |
| WO | WO 2015/044900 | 4/2015 |
| WO | WO 2015/095895 | 6/2015 |
| WO | WO 2015/160641 | 10/2015 |
| WO | WO 2015/164594 | 10/2015 |
| WO | WO 2016/039749 | 3/2016 |
| WO | WO 2016/176639 | 3/2016 |
| WO | WO 2016/077518 | 5/2016 |
| WO | WO 2016/085248 | 6/2016 |
| WO | WO 2016/090320 | 6/2016 |
| WO | WO 2016/100608 | 6/2016 |
| WO | WO 2016/120219 | 8/2016 |
| WO | WO 2016/123333 | 8/2016 |
| WO | WO 2016/126646 | 8/2016 |
| WO | WO 2016/142833 | 9/2016 |
| WO | WO 2016/142835 | 9/2016 |
| WO | WO 2016/142852 | 9/2016 |
| WO | WO 2016/142886 | 9/2016 |
| WO | WO 2016/142894 | 9/2016 |
| WO | WO 2016/154585 | 9/2016 |
| WO | WO 2016/174652 | 11/2016 |
| WO | WO 2016/191756 | 12/2016 |
| WO | WO 2017/066227 | 4/2017 |
| WO | WO 2017/070089 | 4/2017 |
| WO | WO 2017/079694 | 5/2017 |
| WO | WO 2017/079705 | 5/2017 |
| WO | WO 2017/106634 | 6/2017 |
| WO | WO 2017/118762 | 7/2017 |
| WO | WO 2017/167967 | 10/2017 |
| WO | WO 2017/176608 | 10/2017 |
| WO | WO 2017/192961 | 11/2017 |
| WO | WO 2017/202273 | 11/2017 |
| WO | WO 2017/202275 | 11/2017 |
| WO | WO 2017/202276 | 11/2017 |
| WO | WO 2017/205464 | 11/2017 |
| WO | WO 2017/222593 | 12/2017 |
| WO | WO 2018/005374 | 1/2018 |
| WO | WO 2018/006795 | 1/2018 |
| WO | WO 2018/009505 | 1/2018 |
| WO | WO 2018/013789 | 1/2018 |
| WO | WO 2018/026971 | 2/2018 |
| WO | WO 2018/044963 | 3/2018 |
| WO | WO 2018/045142 | 3/2018 |
| WO | WO 2018/051254 | 3/2018 |
| WO | WO 2018/051255 | 3/2018 |
| WO | WO 2018/140725 | 8/2018 |
| WO | WO 2019/008152 | 1/2019 |
| WO | WO 2019/008154 | 1/2019 |
| WO | WO 2019/023575 | 1/2019 |
| WO | WO 2019/030757 | 2/2019 |
| WO | WO 2019/079564 | 4/2019 |
| WO | WO 2019/098682 | 5/2019 |
| WO | WO 2019/160501 | 8/2019 |
| WO | WO 2019/160956 | 8/2019 |
| WO | WO 2019/182392 | 9/2019 |
| WO | WO 2020/055040 | 3/2020 |
| WO | WO 2020/069409 | 4/2020 |
| WO | WO 2020/096646 | 5/2020 |
| WO | WO 2020/097346 A1 | 5/2020 |
| WO | WO 2020/101361 | 5/2020 |
| WO | WO 2021/071962 | 4/2021 |
| WO | WO 2021/218947 | 11/2021 |
| WO | WO 2022/133056 | 6/2022 |
| WO | WO 2022/133057 | 6/2022 |
| WO | WO 2022/133061 | 6/2022 |
| WO | WO 2022/204244 | 9/2022 |
| WO | WO 2022/216144 | 10/2022 |
| WO | WO 2022/216811 | 10/2022 |
| WO | WO 2022/216813 | 10/2022 |
| WO | WO 2022/216815 | 10/2022 |
| WO | WO 2022/216826 | 10/2022 |
| WO | WO 2022/216831 | 10/2022 |
| WO | WO 2022/216837 | 10/2022 |
| WO | WO 2023/080895 | 5/2023 |
| WO | WO 2023/081317 | 5/2023 |
| WO | WO 2024/040135 | 2/2024 |
| WO | WO 2024/119126 | 6/2024 |
| WO | WO 2024/238582 A2 | 11/2024 |
| WO | WO 2024/243058 A1 | 11/2024 |
| WO | WO 2024/254507 A2 | 12/2024 |
| WO | WO 2024/259070 A2 | 12/2024 |

(56) References Cited

OTHER PUBLICATIONS

Sun et al. (Construction and evaluation of a novel humanized HER2-specific chimeric receptor. Breast Cancer Res 16, R61, 2014) (Year: 2014).*
U.S. Appl. No. 16/474,426, filed Jun. 27, 2019, Hwang et al.
U.S. Appl. No. 16/764,276, filed Sep. 28, 2020, Lee et al.
U.S. Appl. No. 16/881,650, filed May 22, 2020, Lee et al.
U.S. Appl. No. 17/845,793, filed Jun. 21, 2022, Hwang et al.
U.S. Appl. No. 18/285,631, filed Oct. 4, 2023, Hwang et al.
U.S. Appl. No. 18/285,634, filed Oct. 4, 2023, Kim et al.
U.S. Appl. No. 18/285,636, filed Oct. 4, 2023, Lim et al.
U.S. Appl. No. 18/298,310, filed Apr. 10, 2023, Lee et al.
Abate-Daga et al., "CAR models: next-generation CAR modifications for enhanced T-cell function," Molecular Therapy—Oncolytics, Jan. 2016, 3(16014):1-7.
Abou-Alfa et al., "Randomized phase II placebo controlled study of codrituzumab in previously treated patients with advanced hepatocellular carcinoma," J. Hepatol., Aug. 2016, 65(2):289-95.
Agus et al., "Phase I clinical study of pertuzumab, a novel HER dimerization inhibitor, in patients with advanced cancer," J. Clin. Oncol., Apr. 10, 2005, 23(11):2534-43.
Akiyama et al., "The product of the human c-erbB-2 gene: a 185-kilodalton glycoprotein with tyrosine kinase activity," Science, Jun. 27, 1986, 232(4758):1644- 1646.
Alizadeh et al., "IL15 Enhances CAR-T Cell Antitumor Activity by Reducing mTORC1 Activity and Preserving Their Stem Cell Memory Phenotype," Cancer Immunology Research, May 2019, 7(5):759-772.
Altschul et al., "Basic local alignment search tool," J. Mol. Biol., Oct. 5, 1990, 215(3):403-410.
Andre et al., "Anti-NKG2A mAb Is a Checkpoint Inhibitor that Promotes Anti-tumor Immunity by Unleashing Both T and NK Cells," Cell. Dec. 13, 2018;175(7):1731-1743.
Arteaga et al., "p185c-erbB-2 Signaling Enhances Cisplatin-induced Cytotoxicity in Human Breast Carcinoma Cells: Association between an Oncogenic Receptor Tyrosine Kinase and Drug-induced DNA Repair," Cancer Research, Jul. 1994, 54:3758-3765.
Ataca et al., "Chimeric Antigen Receptor T Cell Therapy in Hematology," Turk J Hematol., 2015, 32:285-294.
Awada et al., "Abstract No. 2504: Results from a first-in-man, open label, safety and tolerability trial of CAN04 (nidanilimab), a fully humanized monoclonal antibody against the novel antitumor target, IL1RAP, in patients with solid tumors," Presented at ASCO 2019, Chicago, Illinois, May 31-Jun. 4, 2019, 14 pages.
Babic et al., "Pritumumab, the first therapeutic antibody for glioma patients," Hum Antibodies, Feb. 5, 2018, 26(2):95-101.
Bacigalupo et al., "Treatment of steroid resistant acute graft versus host disease with an anti-CD26 monoclonal antibody—Begelomab," Bone Marrow Transplant, Aug. 2020, 55(8):1580-1587.
Bacus et al., "Differentiation of cultured human breast cancer cells (AU-565 and MCF-7) associated with loss of cell surface HER-2/neu antigen," Molecular Carcinogenesis, 1990, 3:350-362.
Bacus et al., "Tumor-inhibitory Monoclonal Antibodies to the HER-2/Neu Receptor Induce Differentiation of Human Breast Cancer Cells," Cancer Research, May 1992, 52:2580-2589.
Bajaj et al., "Conatumumab: a novel monoclonal antibody against death receptor 5 for the treatment of advanced malignancies in adults," Expert Opin. Biol. Ther., Nov. 2011, 11(11): 1519-1524.
Baldo et al., "Amatuximab and novel agents targeting mesothelin for solid tumors," Onco Targets Ther., Nov. 2017, 10:5337-5353.
Bang et al., "First-in-human phase 1 study of margetuximab (MGAH22), an Fc-modified chimeric monoclonal antibody, in patients with HER2-positive advanced solid tumors," Ann. Oncol., Apr. 2017, 28(4):855-861.
Bauman et al., "Phase I Study of Ficlatuzumab and Cetuximab in Cetuximab-Resistant, Recurrent/Metastatic Head and Neck Cancer.," Cancers, Jun. 11, 2020, 12(6):1537.

Bhati et al., "Efficacy and safety of an anti-CD 20 monoclonal antibody (Reditux™M) for the treatment of patients with moderate to severe rheumatoid arthritis following the failure of conventional synthetic disease-modifying anti-rheumatic drugs," Clin. Rheumatol., Aug. 2016, 35(8):1931-1935.
Bilen et al. "Association of Neutrophil-to-Lymphocyte Ratio with Efficacy of First-Line Avelumab plus Axitinib vs. Sunitinib in Patients with Advanced Renal Cell Carcinoma Enrolled in the Phase 3 JAVELIN Renal 101 Trial," Clin Cancer Res., Feb. 15, 2022, 28(4):738-747.
Bilusic et al., "Phase I trial of HuMax-IL8 (BMS-986253), an anti-IL-8 monoclonal antibody, in patients with metastatic or unresectable solid tumors," J. Immunother. Cancer, Sep. 5, 2019, 7(1):240.
Bobkov et al., "Antibodies targeting chemokine receptors CXCR4 and ACKR3," Mol. Pharmacol., Dec. 2019, 96(6):753-764.
Brunker et al., "RG7386, a novel tetravalent FAP-DR5 antibody, effectively triggers FAP-dependent, avidity-driven DR5 hyperclustering and tumor cell apoptosis," Mol. Cancer Ther., May 2016, 15(5):946-57.
Burge et al., "Pharmacokinetic and pharmacodynamic properties of TRU-015, a CD20-directed small modular immunopharmaceutical protein therapeutic, in patients with rheumatoid arthritis: a Phase I, open-label, dose-escalation clinical study," Clin. Ther., Oct. 2008, 30(10):1806-1816.
Bussolati et al., "A modified Trastuzumab antibody for the immunohistochemical detection of HER-2 overexpression in breast cancer," British Journal of Cancer, Apr. 5, 2005, 92:1261-1267.
Carson et al., "A potential role for interleukin-15 in the regulation of human natural killer cell survival," The Journal of Clinical Investigation, Mar. 1, 1997, 99(5):937-943.
Casulo et al., "A phase I study of PRO131921, a novel anti-CD20 monoclonal antibody in patients with relapsed/refractory CD20+ indolent NHL: correlation between clinical responses and AUC pharmacokinetics," Clin. Immunol. , Sep. 2014, 154(1):37-46.
Catenacci et al., "Phase I escalation and expansion study of bemarituzumab (FPA144) in patients with advanced solid tumors and FGFR2b-selected gastroesophageal adenocarcinoma.," J. Clin. Oncol., Jul. 20, 2020, 38(21):2418-2426.
Cerutti et al., "Physicochemical and biological characterization of RTXM83, a new rituximab biosimilar," BioDrugs, Jun. 2019, 33(3):307-319.
Chamie et al., "Adjuvant weekly girentuximab following nephrectomy for high-risk renal cell carcinoma: the ARISER randomized clinical trial," JAMA Oncol., Jul. 2017, 3(7):913-920.
Chen et al., "IGF-1R as an anti-cancer target—trials and tribulations," Chinese Journal of Cancer, May 2013, 32(5):242-252.
Cheney et al., "Ocaratuzumab, an Fc-engineered antibody demonstrates enhanced antibody-dependent cell-mediated cytotoxicity in chronic lymphocytic leukemia," MAbs, May-Jun. 2014, 6(3):749-55.
Cheng et al., "Safety and efficacy of tigatuzumab plus sorafenib as first-line therapy in subjects with advanced hepatocellular carcinoma: a phase 2 randomized study," J. Hepatol., Oct. 2015, 63(4):896-904.
Cho et al., "Antitumor activity of MEDI3726 (ADCT-401), a pyrrolobenzodiazepine antibody-drug conjugate targeting PSMA, in preclinical models of prostate cancer," Mol Cancer Ther., Oct. 2018, 17(10):2176-2186.
Choi et al., "Phase I Trial: Cirmtuzumab Inhibits ROR1 Signaling and Stemness Signatures in Patients with Chronic Lymphocytic Leukemia," Cell Stem Cell, Jun. 2018, 22(6):951-959.
ClinicalTrials.gov [online], "64Cu-TLX592 Phase I Safety, PK, Biodistribution and Dosimetry Study (CUPID Study) (CUPID)," NCT04726033, Nov. 28, 2022, retrieved on Feb. 20, 2024, retrieved from URL: <https://clinicaltrials.gov/study/NCT04726033>, 26 pages.
ClinicalTrials.gov [online], "A Dose Escalation Study of Glofitamab (RO7082859) as a Single Agent and in Combination With Obinutuzumab After a Fixed, Single Pre-Treatment Dose of Obinutuzumab in Participants With Relapsed/Refractory B-Cell Non-Hodgkin's Lymphoma," NCT03075696, Jan. 30, 2024, retrieved on Feb. 16, 2024, retrieved from URL: <https://clinicaltrials.gov/study/NCT03075696>, 41 pages.

(56) References Cited

OTHER PUBLICATIONS

ClinicalTrials.gov [online], "A Double-blind, Randomized Controlled Study in CD20-positive Diffuse B Cell Non-Hodgkin's Lymphoma Subjects," NCT01205737, Oct. 22, 2013, retrieved on Feb. 16, 2024, retrieved from URL: <https://clinicaltrials.gov/study/NCT01205737>, 22 pages.

ClinicalTrials.gov [online], "A First-in-human Study of the Safety, Pharmacokinetics, Pharmacodynamics and Anti-tumor Activity of SAR439459 Monotherapy and Combination of SAR439459 and Cemiplimab in Patients With Advanced Solid Tumors," NCT03192345, May 12, 2022, retrieved on Feb. 16, 2024, retrieved from URL: <https://clinicaltrials.gov/study/NCT03192345>, 37 pages.

ClinicalTrials.gov [online], "A Phase 1 Study of the Clinical and Immunologic Effects of ALT-803 in Patients With Advanced Solid Tumors," NCT01946789, Apr. 17, 2019, retrieved on Feb. 16, 2024, retrieved from URL: <https://clinicaltrials.gov/study/NCT01946789>, 23 pages.

ClinicalTrials.gov [online], "A Phase I Dose-Escalation Study of IMGN388 in Patients With Solid Tumors," NCT00721669, Sep. 13, 2013, retrieved on Feb. 8, 2024, retrieved from URL: <https://clinicaltrials.gov/study/NCT00721669>, 21 pages.

ClinicalTrials.gov [online], "A Phase I Pilot Study Comparing 123I MIP 1072 Versus 111in Capromab Pendetide in Subjects With Metastatic Prostate Cancer," NCT00992745, Oct. 12, 2011, retrieved on Feb. 8, 2024, retrieved from URL: <https://clinicaltrials.gov/study/NCT00992745>, 23 pages.

ClinicalTrials.gov [online], "A Phase I Study of Intravenous CO-H01 in Patients With Refractory or Relapsed Follicular Lymphoma," NCT03221348, Jan. 24, 2018, retrieved on Feb. 16, 2024, retrieved from URL: <https://clinicaltrials.gov/study/NCT03221348>, 22 pages.

ClinicalTrials.gov [online], "A Phase I Study of Lintuzumab-Ac225 in Patients With Refractory Multiple Myeloma," NCT02998047, Mar. 8, 2022, retrieved on Feb. 16, 2024, retrieved from URL: <https://clinicaltrials.gov/study/NCT02998047>, 25 pages.

ClinicalTrials.gov [online], "A Randomized, Double-blind, Multi-center, Multi-national Trial to Evaluate the Efficacy, Safety, and Immunogenicity of SAIT101 Versus Rituximab as a First-line Immunotherapy Treatment in Patients With Low Tumor Burden Follicular Lymphoma (RAMO-2)," NCT02809053, Oct. 8, 2020, retrieved on Feb. 16, 2024, retrieved from URL: <https://clinicaltrials.gov/study/NCT02809053>, 68 pages.

ClinicalTrials.gov [online], "A Safety and Tolerability Study of NC318 in Subjects With Advanced or Metastatic Solid Tumors," NCT03665285, Dec. 26, 2023, retrieved on Feb. 16, 2024, retrieved from URL: <https://clinicaltrials.gov/study/NCT03665285>, 29 pages.

ClinicalTrials.gov [online], "A Study Comparing GB241 and Rituximab in Patients With B-cell Non-Hodgkin's Lymphoma," NCT03003039, Mar. 23, 2021, retrieved on Feb. 16, 2024, retrieved from URL: <https://clinicaltrials.gov/study/NCT03003039>, 20 pages.

ClinicalTrials.gov [online], "A Study Evaluating the Safety and Pharmacokinetics of DMUC4064A in Participants With Platinum-Resistant Ovarian Cancer or Unresectable Pancreatic Cancer," NCT02146313, Jun. 21, 2018, retrieved on Feb. 16, 2024, retrieved from URL: <https://clinicaltrials.gov/study/NCT02146313>, 26 pages.

ClinicalTrials.gov [online], "A Study in Participants With Diabetic Kidney Disease," NCT01113801, Sep. 17, 2019, retrieved on Feb. 8, 2024, retrieved from URL: <https://classic.clinicaltrials.gov/ct2/show/NCT01113801>, 54 pages.

ClinicalTrials.gov [online], "A Study of AK119 (Anti-CD73 Antibody), a Treatment for COVID-19, in Health Subjects," NCT04516564, Oct. 18, 2021, retrieved on Feb. 20, 2024, retrieved from URL: <https://clinicaltrials.gov/study/NCT04516564>, 21 pages.

ClinicalTrials.gov [online], "A Study of Anti-VEGFR2 AK109 in Subjects With Advanced Solid Tumors," NCT04547205, Feb. 23, 2023, retrieved on Feb. 20, 2024, retrieved from URL: <https://clinicaltrials.gov/study/NCT04547205>, 21 pages.

ClinicalTrials.gov [online], "A Study of Axatilimab at 3 Different Doses in Participants With Chronic Graft Versus Host Disease (cGVHD) (AGAVE-201)," NCT04710576, Aug. 21, 2023, retrieved on Feb. 20, 2024, retrieved from URL: <https://clinicaltrials.gov/study/NCT04710576>, 28 pages.

ClinicalTrials.gov [online], "A Study of BI-1206 in Combination With Pembrolizumab in Subjects With Advanced Solid Tumors (Keynote-A04)," NCT04219254, Nov. 24, 2023, retrieved on Feb. 20, 2024, retrieved from URL: <https://clinicaltrials.gov/study/NCT04219254>, 29 pages.

ClinicalTrials.gov [online], "A Study of HLX06, a Humanized Monoclonal Antibody Targeting Human Vascular Endothelial Growth Factor Receptor-2 in Patients With Advanced Solid Tumors," NCT03494231, Jul. 30, 2019, retrieved on Feb. 16, 2024, retrieved from URL: < https://clinicaltrials.gov/study/NCT03494231>, 23 pages.

ClinicalTrials.gov [online], "A Study of IGN002 for Refractory NHL," NCT02847949, Mar. 11, 2022, retrieved on Feb. 16, 2024, retrieved from URL: <https://clinicaltrials.gov/study/NCT02847949>, 21 pages.

ClinicalTrials.gov [online], "A Study of Imvotamab Monotherapy and in Combination in Subjects With Relapsed/Refractory Non-Hodgkin Lymphoma," NCT04082936, Nov. 15, 2023, retrieved on Feb. 20, 2024, retrieved from URL: <https://clinicaltrials.gov/study/NCT04082936>, 23 pages.

ClinicalTrials.gov [online], "A Study of JNJ-63898081 in Participants With Advanced Stage Solid Tumors," NCT03926013, Nov. 7, 2022, retrieved on Feb. 20, 2024, retrieved from URL: <https://clinicaltrials.gov/study/NCT03926013>, 23 pages.

ClinicalTrials.gov [online], "A Study of LY3076226 in Participants With Advanced or Metastatic Cancer," NCT02529553, Apr. 17, 2020, retrieved on Feb. 16, 2024, retrieved from URL: <https://clinicaltrials.gov/study/NCT02529553>, 40 pages.

ClinicalTrials.gov [online], "A Study of MIL62 in Treatment of CD20 Positive B-cell Lymphomas," NCT04103905, Jun. 16, 2021, retrieved on Feb. 20, 2024, retrieved from URL: <https://clinicaltrials.gov/study/NCT04103905>, 23 pages.

ClinicalTrials.gov [online], "A Study of MSB0254 Injection in Advanced Solid Tumors," NCT04381325, Apr. 5, 2023, retrieved on Feb. 20, 2024, retrieved from URL: <https://clinicaltrials.gov/study/NCT04381325>, 26 pages.

ClinicalTrials.gov [online], "A Study to Assess Safety and Efficacy of PRL3-Zumab in Patients With Solid Tumors," NCT04452955, Mar. 1, 2023, retrieved on Feb. 20, 2024, retrieved from URL: <https://clinicaltrials.gov/study/NCT04452955>, 26 pages.

ClinicalTrials.gov [online], "A Study to Assess the Anti-Tumor Activity and Safety of Odronextamab in Patients With B-cell Non-Hodgkin Lymphoma That Have Been Previously Treated (ELM-2)," NCT03888105, Apr. 20, 2023, retrieved on Feb. 16, 2024, retrieved from URL: <https://clinicaltrials.gov/study/NCT03888105>, 36 pages.

ClinicalTrials.gov [online], "A Study to Assess the Safety and Efficacy of ASP1650, a Monoclonal Antibody Targeting Claudin 6 (CLDN6), in Male Subjects With Incurable Platinum Refractory Germ Cell Tumors," NCT03760081, Dec. 2, 2021, retrieved on Feb. 16, 2024, retrieved from URL: <https://clinicaltrials.gov/study/NCT03760081>, 65 pages.

ClinicalTrials.gov [online], "A Study to Compare the Efficacy and Safety of JHL1101 Versus Rituximab in Patients With Previously Untreated Diffuse Large B- Cell Lymphoma (DLBCL)," NCT03670901, Jan. 9, 2020, retrieved on Feb. 16, 2024, retrieved from URL: <https://clinicaltrials.gov/study/NCT03670901>, 21 pages.

ClinicalTrials.gov [online], "A Study to Evaluate Escalating Doses of ASP1235 (AGS62P1) Given as Monotherapy in Subjects With Acute Myeloid Leukemia (AML)," NCT02864290, Oct. 29, 2021, retrieved on Feb. 16, 2024, retrieved from URL: <https://clinicaltrials.gov/study/NCT02864290>, 46 pages.

ClinicalTrials.gov [online], "A Study to Evaluate Safety, Tolerability and Prelimianry Efficacy of FP-1305 in Cancer Patients (MATINS)," NCT03733990, Nov. 27, 2023, retrieved on Feb. 16, 2024, retrieved from URL: <https://clinicaltrials.gov/study/NCT03733990>, 26 pages.

ClinicalTrials.gov [online], "An A/B Dose Escalation Study of AbGn-7 Alone and With FOLFOX7 Treatment in Patients With

(56) References Cited

OTHER PUBLICATIONS

Advanced Solid Tumors," NCT01466569, Jun. 23, 2015, retrieved on Feb. 16, 2024, retrieved from URL: <https://clinicaltrials.gov/study/NCT01466569>, 23 pages.
ClinicalTrials.gov [online], "An Active Treatment Study of SRK-015 in Patients With Type 2 or Type 3 Spinal Muscular Atrophy," NCT03921528, Apr. 12, 2023, retrieved on Feb. 20, 2024, retrieved from URL: <https://clinicaltrials.gov/study/NCT03921528>, 56 pages.
ClinicalTrials.gov [online], "An Open-Label Study of Intra-articular AMB-05X Injections in Subjects With Tenosynobial Giant Cell Tumor of the Knee," NCT04731675, Oct. 6, 2022, retrieved on Feb. 20, 2024, retrieved from URL: <https://clinicaltrials.gov/study/NCT04731675>, 24 pages.
ClinicalTrials.gov [online], "ARX517 as Monotherapy and in Combination Regimens in Subjects With Metastatic Castration-resistant Prostate Cancer (ARX517)," NCT04662580, Nov. 22, 2023, retrieved on Feb. 20, 2024, retrieved from URL: <https://clinicaltrials.gov/study/NCT04662580>, 27 pages.
ClinicalTrials.gov [online], "Assessment of the Safety and Efficacy of BG9924 in Rheumatoid Arthritis (RA) Participants (Respond)," NCT00664716, Jan. 1, 2016, retrieved on Feb. 8, 2024, retrieved from URL: <https://clinicaltrials.gov/study/NCT00664716>, 17 pages.
ClinicalTrials.gov [online], "B001 in Patients With CD20 Positive B-cell Non Hodgkin's Lymphoma," NCT03332121, Nov. 15, 2021, retrieved on Feb. 16, 2024, retrieved from URL: <https://clinicaltrials.gov/study/NCT03332121>, 21 pages.
ClinicalTrials.gov [online], "Comparative Pharmacokinetic Trial of RGB-03 and MabThera," NCT02371096, Feb. 25, 2015, retrieved on Feb. 16, 2024, retrieved from URL: <https://clinicaltrials.gov/study/NCT02371096>, 15 pages.
ClinicalTrials.gov [online], "Comparative Study of the Efficacy and Safety of BCD-132 With Teriflunomide and Placebo in Multiple Sclerosis," NCT04056897, Sep. 8, 2021, retrieved on Feb. 20, 2024, retrieved from URL: <https://clinicaltrials.gov/study/NCT04056897>, 31 pages.
ClinicalTrials.gov [online], "First in Human Trial of TAS266 in Patients With Advanced Solid Tumors," NCT01529307, Dec. 21, 2020, retrieved on Feb. 16, 2024, retrieved from URL: <https://clinicaltrials.gov/study/NCT01529307>, 20 pages.
ClinicalTrials.gov [online], "First-in-man Dose Escalation Study of BAY1179470 in Patients With Advanced, Refractory Solid Tumors," NCT01881217, Sep. 14, 2017, retrieved on Feb. 16, 2024, retrieved from URL: <https://clinicaltrials.gov/study/NCT01881217>, 24 pages.
Clinical Trials.gov [online], "Intra-operative Optical Imaging With MDX1201-A488 in Patients With Prostate Cancer," NCT02048150, Mar. 21, 2023, retrieved on Feb. 16, 2024, retrieved from URL: <https://clinicaltrials.gov/study/NCT02048150>, 23 pages.
ClinicalTrials.gov [online], "MabionCD20 Compared to MabThera in Lymphoma Patients (MADILYM)," NCT02617485, Oct. 25, 2023, retrieved on Feb. 16, 2024, retrieved from URL: <https://clinicaltrials.gov/study/NCT02617485>, 51 pages.
ClinicalTrials.gov [online], "Nivolumab Combined With BMS-986253 in HCC Patients," NCT04050462, Aug. 30, 2023, retrieved on Feb. 20, 2024, retrieved from URL: <https://clinicaltrials.gov/study/NCT04050462>, 22 pages.
ClinicalTrials.gov [online], "Pharmacokinetics and Pharmacodynamics of BI 695500 vs. Rituximab as First Line-treatment in Patients With Low Tumor Burden Follicular Lymphoma," NCT01950273, Sep. 5, 2018, retrieved on Feb. 16, 2024, retrieved from URL: <https://clinicaltrials.gov/study/NCT01950273>, 45 pages.
ClinicalTrials.gov [online], "Pharmacokinetics, Efficacy and Safety of the 304 Injection," NCT03980379, Jun. 10, 2019, retrieved on Feb. 20, 2024, retrieved from URL: <https://clinicaltrials.gov/study/NCT03980379>, 22 pages.
ClinicalTrials.gov [online], "Phase 1 Study of INBRX-109 in Subjects With Locally Advanced or Metastatic Solid Tumors Including Sarcomas," NCT03715933, Feb. 15, 2024, retrieved on Feb. 16, 2024, retrieved from URL: <https://clinicaltrials.gov/study/NCT03715933>, 29 pages.
ClinicalTrials.gov [online], "Phase 1/2 Study of OBI-999 in Patients With Advanced Solid Tumors," NCT04084366, Jan. 5, 2024, retrieved on Feb. 20, 2024, retrieved from URL: <https://clinicaltrials.gov/study/NCT04084366>, 26 pages.
ClinicalTrials.gov [online], "Phase 2 Study to Evaluate Safety & Efficacy of VPI 2690B in Diabetic Nephropathy Patients," NCT02251067, Mar. 28, 2017, retrieved on Feb. 16, 2024, retrieved from URL: <https://clinicaltrials.gov/study/NCT02251067>, 18 pages.
ClinicalTrials.gov [online], "Pilot Study With CY, Pembrolizumab, GVAX, and IMC-CS4 (LY3022855) in Patients With Borderline Resectable Adenocarcinoma of the Pancreas," NCT03153410, Jan. 29, 2024, retrieved on Feb. 16, 2024, retrieved from URL: <https://clinicaltrials.gov/study/NCT03153410>, 24 pages.
ClinicalTrials.gov [online], "Preoperative Immunotherapy in Patients With Squamous Cell Carcinoma of the Head and Neck," NCT03708224, Jan. 17, 2023, retrieved on Feb. 16, 2024, retrieved from URL: <https://clinicaltrials.gov/study/NCT03708224>, 32 pages.
ClinicalTrials.gov [online], "RHCACD20MA (HS006) With CHOP (Hi-CHOP) in Patients With Previously Untreated Diffuse Large B-cell Lymphoma (Hi-CHOP)," NCT03485118, Apr. 2, 2018, retrieved on Feb. 16, 2024, retrieved from URL: <https://clinicaltrials.gov/study/NCT03485118>, 23 pages.
ClinicalTrials.gov [online], "Safety and Pharmacokinetic Study of IMM0306 in Patients With Refractory or Relapsed CD20-positive B-cell Non-Hodgkin's Lymphoma (B-NHL)," NCT04746131, Sep. 26, 2022, retrieved on Feb. 20, 2024, retrieved from URL: <https://clinicaltrials.gov/study/NCT04746131>, 18 pages.
ClinicalTrials.gov [online], "Safety, Pharmacokinetics and Pharmacodynamics of Recombinant Chimeric Anti-CD20 Monoclonal Antibody in Patients With B-cell Non-Hodgkin's Lymphoma," NCT02206308, Aug. 1, 2014, retrieved on Feb. 16, 2024, retrieved from URL: <https://clinicaltrials.gov/study/NCT02206308>, 19 pages.
ClinicalTrials.gov [online], "SRK-181 Alone or in Combination With Anti-PD(L)1 Antibody Therapy in Patients With Locally Advanced or Metastatic Solid Tumors (DRAGON)," NCT04291079, Jan. 11, 2024, retrieved on Feb. 20, 2024, retrieved from URL: <https://clinicaltrials.gov/study/NCT04291079>, 26 pages.
ClinicalTrials.gov [online], "Study Evaluating the Safety, Pharmacokinetics, and Pharmacodynamics of MYO-029," NCT00563810, Nov. 26, 2007, retrieved on Feb. 8, 2024, retrieved from URL: <https://clinicaltrials.gov/study/NCT00563810>, 16 pages.
ClinicalTrials.gov [online], "Study of AVE1642 Anti-IGFIR Monoclonal Antibody in Patients With Advanced Multiple Myeloma," NCT01233895, Nov. 3, 2010, retrieved on Feb. 16, 2024, retrieved from URL: <https://clinicaltrials.gov/study/NCT01233895>, 21 pages.
ClinicalTrials.gov [online], "Study of Efficacy and Safety of NIS793 (With and Without Spartalizumab) in Combination With SOC Chemotherapy in First-line Metastatic Pancreatic Ductal Adenocarcinoma (mPDAC) (daNIS-1)," NCT04390763, Jan. 25, 2024, retrieved on Feb. 20, 2024, retrieved from URL: <https://clinicaltrials.gov/study/NCT04390763>, 29 pages.
ClinicalTrials.gov [online], "Study of Idelalisib in Combination With BI 836826 in Participants With Chronic Lymphocytic Leukemia," NCT02538614, Nov. 25, 2020, retrieved on Feb. 16, 2024, retrieved from URL: <https://clinicaltrials.gov/study/NCT02538614>, 47 pages.
ClinicalTrials.gov [online], "Study of JTX 8064, as Monotherapy and in Combination With a PD-1 Inhibitor, in Adult Subjects With Advanced Refractory Solid Tumors," NCT04669899, Feb. 12, 2024, retrieved on Feb. 20, 2024, retrieved from URL: <https://clinicaltrials.gov/study/NCT04669899>, 32 pages.
ClinicalTrials.gov [online], "Study of MK-8808 for Participants With Follicular Lymphoma (MK-8808-001)," NCT01370694, Mar. 15, 2019, retrieved on Feb. 16, 2024, retrieved from URL: <https://clinicaltrials.gov/study/NCT01370694>, 39 pages.
ClinicalTrials.gov [online], "Study of Recombinant Human-Mouse Chimeric Anti-CD20 Monoclonal Antibody to Treat Non-hodgkin's Lymphoma," NCT01459887, Oct. 26, 2011, retrieved on Feb. 16, 2024, retrieved from URL: <https://clinicaltrials.gov/study/NCT01459887>, 23 pages.
ClinicalTrials.gov [online], "Study of STRO-001, an Anti-CD74 Antibody Drug Conjugate, in Patients With Advanced B-Cell Malig-

(56) References Cited

OTHER PUBLICATIONS nancies," NCT03424603, Dec. 14, 2022, retrieved on Feb. 16, 2024, retrieved from URL: <https://clinicaltrials.gov/study/NCT03424603>, 27 pages.
ClinicalTrials.gov [online], "Study of TQB2303 in Patients With CD20-Positive Diffuse Large B-cell Lymphoma (DLBCL)," NCT03777085, May 30, 2019, retrieved on Feb. 16, 2024, retrieved from URL: <https://clinicaltrials.gov/study/NCT03777085>, 21 pages.
ClinicalTrials. gov [online], "Study to Assess the Safety and Tolerability of Multiple Ascending Doses of REGN1033 (SAR391786)," NCT01720576, Sep. 12, 2013, retrieved on Feb. 16, 2024, retrieved from URL: <https://clinicaltrials.gov/study/NCT01720576>, 20 pages.
ClinicalTrials.gov [online], "Study to Evaluate Safety and Tolerability of XmAb13676 (Plamotamab) in Patients With CD20-expressing Hematologic Malignancies," NCT02924402, Dec. 20, 2023, retrieved on Feb. 16, 2024, retrieved from URL: <https://clinicaltrials.gov/study/NCT02924402>, 25 pages.
ClinicalTrials.gov [online], "This Study is to Evaluate Safe and Effective Treatment Dose of OBI-888 in Patients With Locally Advanced or Metastatic Solid Tumors," NCT03573544, Jul. 8, 2022, retrieved on Feb. 16, 2024, retrieved from URL: <https://clinicaltrials.gov/study/NCT03573544>, 26 pages.
ClinicalTrials.gov [online], "TREatment of degenerative and Neoplastic Diseases With Rituximab (TREND)," NCT01277172, Jan. 14, 2011, retrieved on Feb. 16, 2024, retrieved from URL: <https://clinicaltrials.gov/study/NCT01277172>, 22 pages.
ClinicalTrials.gov [online], "Trial of Active Immunotherapy With OBI-833 (Globo H-CRM197) in Advanced/Metastatic Gastric, Lung, Colorectal or Breast Cancer Subjects," NCT02310464, Oct. 3, 2022, retrieved on Feb. 16, 2024, retrieved from URL: <https://clinicaltrials.gov/study/NCT02310464>, 42 pages.
ClinicalTrials.gov [online], "A Study of Paclitaxel/Carboplatin With or Without CDP791 in Patients With Lung Cancer," NCT00152477, Apr. 12, 2022, retrieved on Feb. 8, 2024, retrieved from URL: <https://classic.clinicaltrials.gov/ct2/show/NCT00152477>, 35 pages.
Coiffier, "Pharmacokinetics, efficacy and safety of the rituximab biosimilar CT-P10," Expert Rev. Clin. Pharmacol., Sep. 2017, 10(9):923-933.
Cooper et al., "Human natural killer cells: a unique innate immunoregulatory role for the CD56bright subset," Immunobiology, May 15, 2001, 97 (10): 3146-3151.
Corpet, "Multiple sequence alignment with hierarchical clustering," Nuc. Acids Res., Nov. 25, 1988, 16(22):10881-10890.
Croft et al., "Regulation of T Cell Immunity by OX40 and OX40L," Madame Curie Bioscience Database, 2000-2013, retrieved on Jan. 12, 2022, retrieved from URL <"https://www.ncbi.nlm.nih.gov/books/NBK5990/">, 12 pages.
Crossland, "CD56-Specific T Cells; Using Genetically Engineered T Cells to Redirect Specificty to a T Cell Expressed Antigen" Dissertation for the degree of PhD, The University of Texas MD Anderson Cancer Center UTHealth Graduate School of Biomedical Sciences, Aug. 2014, 232 pages.
D' Angelo et al., "A phase 2 study of ontuxizumab, a monoclonal antibody targeting endosialin, in metastatic melanoma," Invest. New Drugs, Feb. 2018, 36(1):103-113.
Dalili et al., "A Review of Sorting, Separation and Isolation of Cells and Microbeads for Biomedical Applications: Microfluidic Approaches," Analyst, 2019, 144:87-113.
Damjanov et al., "Safety and efficacy of SBI-087, a subcutaneous agent for B cell depletion, in patients with active rheumatoid arthritis: results from a phase II randomized, double-blind, placebo-controlled study," J. Rheumatol., Dec. 2016, 43(12):2094-2100.
De Bono et al., "Phase I trial of a murine antibody to MUC1 in patients with metastatic cancer: evidence for the activation of humoral and cellular antitumor immunity," Ann Oncol., Dec. 2004, 15(12):1825-33.
De Weers et al., "Daratumumab, a novel therapeutic human CD38 monoclonal antibody, induces killing of multiple myeloma and other hematological tumors," J. Immunol., Feb. 2011, 186(3):1840-1848.

Dotti et al., "Design and Development of Therapies using Chimeric Antigen Receptor-Expressing T cells," Immunol Rev., Jan. 2014, 257(1)1-35.
Du et al., "Next-generation anti-CD20 monoclonal antibodies in autoimmune disease treatment," Autoimmunity Highlights, Dec. 2017, 8(1):1-2.
European Search Report in European Application No. 21809551.1, dated May 29, 2024, 11 pages.
Extended European Search Report in European Patent Appln No. 18878132.2, dated Jul. 14, 2021, 10 pages.
Forero et al., "First-in-human study of the antibody DR5 agonist DS-8273a in patients with advanced solid tumors," Invest New Drugs, Jan. 3, 2017, 35(3):298-306.
Fox et al., "A phase 2 multicenter study of ublituximab, a novel glycoengineered anti-CD20 monoclonal antibody, in patients with relapsing forms of multiple sclerosis," Mult. Scler., Mar. 2021, 27(3):420-429.
Fulciniti et al., "Anti-DKK1 mAb (BHQ880) as a potential therapeutic agent for multiple myeloma," Blood, Jul. 9, 2009, 114(2):371-9.
Gacerez et al., "How chimeric antigen receptor design affects adoptive T cell therapy" J. Cell Physiol., Dec. 2016, 231(12):2590-2598.
Gagez et al., "Obinutuzumab: a new class of anti-CD20 monoclonal antibody," Curr. Opin. Oncol., Sep. 2014, 26(5):484-491.
Garcia et al., "Bevacizumab (Avastin®) in cancer treatment: A review of 15 years of clinical experience and future outlook," Cancer Treat Rev., Jun. 2020, 86:102017.
GenBank Accession No. AB590584.1, "Synthetic construct DNA, clone: pFN21AE1768, *Homo sapiens* TNFRSF4 gene for tumor necrosis factor receptor superfamily, member 4, without stop codon, in Flexi system," Jul. 25, 2016, 2 pages.
GenBank Accession No. AF461811.1, "*Homo sapiens* NKG2D mRNA, complete cds" Jan. 17, 2002, 2 pages.
GenBank Accession No. N_000734.3, "*Homo sapiens* CD247 molecule (CD247), transcript variant 2, mRNA" Mar. 15, 2015, 5 pages.
GenBank Accession No. NM_001561.5, "*Homo sapiens* tumor necrosis factor receptor superfamily member 9 (TNFRSF9), mRNA" Nov. 20, 2015, 5 pages.
GenBank Accession No. NM_001768.6, "*Homo sapiens* CD8a molecule (CD8A), transcript variant 1, Mrna," Mar. 15, 2015, 4 pages.
GenBank Accession No. NM_003326.4, "*Homo sapiens* TNF superfamily member 4 (TNFSF4), transcript variant 1, mRNA" Nov. 21, 2015, 4 pages.
GenBank Accession No. NM_006139.3, "*Homo sapiens* CD28 molecule (CD28), transcript variant 1, mRNA," Mar. 15, 2015, 5 pages.
GenBank Accession No. X52645.1 "Human Fc-gamma RIII-2 cDNA for Fc-gamma receptor III-2 (CD16)," Oct. 7, 2008, 2 pages.
Genovese et al., "Ocrelizumab, a humanized anti-CD20 monoclonal antibody, in the treatment of patients with rheumatoid arthritis: a phase I/II randomized, blinded, placebo-controlled, dose-ranging study," Arthritis Rheum., Sep. 2008, 58(9):2652-61.
Geoghegan et al., "Inhibition of CD73 Amp hydrolysis by a therapeutic antibody with a dual, non-competitive mechanism of action," MAbs, Apr. 2, 2016, 8(3):454-67.
Gibson et al., "Randomized Phase III Trial Results of Panitumumab, a Fully Human Anti-Epidermal Growth Factor Receptor Monoclonal Antibody, in Metastatic Colorectal Cancer," Clin Colorectal Cancer, May 1, 2006, 6(1):29-31.
Gilbert et al., "Effect of CC chemokine receptor 2 CCR2 blockade on serum C-reactive protein in individuals at atherosclerotic risk and with a single nucleotide polymorphism of the monocyte chemoattractant protein-1 promoter region," Am. J. Cardiol., Mar. 15, 2011, 107(6):906-11.
Glazyrin et al., "Direct Detection of Herceptin/Transtuzumab Binding on Breast Tissue Sections," J Histology & Cytochemistry, 2007, 55(1):25-33.
Golan et al., "LY2495655, an antimyostatin antibody, in pancreatic cancer: a randomized, phase 2 trial," J. Cachexia Sarcopenia Muscle, Oct. 2018, 9(5):871-879.

(56) References Cited

OTHER PUBLICATIONS

Gold et al., "Mapping PAM4 (clivatuzumab), a monoclonal antibody in clinical trials for early detection and therapy of pancreatic ductal adenocarcinoma, to MUC5AC mucin," Molecular Cancer, Dec. 2013, 12(143):1-8.
Goldenberg et al., "Veltuzumab (humanized anti-CD20 monoclonal antibody): characterization, current clinical results, and future prospects," Leuk. Lymphoma, May 2010, 51(5):747-755.
Goldenberg, "Trastuzumab, a recombinant DNA-derived humanized monoclonal antibody, a novel agent for the treatment of metastatic breast cancer," Clin. Ther., Feb. 1999, 21(2):309-18.
Gross et al., "Five-Year Outcomes of Panretinal Photocoagulation vs Intravitreous Ranibizumab for Proliferative Diabetic Retinopathy: A Randomized Clinical Trial," JAMA Ophthalmol., Oct. 2018, 136(10):1138-1148.
Gupta et al., "Targeting CA 19-9 with a humanized monoclonal antibody at the time of surgery may decrease recurrence rates for patients undergoing resections for pancreatic cancer, cholangiocarcinoma and metastatic colorectal cancer," J. Gastrointest. Oncol., Apr. 2020, 11(2):231-235.
Hammer et al., "Preclinical Efficacy of a PSMA-Targeted Thorium-227 Conjugate (PSMA-TTC), a Targeted Alpha Therapy for Prostate Cancer," Clin. Cancer Res., Apr. 15, 2020, 26(8):1985-1996.
Hancock et al., "A Monoclonal Antibody against the c-erbB-2 Protein Enhances the Cytotoxicity of cis-Diamminedichloroplatinum against Human Breast and Ovarian Tumor Cell Lines," Cancer Res., Sep. 1, 1991, 51:4575-4580.
Harwerth et al., "Monoclonal Antibodies against the Extracellular Domain of erbB-2 Receptor Function as Partial Ligand Agonists," J Biol. Chem., Jul. 25, 1992, 267(21):15160-15167.
Hashimoto et al., "A novel HER3-targeting antibody-drug conjugate, U3-1402, exhibits potent therapeutic efficacy through the delivery of cytotoxic payload by efficient internalization," Clin. Cancer Res., Dec. 2019, 25(23):7151-7161.
Hassan et al., "First-in-human, multicenter, phase I dose-escalation and expansion study of anti-mesothelin antibody-drug conjugate anetumab ravtansine in advanced or metastatic solid tumors," J. Clin. Oncol., Jun. 6, 2020, 38(16):1824-1835.
Hassan et al., "Mesothelin immunotherapy for cancer: ready for prime time?," J. Clin. Oncol., Dec. 12, 2016, 34(34):4171-4179.
Hensel et al., "Early development of PAT-SM6 for the treatment of melanoma," Melanoma Res., Aug. 2013, 23(4):264-75.
Hernandez-Hoyos et al., "MOR209/ES414, a novel bispecific antibody targeting PSMA for the treatment of metastatic castration-resistant prostate cancer," Mol. Cancer Ther., Sep. 2016, 15(9):2155-2165.
Hersey et al., "A randomized phase 2 study of etaracizumab, a monoclonal antibody against integrin alpha(v)beta(3), + or— dacarbazine in patients with stage IV metastatic melanoma," Cancer, Mar. 15, 2010, 116(6):1526-1534.
Heublin et al., "Potential interplay of the gatipotuzumab epitope TA-MUC1 and estrogen receptors in ovarian cancer," Int. J. Mol. Sci., Jan. 12, 2019, 20(2):295.
Higgins et al., "CLUSTAL: a package for performing multiple sequence alignment on a microcomputer," Gene, 1988, 73:237-244.
Higgins et al., "Fast and sensitive multiple sequence alignments on a microcomputer," Cabios Commuications, 1989, 5(2):151-153.
Hosseini et al., "Mitigating the risk of cytokine release syndrome in a Phase I trial of CD20/CD3 bispecific antibody mosunetuzumab in NHL: impact of translational system modeling," NPJ Syst. Biol. Appl., Aug. 28, 2020,6(1):28.
Hoy, "Dinutuximab: A Review in High-Risk Neuroblastoma," Target Oncol., Apr. 2016, 11(2):247-53.
Hoy, "Tafasitamab: first approval," Drugs, Nov. 2020, 80(16):1731-1737.
Hsu et al., "The Killer Cell Immunoglobulin-Like Receptor (KIR) Genomic Region: Gene-Order, Haplotypes and Allelic Polymorphism," Immunological Review, Dec. 2002, 190:40-52.

Hu et al., "Epitope mapping and structural analysis of an anti-ErbB2 antibody A21: Molecular basis for tumor inhibitory mechanism," Proteins, Feb. 15, 2008, 70(3):938-949.
Huang et al., "Parallelization of a local similarity algorithm," Cabios, 1992, 8(2):155-165.
Huang et al., "The CD20-specific engineered toxin antibody MT-3724 exhibits lethal effects against mantle cell lymphoma," Blood Cancer J., Mar. 20, 2018, 8(3):33.
Hudecek et al., "Going Non-Viral: the Sleeping Beauty Transposon System Breaks on Through to the Clinical Side," Critical Reviews in Biochemistry and Molecular Biology, Jul. 4, 2017, 52(4):355-380.
Hughes et al., "Have Clinical Trials Properly Assessed c-Met Inhibitors?," Trends Cancer, Feb. 2018, 4(2):94-97.
Hummel et al., "Pasotuxizumab, a BiTE® immune therapy for castration-resistant prostate cancer: Phase I, dose-escalation study findings," Immunotherapy, Feb. 2021, 13(2):125-141.
International Preliminary Report on Patentability in International Appln. No. PCT/KR2018/013928, dated May 19, 2020, 17 pages (with English Translation).
International Preliminary Report on Patentability in International Appln. No. PCT/KR2021/006361, mailed on Dec. 1, 2022, 9 pages.
International Search Report and Written Opinion in International Appln. No. PCT/KR2018/013928, dated Mar. 15, 2019, 25 pages (with English Translation).
International Search Report and Written Opinion in International Appln. No. PCT/KR2021/006361, dated Nov. 25, 2021, 14 pages.
Ishiguro et al., "An anti-glypican 3/CD3 bispecific T cell-redirecting antibody for treatment of solid tumors," Sci. Transl. Med., Oct. 4, 2017, 9(410):eaal4291.
Jiang et al., "Abituzumab targeting of αV-class integrins inhibits prostate cancer progression," Mol. Cancer Res., Jul. 2017, 15(7):875-883.
Jiang et al., "Pharmacokinetics and safety of IBI301 versus rituximab in patients with CD20+ B-cell lymphoma: a multicenter, randomized, double-blind, parallel-controlled study," Sci. Rep., Jul. 15, 2020, 10(1):11676.
Jonker et al., "Cetuximab for the treatment of colorectal cancer," N. Engl. J. Med., Nov. 15, 2007,357(20):2040-2048.
Kalaycio et al., "Subcutaneous injections of low doses of humanized anti-CD20 veltuzumab: a phase I study in chronic lymphocytic leukemia," Leuk. Lymphoma, 2016, 57(4):803-11.
Kang et al., "Drozitumab, a human antibody to death receptor 5, has potent antitumor activity against rhabdomyosarcoma with the expression of caspase-8 predictive of response," Clin. Cancer Res., May 15, 2011, 17(10):3181-92.
Kappos et al., "Ocrelizumab in relapsing-remitting multiple sclerosis: a phase 2, randomised, placebo-controlled, multicentre trial," Lancet., Nov. 19, 2011, 378(9805):1779-87.
Kasprzyk et al., "Therapy of an Animal Model of Human Gastric Cancer Using a Combination of Anti-erbB-2 Monoclonal Antibodies," Cancer Research, May 15, 1992, 52:2771-2776.
Khan et al., "Ramucirumab for the treatment of gastric or gastroesophageal junction cancer," Expert Opin. Biol. Ther., Nov. 2019, 19(11):1135-1141.
Kim et al., "First-in-Human Phase I Study of Aprutumab Ixadotin, a Fibroblast Growth Factor Receptor 2 Antibody-Drug Conjugate (BAY 1187982) in Patients with Advanced Cancer," Target Oncol., Oct. 2019, 14(5):591-601.
Kim et al., "Phase II study of ensituximab, a novel chimeric monoclonal antibody, in adults with unresectable, metastatic colorectal cancer," Clin. Cancer Res., Jul. 15, 2020, 26(14):3557-3564.
Klapper et al., "A subclass of tumor inhibitory monoclonal antibodies to ErbB-2/HER2 blocks crosstalk with growth factor receptors," Oncogene, Jan. 1997, 14:2099-2109.
Koene et al., "FcγRIIIa-158V/F Polymorphism Influences the Binding of IgG by Natural Killer Cell FcγRIIIa, Independently of the FcγRIIIa-48L/R/H Phenotype," Blood, Aug. 1997, 90(3):1109-1114.
Kruschinski et al., "Engineering antigen-specific primary human NK cells against HER-2 positive carcinomas," Proceedings of the National Academy of Sciences, Nov. 11, 2008, 105(45):17481-17486.

(56) References Cited

OTHER PUBLICATIONS

Kuenen et al., "A phase I pharmacologic study of necitumumab (IMC-11F8), a fully human IgG1 monoclonal antibody directed against EGFR in patients with advanced solid malignancies," Clin. Cancer Res., Mar. 15, 2010, 16(6):1915-23.
Leary et al., "Abstract No. 2521: First-in-human first-in-class phase I trial of murlentamab, an anti-Mullerian-hormone receptor II (AMHRII) monoclonal antibody acting through tumor-associated macrophage (TAM) engagement, as single agent and in combination with carboplatin (C) and paclitaxel (P) in AMHRII-expressing advanced/metastatic gynecological cancer patients (pts)," Presented at ASCO 2019, Chicago, Illinois, May 31-Jun. 4, 2019; Journal of Clinical Oncology, May 20, 2019, 37,(15_suppl.), 2 p.
Lee et al., "Preclinical pharmacokinetics, interspecies scaling, and pharmacokinetics of a Phase I clinical trial of TTAC-0001, a fully human monoclonal antibody against vascular endothelial growth factor 2," Drug Des. Devel. Ther., Mar. 8, 2018, 12:495-504.
Lima et al., "Phase Ib study of drozitumab combined with first-line mFOLFOX6 plus bevacizumab in patients with metastatic colorectal cancer," Cancer Invest., Dec. 2012, 30(10):727-31.
Liu et al., "Driving better and safer HER2-specific CARs for cancer therapy," Oncotarget, Sep. 5, 2017, 8(37):62730-62741.
Liu et al., "Identification of PAM4 (clivatuzumab)-reactive epitope on MUC5AC: a promising biomarker and therapeutic target for pancreatic cancer," Oncotarget., Feb. 28, 2015, 6(6):4274-85.
Liu et al., "Phase I study of safety and pharmacokinetics of the anti-MUC16 antibody-drug conjugate DMUC5754A in patients with platinum-resistant ovarian cancer or unresectable pancreatic cancer," Ann. Oncol., Nov. 2016, 27(11):2124-2130.
Liu et al., "Use of CAR-Transduced Natural Killer Cells in CD19-Positive Lymphoid Tumors," N. Engl. J. Med., Feb. 6, 2020, 382(6):545-553.
Lonial et al., "Elotuzumab Therapy for Relapsed or Refractory Multiple Myeloma," N. Engl. J. Med., Aug. 13, 2015, 373(7):621-631.
Lord et al., "Structure-based engineering to restore high affinity binding of an isoform-selective anti-TGFβ1 antibody," MAbs., Apr. 2018, 10(3):444-452.
LoRusso et al., "Icrucumab, a fully human monoclonal antibody against the vascular endothelial growth factor receptor-1, in the treatment of patients with advanced solid malignancies: a Phase 1 study," Invest. New. Drugs, Apr. 2014, 32(2):303-11.
Mahalingham et al., "Phase I study of imalumab (BAX69), a fully human recombinant antioxidized macrophage migration inhibitory factor antibody in advanced solid tumours," Br. J. Clin. Pharmacol., Sep. 2020, 86(9):1836-1848.
Maier et al., "Requirements for the Internalization of a Murine Monoclonal Antibody Directed against the HEER-2/neu Gene Product c-erbB-2," Cancer Res., Oct. 1, 1991, 51:5361-5369.
Marchio et al. "Evolving concepts in HER2 evaluation in breast cancer: Heterogeneity, HER2-low carcinomas and beyond," Semin Cancer Biol, Feb. 26, 2020, 72:123-135.
Marcus et al., "Obinutuzumab for the First-Line Treatment of Follicular Lymphoma," N. Engl. J. Med., Oct. 5, 2017, 377(14):1331-1344.
Markham, "Naxitamab: First Approval," Drugs, Feb. 2021, 81(2):291-296.
Martin et al., "Phase I trial of isatuximab monotherapy in the treatment of refractory multiple myeloma," Blood Cancer J., Mar. 29, 2019, 9(4):41, 10 pages.
Martinsson-Niskanen et al., "Monoclonal antibody TB-403: a first-in-human, Phase I, double-blind, dose escalation study directed against placental growth factor in healthy male subjects," Clin. Ther., Sep. 2011, 33(9):1142-9.
Milone et al., "Clinical Use of Lentiviral Vectors," Leukemia, Jul. 2018, 32(7):1529-41.
Musolino et al., "Immunoglobulin G Fragment C Receptor Polymorphisms and Clinical Efficacy of Trastuzumab-Based Therapy in Patients with HER-2/neu-Positive Metastatic Breast Cancer," J. Clin. Oncol., Apr. 10, 2008, 26(11):1789-1796.

Nadafi et al., "Anti-CD19 Monoclonal Antibodies: a New Approach to Lymphoma Therapy," Int. J. Mol. Cell Med., 2015, 4(3):143-151.
Nahta et al., "The HER-2-Targeting Antibodies Transtuzumab and Pertuzumab Synergistically Inhibit the Survival of Breast Cancer Cells", Cancer Research, Apr. 2004, 64(7): 2343-2346.
Needleman et al., "A General Method Applicable to the Search for Similarities in the Amino Acid Sequence of Two Proteins," J Mol. Biol., 1970, 48:443-453.
Niederwieser et al., "Efficacy and Safety of ABP 798: Results from the Jasmine Trial in Patients with Follicular Lymphoma in Comparison with Rituximab Reference Product," Target Oncol., Oct. 2020, 15(5):599-611.
O'Day et al., "A randomised, phase II study of intetumumab, an anti-αv-integrin mAb, alone and with dacarbazine in stage IV melanoma," Br. J. Cancer, Jul. 26, 2011, 105(3):346-52.
Office Action in Australian Appln. No. 2018370195, dated Jul. 6, 2021, 5 pages.
Office Action in Chinese Appln. No. 201880074007.4, dated Feb. 25, 2023, 15 pages (with English translation).
Office Action in Indian Appln. No. 202017023032, dated Oct. 31, 2022, 6 pages.
Office Action in Japanese Appln. No. 2020-544730, dated Dec. 14, 2021, 11 pages (with English Translation).
Office Action in Japanese Appln. No. 2020-544730, dated May 23, 2022, 4 pages (with English Translation).
Office Action in Japanese Appln. No. 2020-544730, dated May 26, 2021, 12 pages (with English Translation).
Office Action in Korean Application No. 10-2018-0140251, dated Apr. 25, 2024, 13 pages (with English Translation).
Okamoto et al., "TAK-701, a humanized monoclonal antibody to hepatocyte growth factor, reverses gefitinib resistance induced by tumor-derived HGF in non-small cell lung cancer with an EGFR mutation," Mol. Cancer Ther., Oct. 2010, 9(10):2785-92.
Overdijk et al., "Dual Epitope Targeting and Enhanced Hexamerization by DR5 Antibodies as a Novel Approach to Induce Potent Antitumor Activity Through DR5 Agonism," Mol. Cancer Ther., Oct. 2020, 19(10):2126-2138.
Petrylak et al., "PSMA ADC monotherapy in patients with progressive metastatic castration-resistant prostate cancer following abiraterone and/or enzalutamide: Efficacy and safety in open-label single-arm phase 2 study," Prostate, Jan. 2020, 80(1):99-108.
Piloto et al., "IMC-EB10, an anti-FLT3 monoclonal antibody, prolongs survival and reduces nonobese diabetic/severe combined immunodeficient engraftment of some acute lymphoblastic leukemia cell lines and primary leukemic samples," Cancer Res., May 2006, 66(9):4843-51.
Plummer et al., "Phase 1 and pharmacokinetic study of lexatumumab in patients with advanced cancers," Clin. Cancer Res., Oct. 15, 2007, 13(20):6187-94.
Poddubnaya et al., "Proposed rituximab biosimilar BCD-020 versus reference rituximab for treatment of patients with indolent non-Hodgkin lymphomas: An international multicenter randomized trial," Hematol. Oncol., Feb. 2020, 38(1):67-73.
Pognan et al., "Colony-stimulating factor-1 antibody lacnotuzumab in a phase 1 healthy volunteer study and mechanistic investigation of safety outcomes.," J Pharmacol Exp Ther., Jun. 2019, 369(3):428-442.
Ponath et al., "A Novel, Fully Human Anti-fucosyl-GM1 Antibody Demonstrates Potent In Vitro and In Vivo Antitumor Activity in Preclinical Models of Small Cell Lung Cancer," Clin Cancer Res., Oct. 15, 2018, 24(20):5178-5189.
Pyo et al., "Different Patterns of Evolution in the Centromeric and Telomeric Regions of Group A and B Haplotypes of the Human Killer Cell Ig-like Receptor Locus," PLoS One, Dec. 29, 2010, 5(12)e15115:1-14.
Rafiq et al, "Engineering strategies to overcome the current roadblocks in CAR T cell therapy," Nature Reviews Clinical Oncology, Mar. 2020, 17(3):147-167.
Reck et al., "A randomized, double-blind, placebo-controlled phase 2 study of tigatuzumab (CS-1008) in combination with carboplatin/paclitaxel in patients with chemotherapy-naïve metastatic/unresectable non-small cell lung cancer," Lung Cancer, Dec. 2013, 82(3):441-448.

(56) References Cited

OTHER PUBLICATIONS

Rice et al., "Fresolimumab treatment decreases biomarkers and improves clinical symptoms in systemic sclerosis patients," J Clin Invest., Jul. 2015, 125(7):2795-2807.
Robak, "Ofatumumab, a human monoclonal antibody for lymphoid malignancies and autoimmune disorders," Curr Opin Mol Ther., Jun. 2008, 10(3):294-309.
Rockberg et al., "Discovery of epitopes for targeting the human epidermal growth factor receptor 2 (HER2) with antibodies," Molecular Oncology, Jun. 2009, 3(3):238-247.
Rosevear et al., "Conatumumab, a fully human mAb against death receptor 5 for the treatment of cancer," Curr Opin Investig Drugs, Jun. 2010, 11(6):688-698.
Ross et al., "The HER-2/neu Gene and Protein in Breast Cancer2003: Biomarker and Target of Therapy," The Oncologist, 2003, 8(4):307-325, 19 pages.
Sabbatini et al., "Abagovomab as maintenance therapy in patients with epithelial ovarian cancer: a phase III trial of the AGO OVAR, COGI, GINECO, and GEICO—the MIMOSA study," J Clin Oncol., Apr. 20, 2013, 31(12):1554-1561.
Sadelain et al., "The Basic Principles of Chimeric Antigen Receptor Design," Cancer Discovery, Apr. 2013, 3:388-398.
Salles et al., "Rituximab in B-Cell Hematologic Malignancies: A Review of 20 Years of Clinical Experience," Adv Ther., Oct. 2017, 34(10):2232-2273.
Sapino et al., "Patients with advanced stage breast carcinoma immunoreactive to biotinylated Herceptin® are most likely to benefit from trastuzumab-based therapy: an hypothesis-generating study," Annals of Oncology, Dec. 2007, 18(12):1963-1968, 6 pages.
Sasikumar et al., "Peptide and Peptide-Inspired Checkpoint Inhibitors: Protein Fragments to Cancer Immunotherapy," Medicine in Drug Discovery, Dec. 2020, 8(100073):1-10.
Sato et al., "Profile of farletuzumab and its potential in the treatment of solid tumors," Onco Targets Ther., Mar. 7, 2016, 9:1181-1188.
Sawas et al., "A phase 1/2 trial of ublituximab, a novel anti-CD20 monoclonal antibody, in patients with B-cell non-Hodgkin lymphoma or chronic lymphocytic leukaemia previously exposed to rituximab," Br J Haematol., Apr. 2017, 177(2):243-253.
Schönfeld et al., "Selective Inhibition of Tumor Growth by Clonal NK Cells Expressing an ErbB2/HER2-Specific Chimeric Antigen Receptor," Molecular Therapy, Nov. 6, 2014, 23(2):330-338.
Segal et al., "Phase I Study of Single-Agent Utomilumab (PF-05082566), a 4-1BB/CD137 Agonist, in Patients with Advanced Cancer," Clin Cancer Res., Apr. 15, 2018, 24(8):1816-1823.
Segal et al., "Results from an Integrated Safety Analysis of Urelumab, an Agonist Anti-CD137 Monoclonal Antibody," Clin Cancer Res., Apr. 15, 2017, 23(8):1929-1936.
Sharman et al., "A Randomized, Double-Blind, Efficacy and Safety Study of PF-05280586 (a Rituximab Biosimilar) Compared with Rituximab Reference Product (MabThera®) in Subjects with Previously Untreated CD20-Positive, Low-Tumor-Burden Follicular Lymphoma (LTB-FL)," BioDrugs, Apr. 2020, 34(2):171-181.
Shawver et al., "Ligand-like Effects Induced by Anti-c-erbB-2 Antibodies Do Not Correlate with and Are Not Required for Growth Inhibition of Human Carcinoma Cells," Cancer Res., Mar. 1, 1994, 54:1367-1373.
Shi et al., "A phase 3 study of rituximab biosimilar HLX01 in patients with diffuse large B-cell lymphoma," J Hematol Oncol., Apr. 16, 2020, 13(1):38, 5 pages.
Simonelli et al., "Phase I study of PF-03446962, a fully human monoclonal antibody against activin receptor-like kinase-1, in patients with hepatocellular carcinoma," Ann Oncol., Sep. 2016, 27(9):1782-1787.
Smith and Waterman, "Identification of common molecular subsequences," J Mol Biol., Mar. 25, 1981, 147(1):195-197.
Smith et al., "Comparison of biosequences," Adv. Appl. Math., Dec. 1981, 2(4):482-489.
Smolen et al., "A randomised, double-blind trial to demonstrate bioequivalence of GP2013 and reference rituximab combined with methotrexate in patients with active rheumatoid arthritis," Ann Rheum Dis., Sep. 2017, 76(9):1598-1602.
Sorensen et al., "Safety and efficacy of ofatumumab in relapsing-remitting multiple sclerosis: a phase 2 study," Neurology, Feb. 18, 2014, 82(7):573-581.
Stancovski et al., "Mechanistic aspects of the opposing effects of monoclonal antibodies to the ERBB2 receptor on tumor growth," PNAS USA, Oct. 1, 1991, 88(19):8691-8695.
Stasi, "Gemtuzumab ozogamicin: an anti-CD33 immunoconjugate for the treatment of acute myeloid leukaemia," Expert Opin Biol Ther., Apr. 2008, 8(4):527-540.
Strouhalova et al., "Vimentin intermediate filaments as potential target for cancer treatment," Cancers, Jan. 11, 2020, 12(1):184, 20 pages.
Sun et al., "Construction and evaluation of a novel humanized HER2-specific chimeric receptor," Breast Cancer Research, Jun. 11, 2014, 16:R61, 10 Pages.
Swords et al., "KB004, a first in class monoclonal antibody targeting the receptor tyrosine kinase EphA3, in patients with advanced hematologic malignancies: Results from a phase 1 study.," Leuk Res., Nov. 2016, 50:123-131.
Tagliabue et al., "Selection of monoclonal antibodies which induce internalization and phosphorylation of P185HER2 and growth inhibition of cells with HER2/neu gene amplification," Int. J Cancer, Apr. 1, 1991, 47(6):933-937.
Takebe et al., "Targeting Notch signaling pathway in cancer: clinical development advances and challenges," Pharmacol Ther., Feb. 2014, 141(2):140-149.
Tolcher et al., "A phase 1 study of anti-TGFβ receptor type-II monoclonal antibody LY3022859 in patients with advanced solid tumors," Cancer Chemother Pharmacol., Apr. 2017, 79(4):673-680.
Tolcher et al., "Cantuzumab mertansine, a maytansinoid immunoconjugate directed to the CanAg antigen: a phase I, pharmacokinetic, and biologic correlative study," J Clin Oncol., Jan. 15, 2003, 21(2):211-222.
Uhlman et al., "Antisense oligonucleotides: a new therapeutic principle," Chemical Reviews, Jun. 1, 1990, 90(4):543-584.
UniProtKB Accession No. P40933, "RecName: Full=Interleukin-15; Short=IL-15; Flags: Precursor," Dec. 24, 2019, 6 pages.
UniProtKB Accession No. P41273, "RecName: Full=Tumor necrosis factor ligand superfamily member 9; AltName: Full=4-1BB ligand; Short=4-1BBL," Oct. 16, 2019, 5 pages.
Vaickus, "Immune markers in hematologic malignancies," Crit Rev. in Oncol./Hemotol., Dec. 1991, 11(4):267-297.
Vallabhajosula et al., "Radioimmunotherapy of Metastatic Prostate Cancer with 177Lu-DOTAhuJ591 Anti Prostate Specific Membrane Antigen Specific Monoclonal Antibody," Curr Radiopharm., 2016, 9(1):44-53.
Van der Horst et al., "Epcoritamab induces potent anti-tumor activity against malignant B-cells from patients with DLBCL, FL and MCL, irrespective of prior CD20 monoclonal antibody treatment," Blood Cancer J., Feb. 18, 2021, 11(38):1-8.
Vose et al., "Multicenter phase II study of iodine-131 tositumomab for chemotherapy-relapsed/refractory low-grade and transformed low-grade B-cell non-Hodgkin's lymphomas," J Clin Oncol., Mar. 2000, 18(6):1316-1323.
Waddell et al., "Potential role of rilotumumab in the treatment of gastric cancer," Immunotherapy, Dec. 2014, 6(12):1243-1253.
Wagner et al., "Randomized phase 2 trial and open-label extension of domagrozumab in Duchenne muscular dystrophy," Neuromuscul Disord., Jun. 2020, 30(6):492-502.
Wall et al., "The anti-DKK1 antibody DKN-01 as an immunomodulatory combination partner for the treatment of cancer," Expert Opin Investig Drugs., Jul. 2, 2020, 29(7):639-644.
Webb et al., "OX40, OX40L and Autoimmunity: a Comprehensive Review," Clinic Rev. Allerg. Immunol., 2016, 50: 312-332.
Wilkie et al., "Retargeting of Human T Cells to Tumor-Associated MUC1: The Evolution of a Chimeric Antigen Receptor," The Journal of Immunology, 2008, 180:4901-9.
Wiseman et al., "Phase I/II 90 Y-Zevalin (yttrium-90 ibritumomab tiuxetan, IDEC-Y2B8) radioimmunotherapy dosimetry results in relapsed or refractory non-Hodgkin's lymphoma," Eur J Nucl Med., 2000, 27(7):766-777.

(56) References Cited

OTHER PUBLICATIONS

Witzig et al., "Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma," J Clin Oncol., May 15, 2002, 20(10):2453-2463.

Wolff et al., "Human Epidermal Growth Factor Receptor 2 Testing in Breast Cancer," Arch Pathol Lab Med., Nov. 2018, 142(11):1364-1382.

Wu et al., "piggyBac is a Flexible and Highly Active Transposon as Compared to Sleeping Beauty, Tol2, and Mos1 in Mammalian Cells," PNAS, Oct. 10, 2006, 103(41):15008-15013.

Xu et al., "Antibody-induced growth inhibition is mediated through immunochemically and functionally distinct epitopes on the extracellular domain of the c-erbb-2 (her-2/neu) gene product p185," Int. J Cancer, Feb. 1, 1993, 53:401-408.

Yamashita-Kashima et al., "Pertuzumab in Combination with Trastuzumab Shows Significantly Enhanced Antitumor Activity in HER2-Positive Human Gastric Cancer Xenograft Models", Clinical Cancer Research, Jun. 2011, 17(15):5060-5071.

Yoo et al., "Phase I study of bintrafusp alfa, a bifunctional fusion protein targeting TGF-$\beta$ and PD-L1, in patients with pretreated biliary tract cancer.," J Immunother Cancer, May 2020,8(1):e000564, 9 pages.

Yu et al., "Antibody-drug conjugates in clinical trials for lymphoid malignancies and multiple myeloma," Journal of Hematology & Oncology, Dec. 2019, 12(94):1-7.

Zelenetz, "A clinical and scientific overview of tositumomab and iodine I 131 tositumomab," Semin Oncol., Apr. 2003, 30(2 Suppl 4):22-30.

Zhang et al., "A novel anti-DR5 antibody-drug conjugate possesses a high-potential therapeutic efficacy for leukemia and solid tumors.," Theranostics., Jul. 13, 2019, 9(18):5412-5423.

Zhang et al., "ErbB2/HER2-Specific NK Cells for Targeted Therapy of Glioblastoma," Journal of the National Cancer Institute, Dec. 6, 2015, 108(5):djv375, 12 pages.

U.S. Appl. No. 18/816,413, filed Aug. 27, 2024, Lee et al.

Jena et al., "Redirecting T-cell specificity by introducing a tumor-specific chimeric antigen receptor," Blood, 2010, 116(7):1035-1044.

* cited by examiner

| Clone # | Signal Peptide | Tumor Targeting Domain | Hinge | Transmembrane Domain | Stimulatory Signal 1 | Stimulatory Signal 2 | Stimulatory Signal 3 |
|---|---|---|---|---|---|---|---|
| 2 | CD8a | hz39D2 | CD8a | CD8a | CD3z | | |
| 3 | CD8a | hz39D2 | CD8a | CD8a | 4-1BB | CD3z | |
| 6 | CD8a | hz39D2 | CD8a | CD8a | CD28 | CD3z | |
| 14 | CD8a | hz39D2 | CD8a | CD28 | CD28 | OX40L | CD3z |

FIG. 7

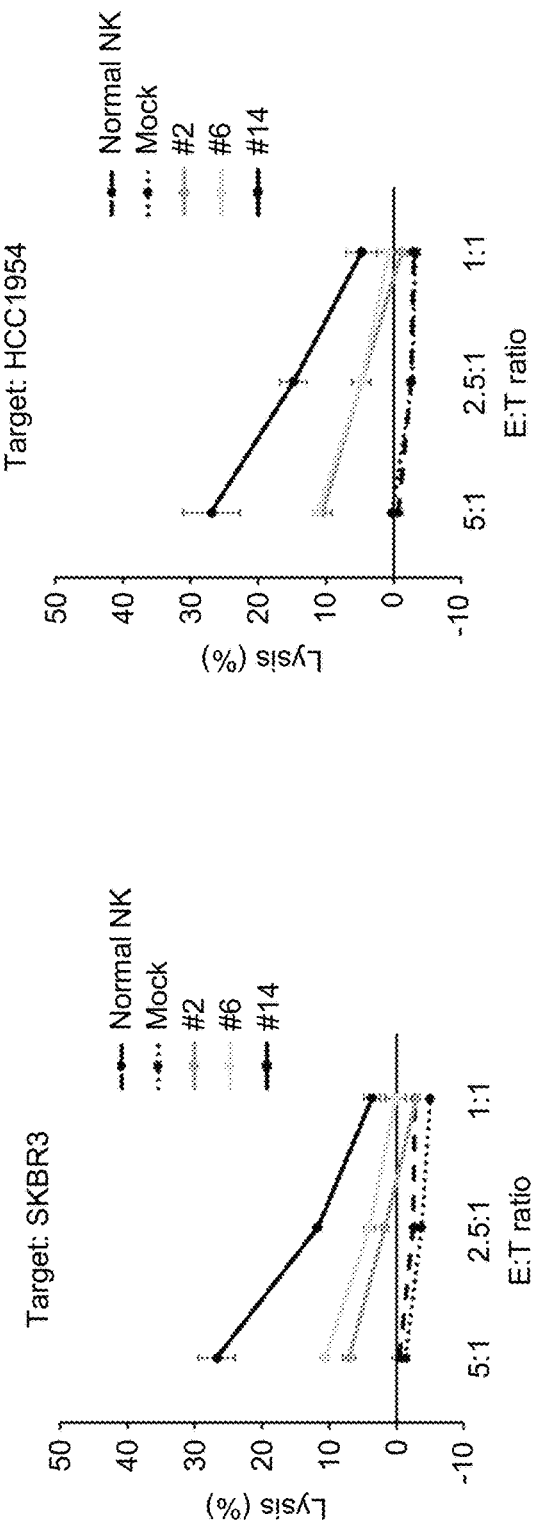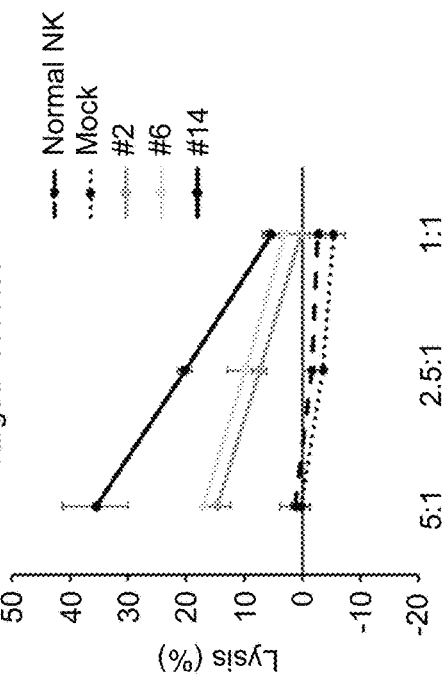
FIG. 8A
FIG. 8B
FIG. 8C

SEQUENCE LISTING

```
Sequence total quantity: 136
SEQ ID NO: 1          moltype = AA  length = 5
FEATURE               Location/Qualifiers
REGION                1..5
                      note = CDRH1 of hz2G10 antibody
source                1..5
                      mol_type = protein
                      organism = synthetic construct
SEQUENCE: 1
DYYMY                                                                  5

SEQ ID NO: 2          moltype = AA  length = 17
FEATURE               Location/Qualifiers
REGION                1..17
                      note = CDRH2 of hz2G10 antibody
source                1..17
                      mol_type = protein
                      organism = synthetic construct
SEQUENCE: 2
YINSGGGSTY YPDTVKG                                                     17
```

```
SEQ ID NO: 3            moltype = AA  length = 12
FEATURE                 Location/Qualifiers
REGION                  1..12
                        note = CDRH3 of hz2G10 antibody
source                  1..12
                        mol_type = protein
                        organism = synthetic construct
SEQUENCE: 3
EALYDYDYAM DY                                                              12

SEQ ID NO: 4            moltype = AA  length = 16
FEATURE                 Location/Qualifiers
REGION                  1..16
                        note = CDRL1 of hz2G10 antibody
source                  1..16
                        mol_type = protein
                        organism = synthetic construct
SEQUENCE: 4
KSSQSLLYSN GKTYLN                                                          16

SEQ ID NO: 5            moltype = AA  length = 7
FEATURE                 Location/Qualifiers
REGION                  1..7
                        note = CDRL2 of hz2G10 antibody
source                  1..7
                        mol_type = protein
                        organism = synthetic construct
SEQUENCE: 5
LVSKLDS                                                                     7

SEQ ID NO: 6            moltype = AA  length = 9
FEATURE                 Location/Qualifiers
REGION                  1..9
                        note = CDRL3 of hz2G10 antibody
source                  1..9
                        mol_type = protein
                        organism = synthetic construct
SEQUENCE: 6
VQGTHFPLT                                                                   9

SEQ ID NO: 7            moltype = AA  length = 5
FEATURE                 Location/Qualifiers
REGION                  1..5
                        note = CDRH1 of hz39D2 antibody
source                  1..5
                        mol_type = protein
                        organism = synthetic construct
SEQUENCE: 7
NYGVN                                                                       5

SEQ ID NO: 8            moltype = AA  length = 17
FEATURE                 Location/Qualifiers
REGION                  1..17
                        note = CDRH2 of hz39D2 antibody
source                  1..17
                        mol_type = protein
                        organism = synthetic construct
SEQUENCE: 8
WINTHTGEPT YAEEFKG                                                         17

SEQ ID NO: 9            moltype = AA  length = 9
FEATURE                 Location/Qualifiers
REGION                  1..9
                        note = CDRH3 of hz39D2 antibody
source                  1..9
                        mol_type = protein
                        organism = synthetic construct
SEQUENCE: 9
DDYYVRVDY                                                                   9

SEQ ID NO: 10           moltype = AA  length = 11
FEATURE                 Location/Qualifiers
REGION                  1..11
                        note = CDRL1 of hz39D2 antibody
source                  1..11
                        mol_type = protein
                        organism = synthetic construct
SEQUENCE: 10
```

```
KASQDINSYL S                                                                        11

SEQ ID NO: 11           moltype = AA   length = 7
FEATURE                 Location/Qualifiers
REGION                  1..7
                        note = CDRL2 of hz39D2 antibody
source                  1..7
                        mol_type = protein
                        organism = synthetic construct
SEQUENCE: 11
RANRLVD                                                                              7

SEQ ID NO: 12           moltype = AA   length = 9
FEATURE                 Location/Qualifiers
REGION                  1..9
                        note = CDRL3 of hz39D2 antibody
source                  1..9
                        mol_type = protein
                        organism = synthetic construct
SEQUENCE: 12
LQYDEFPWT                                                                            9

SEQ ID NO: 13           moltype = AA   length = 5
FEATURE                 Location/Qualifiers
REGION                  1..5
                        note = CDRH1 of 24D3 antibody
source                  1..5
                        mol_type = protein
                        organism = synthetic construct
SEQUENCE: 13
SCAMS                                                                                5

SEQ ID NO: 14           moltype = AA   length = 17
FEATURE                 Location/Qualifiers
REGION                  1..17
                        note = CDRH2 of 24D3 antibody
source                  1..17
                        mol_type = protein
                        organism = synthetic construct
SEQUENCE: 14
TISGGGSYTY YPDSVKG                                                                  17

SEQ ID NO: 15           moltype = AA   length = 10
FEATURE                 Location/Qualifiers
REGION                  1..10
                        note = CDRH3 of 24D3 antibody
source                  1..10
                        mol_type = protein
                        organism = synthetic construct
SEQUENCE: 15
HGGYESWFPY                                                                          10

SEQ ID NO: 16           moltype = AA   length = 16
FEATURE                 Location/Qualifiers
REGION                  1..16
                        note = CDRL1 of 24D3 antibody
source                  1..16
                        mol_type = protein
                        organism = synthetic construct
SEQUENCE: 16
RSSQSLVHSN GNTYLH                                                                   16

SEQ ID NO: 17           moltype = AA   length = 7
FEATURE                 Location/Qualifiers
REGION                  1..7
                        note = CDRL2 of 24D3 antibody
source                  1..7
                        mol_type = protein
                        organism = synthetic construct
SEQUENCE: 17
KVSNRFS                                                                              7

SEQ ID NO: 18           moltype = AA   length = 10
FEATURE                 Location/Qualifiers
REGION                  1..10
                        note = CDRL3 of 24D3 antibody
source                  1..10
                        mol_type = protein
                        organism = synthetic construct
```

```
SEQUENCE: 18
SQSTHVPPWT                                                                          10

SEQ ID NO: 19           moltype = AA   length = 5
FEATURE                 Location/Qualifiers
REGION                  1..5
                        note = CDRH1 of 1G3 antibody
source                  1..5
                        mol_type = protein
                        organism = synthetic construct
SEQUENCE: 19
DTYMH                                                                                5

SEQ ID NO: 20           moltype = AA   length = 17
FEATURE                 Location/Qualifiers
REGION                  1..17
                        note = CDRH2 of 1G3 antibody
source                  1..17
                        mol_type = protein
                        organism = synthetic construct
SEQUENCE: 20
RIDPANGYTR YDPNFQG                                                                  17

SEQ ID NO: 21           moltype = AA   length = 10
FEATURE                 Location/Qualifiers
REGION                  1..10
                        note = CDRH3 of 1G3 antibody
source                  1..10
                        mol_type = protein
                        organism = synthetic construct
SEQUENCE: 21
YYYGFYAMDY                                                                          10

SEQ ID NO: 22           moltype = AA   length = 11
FEATURE                 Location/Qualifiers
REGION                  1..11
                        note = CDRL1 of 1G3 antibody
source                  1..11
                        mol_type = protein
                        organism = synthetic construct
SEQUENCE: 22
KASQDVSTAV A                                                                        11

SEQ ID NO: 23           moltype = AA   length = 7
FEATURE                 Location/Qualifiers
REGION                  1..7
                        note = CDRL2 of 1G3 antibody
source                  1..7
                        mol_type = protein
                        organism = synthetic construct
SEQUENCE: 23
SASYRYT                                                                              7

SEQ ID NO: 24           moltype = AA   length = 9
FEATURE                 Location/Qualifiers
REGION                  1..9
                        note = CDRL3 of 1G3 antibody
source                  1..9
                        mol_type = protein
                        organism = synthetic construct
SEQUENCE: 24
QQHYSTPPT                                                                            9

SEQ ID NO: 25           moltype = AA   length = 5
FEATURE                 Location/Qualifiers
REGION                  1..5
                        note = CDRH1 of hz8G11 antibody
source                  1..5
                        mol_type = protein
                        organism = synthetic construct
SEQUENCE: 25
GYYMH                                                                                5

SEQ ID NO: 26           moltype = AA   length = 17
FEATURE                 Location/Qualifiers
REGION                  1..17
                        note = CDRH2 of hz8G11 antibody
source                  1..17
                        mol_type = protein
```

```
                         organism = synthetic construct
SEQUENCE: 26
HINPNNGGTS YNQKFKG                                                    17

SEQ ID NO: 27            moltype = AA   length = 6
FEATURE                  Location/Qualifiers
REGION                   1..6
                         note = CDRH3 of hz8G11 antibody
source                   1..6
                         mol_type = protein
                         organism = synthetic construct
SEQUENCE: 27
EEAFAY                                                                6

SEQ ID NO: 28            moltype = AA   length = 11
FEATURE                  Location/Qualifiers
REGION                   1..11
                         note = CDRL1 of hz8G11 antibody
source                   1..11
                         mol_type = protein
                         organism = synthetic construct
SEQUENCE: 28
RASQDISNYL N                                                          11

SEQ ID NO: 29            moltype = AA   length = 7
FEATURE                  Location/Qualifiers
REGION                   1..7
                         note = CDRL2 of hz8G11 antibody
source                   1..7
                         mol_type = protein
                         organism = synthetic construct
SEQUENCE: 29
YTSRLHS                                                               7

SEQ ID NO: 30            moltype = AA   length = 9
FEATURE                  Location/Qualifiers
REGION                   1..9
                         note = CDRL3 of hz8G11 antibody
source                   1..9
                         mol_type = protein
                         organism = synthetic construct
SEQUENCE: 30
QQGITPPWT                                                             9

SEQ ID NO: 31            moltype = AA   length = 121
FEATURE                  Location/Qualifiers
REGION                   1..121
                         note = Amino acid sequence of hz2G10 heavy chain variable
                          region
source                   1..121
                         mol_type = protein
                         organism = synthetic construct
SEQUENCE: 31
EVQLVESGGG LVQPGGSLRL SCAASGFTFS DYYMYWVRQA PGKGLEWVAY INSGGGSTYY      60
PDTVKGRFTI SRDNAKNSLY LQMNSLRAED TAVYYCAREA LYDYDYAMDY WGQGTTVTVS      120
S                                                                     121

SEQ ID NO: 32            moltype = DNA   length = 363
FEATURE                  Location/Qualifiers
misc_feature             1..363
                         note = Nucleic acid sequence of hz2G10 heavy chain variable
                          region
source                   1..363
                         mol_type = other DNA
                         organism = synthetic construct
SEQUENCE: 32
gaggtgcagt tggtcgagtc tggaggaggt ctggtacagc caggggggaag tctgagactg      60
agctgcgccg cttctggttt tacctttagc gattactata tgtattgggt aagacaggac      120
cctggtaaag gtttggaatg ggtggcctac ataaactcgg gcgggggcag cacctactac      180
ccggataccg tgaagggccg cttcaccatc tcccgagaca cgcgaaaaa ttcattgtat       240
ctgcaaatga actcacttag agctgaagat actgccgttt actactgcgc cagagaagca      300
ctctatgact atgattacgc tatggattac tgggggcagg gcacaaccgt cactgttcct      360
agt                                                                   363

SEQ ID NO: 33            moltype = AA   length = 451
FEATURE                  Location/Qualifiers
REGION                   1..451
                         note = Amino acid sequence of hz2G10 heavy chain
source                   1..451
```

```
                        mol_type = protein
                        organism = synthetic construct
SEQUENCE: 33
EVQLVESGGG  LVQPGGSLRL  SCAASGFTFS  DYYMYWVRQA  PGKGLEWVAY  INSGGGSTYY   60
PDTVKGRFTI  SRDNAKNSLY  LQMNSLRAED  TAVYYCAREA  LYDYDYAMDY  WGQGTTVTVS  120
SASTKGPSVF  PLAPSSKSTS  GGTAALGCLV  KDYFPEPVTV  SWNSGALTSG  VHTFPAVLQS  180
SGLYSLSSVV  TVPSSSLGTQ  TYICNVNHKP  SNTKVDKKVE  PKSCDKTHTC  PPCPAPELLG  240
GPSVFLFPPK  PKDTLMISRT  PEVTCVVVDV  SHEDPEVKFN  WYVDGVEVHN  AKTKPREEQY  300
NSTYRVVSVL  TVLHQDWLNG  KEYKCKVSNK  ALPAPIEKTI  SKAKGQPREP  QVYTLPPSRD  360
ELTKNQVSLT  CLVKGFYPSD  IAVEWESNGQ  PENNYKTTPP  VLDSDGSFFL  YSKLTVDKSR  420
WQQGNVFSCS  VMHEALHNHY  TQKSLSLSPG  K                                  451

SEQ ID NO: 34           moltype = DNA  length = 1353
FEATURE                 Location/Qualifiers
misc_feature            1..1353
                        note = Nucleic acid sequence of hz2G10 heavy chain
source                  1..1353
                        mol_type = other DNA
                        organism = synthetic construct
SEQUENCE: 34
gaggtgcagt tggtcgagtc tggaggaggt ctggtacagc caggggggaag tctgagactg   60
agctcgccg cttctggttt tacctttagc gattactata tgtattgggt aagacaggca  120
cctggtaaag gtttgaatg ggtgcctac ataaactcgg gcgggggcag cacctactac  180
ccggataccg tgaagggccg cttcaccatc tcccgagaca cgcgaaaaa ttcattgtat  240
ctgcaaatga actcacttag agctgaagat actgccgttt actactgcgc cagagaagca  300
ctctatgact atgattacgc tatggattac tgggggcagg gcacaaccgt cactgtttct  360
agtgcctcca ccaagggccc ctccgtgttc cctctggccc cctccagcaa gtccacctct  420
ggcggcacag ccgccctggg ctgcctggtg aaagactact tccccgagcc cgtgaccgtg  480
tcctggaact ctggcgccct gacctccggc gtgcacacct ccctgccgt gctgcagtcc  540
tccggcctgt actccctgtc ctccgtggtg accgtgccca gctctctg gggcacccag  600
acctacatct gtaacgtgaa ccacaagccc tccaacacca aggtggacaa gaaggtggaa  660
cccaagtcct gcgacaagac ccacacctgt ccccctgcc ctgccctga actgctgggc  720
ggaccttccg tgttcctgtt ccccccaaag cccaaggaca cctgatgat ctcccggacc  780
cccgaagtga cctgcgtggt ggtggacgtg tcccgcgagg accctgaagt gaagttcaat  840
tggtacgtgg acggcgtgga agtgcacaat gccaagacca agcccagaga ggaacagtac  900
aactccacct accgggtggt gtctgtgctg accgtgctgc accaggactg gctgaacggc  960
aaagaataca agtgcaaagt ctccaacaag gcctgcctg cccccatcga aaagaccatc 1020
tccaaggcca agggccagcc ccgcgagccc caggtgtaca cctgcccc tagccgggac 1080
gagctgacca gaaccaggt gtccctgacc tgtctggtga aaggcttcta ccctcccgac 1140
attgccgtgg aatgggagtc caacggccag cccgagaaca actacaagac cacccccct 1200
gtgctggact ccgacggctc attcttcctg tactccaagc tgaccgtgga caagtcccgg 1260
tggcagcagg gcaacgtgtt ctcctgctcc gtgatgcacg aggccctgca caaccactac 1320
acccagaagt ccctgtccct gagccccggc aag                              1353

SEQ ID NO: 35           moltype = AA  length = 112
FEATURE                 Location/Qualifiers
REGION                  1..112
                        note = Amino acid sequence of hz2G10 light chain variable
                        region
source                  1..112
                        mol_type = protein
                        organism = synthetic construct
SEQUENCE: 35
DIVMTQSPLS  LSVTPGQPAS  ISCKSSQSLL  YSNGKTYLNW  LLQKPGQSPQ  RLIYLVSKLD   60
SGVPDRFSGS  GSGTDFTLKI  SRVEAEDVGV  YYCVQGTHFP  LTFGGGTKVE  IK          112

SEQ ID NO: 36           moltype = DNA  length = 336
FEATURE                 Location/Qualifiers
misc_feature            1..336
                        note = Nucleic acid sequence of hz2G10 light chain variable
                        region
source                  1..336
                        mol_type = other DNA
                        organism = synthetic construct
SEQUENCE: 36
gacattgtca tgacgcagag ccccctttca ctcagcgtga ctcccggtca gcccgccagc   60
atttcctgta aaagctctca gtcgctcctg tacagcaatg gcaagactta tctgaattgg  120
ctgttacaga aaccaggcca aagccctcaa aggcttatct acctggtgag taagttagac  180
agcggggtgc ctgacagatt tagcggatct ggaagcgggac ccgatttcac actaaaaatc  240
agcagggttg aggcagagga cgtgggcgtg tattattgtg tgcagggcac acacttccca  300
ctcacattcg ggggaggcac aaaggtggaa atcaag                            336

SEQ ID NO: 37           moltype = AA  length = 219
FEATURE                 Location/Qualifiers
REGION                  1..219
                        note = Amino acid sequence of hz2G10 light chain
source                  1..219
                        mol_type = protein
                        organism = synthetic construct
```

```
SEQUENCE: 37
DIVMTQSPLS LSVTPGQPAS ISCKSSQSLL YSNGKTYLNW LLQKPGQSPQ RLIYLVSKLD    60
SGVPDRFSGS GSGTDFTLKI SRVEAEDVGV YYCVQGTHFP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 38           moltype = DNA   length = 657
FEATURE                 Location/Qualifiers
misc_feature            1..657
                        note = Nucleic acid sequence of hz2G10 light chain
source                  1..657
                        mol_type = other DNA
                        organism = synthetic construct
SEQUENCE: 38
gacattgtca tgacgcagag ccccctttca ctcagcgtga ctcccggtca gcccgccagc    60
atttcctgta aaagctctca gtcgctcctg tacagcaatg gcaagactta tctgaattgg   120
ctgttacaga accaggccaa gccctcaa ag gcttatct acctggtgag taagttagac     180
agcggggtgc ctgacagatt tagcggatct ggaagcggaa ccgatttcac actaaaaatc   240
agcagggttg aggcagagga cgtgggcgtg tattattgtg tgcagggcac acacttccca   300
ctcacattcg gggaggcac aaaggtggaa atcaagcgga ccgtggccgc tcctccgtg     360
ttcatcttcc caccctccga cgagcagctg aagtccggaa ccgccagcgt ggtctgcctg   420
ctgaacaact tctaccccccg cgaggccaag gtgcagtgaa agtggacaa cgccctgcag   480
tccggcaact cccaggaatc cgtcaccgag caggactgca aggacagcac ctactccctg   540
tcctccaccc tgaccctgtc caaggccgac tacgagaagc acaaggtgta cgcctgcgaa   600
gtgacccacc agggcctgtc cagccccgtg accaagtcct tcaaccgggg cgagtgc     657

SEQ ID NO: 39           moltype = AA    length = 118
FEATURE                 Location/Qualifiers
REGION                  1..118
                        note = Amino acid sequence of hz39D2 heavy chain variable
                         region
source                  1..118
                        mol_type = protein
                        organism = synthetic construct
SEQUENCE: 39
QVQLVQSGSE LKKPGASVKV SCKASGYTFT NYGVNWVRQA PGQGLEWMGW INTHTGEPTY    60
AEEFKGRFVF SLDTSVSTAY LQISSLKAED TAVYYCARDD YYVRVDYWGQ GTTVTVSS    118

SEQ ID NO: 40           moltype = DNA   length = 354
FEATURE                 Location/Qualifiers
misc_feature            1..354
                        note = Nucleic acid sequence of hz39D2 heavy chain variable
                         region
source                  1..354
                        mol_type = other DNA
                        organism = synthetic construct
SEQUENCE: 40
caagtccaac tcgtgcagtc aggatctgaa ctgaagaaac ctggagcgag cgttaaggtt    60
tcctgcaagg ccagcggcta acgttcact aactatggtg tcaactgggt gagacaggca   120
cccgccagg gcctggagtg gatgggttgg atcaatactc acacagggga accaacatat   180
gctgaggagt tcaaaggacg gtttgttttt agtctgagca cctccgtgtc taccgcctac   240
ctgcagattt ccagccttaa agcagaggac actgctgtat actactgtgc cagagacgat   300
tactatgtga gggtcgatta ctgggggcag gggaccaccg tgacagtctc aagt         354

SEQ ID NO: 41           moltype = AA    length = 448
FEATURE                 Location/Qualifiers
REGION                  1..448
                        note = Amino acid sequence of hz39D2 heavy chain
source                  1..448
                        mol_type = protein
                        organism = synthetic construct
SEQUENCE: 41
QVQLVQSGSE LKKPGASVKV SCKASGYTFT NYGVNWVRQA PGQGLEWMGW INTHTGEPTY    60
AEEFKGRFVF SLDTSVSTAY LQISSLKAED TAVYYCARDD YYVRVDYWGQ GTTVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                      448

SEQ ID NO: 42           moltype = DNA   length = 1344
FEATURE                 Location/Qualifiers
misc_feature            1..1344
                        note = Nucleic acid sequence of hz39D2 heavy chain
source                  1..1344
                        mol_type = other DNA
                        organism = synthetic construct
SEQUENCE: 42
```

```
caagtccaac tcgtgcagtc aggatctgaa ctgaagaaac ctggagcgag cgttaaggtt    60
tcctgcaagg ccagcggcta tacgttcact aactatggtg tcaactgggt gagacaggca   120
cccggccagg gcctggagtg gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgat   300
tactatgtga gggtggatta ctgggggcag gggaccaccg tgacagtctc aagtgcctcc   360
accaagggcc cctccgtgtt ccctctggcc cctccagca agtccacctc tggcggcaca   420
gccgccctgg gctgcctggt gaaagactac ttccccgagc ccgtgaccgt gtcctggaac   480
tctgcgcc tgacctccgg cgtgcacacc ttccctgccg tgctgcagtc ctccggcctg    540
tactccctgt cctccgtggt gaccgtgccc tccagctctc tgggcaccca gacctacatc   600
tgtaacgtga accacaagcc ctccaacacc aaggtggaca gaaggtggaa cccaagtcc    660
tgcgacaaga cccacacctg tcccccctgc cctgcccctg aactgctggg cggaccttcc   720
gtgttcctgt tccccccaaa gcccaaggac accctgatga tctcccggac cccgaagtg    780
acctggcgtg tggtggacgt gtcccacgag gaccctgaag tgaagttcaa ttggtacgtg   840
gacggcgtgg aagtgcacaa tgccaagacc aagcccagag aggaacagta caactgcacc   900
tacccgggtgg tgtctgtgct gaccgtgctg caccaggact ggctgaacgg caagaatac   960
aagtgcaaag tctccaacaa ggccctgcct gcccccatcg aaaagaccat ctccaaggcc  1020
aagggccagc cccgcgagcc ccagggtac accctgcccc ctagccggga cgagctgacc   1080
aagaaccagg tgtccctgac ctgtctggtg aaaggcttct accctccga cattgccgtg  1140
gaatgggagt ccaacggcca gcccgagaac aactacaaga ccaccccccc tgtgctggac   1200
tccgacggct cattcttcct gtactccaag ctgaccgtgg acaagtcccg gtggcagcag   1260
gcaacgtgt tctcctgctc cgtgatgcac gaggccctgc acaaccacta cacccagaag   1320
tccctgtccc tgagccccgg caag                                         1344

SEQ ID NO: 43            moltype = AA  length = 107
FEATURE                  Location/Qualifiers
REGION                   1..107
                         note = Amino acid sequence of hz39D2 light chain variable
                         region
source                   1..107
                         mol_type = protein
                         organism = synthetic construct
SEQUENCE: 43
DIQMTQSPSS LSASVGDRVT ITCKASQDIN SYLSWFQQKP GKAPKTLIYR ANRLVDGVPS    60
RFSGSGSGQD YTLTISSLQP EDFATYYCLQ YDEFPWTFGQ GTKVEIK                107

SEQ ID NO: 44            moltype = DNA  length = 321
FEATURE                  Location/Qualifiers
misc_feature             1..321
                         note = Nucleic acid sequence of hz39D2 light chain variable
                         region
source                   1..321
                         mol_type = other DNA
                         organism = synthetic construct
SEQUENCE: 44
gacattcaaa tgacacagtc tcccagctcc cttagtgctt cggtgggcga tcgggtgacc    60
ataacatgca aggcctcaca ggacatcaac agctatctct catggtttca gcagaagcca   120
ggaaaagcac ctaaaacgtt gatctacagg gccaatcgcc tcgttgacgg agtcccctcc   180
agattcagcg ggagtgggtc tggtcaggat tatactctga ccatctcctc tctgcagcct   240
gaagactttg ccacttacta ctgtctgcaa tacgatgagt tcccatggac cttcggccag   300
ggcaccaagg tggagattaa a                                             321

SEQ ID NO: 45            moltype = AA  length = 214
FEATURE                  Location/Qualifiers
REGION                   1..214
                         note = Amino acid sequence of hz39D2 light chain
source                   1..214
                         mol_type = protein
                         organism = synthetic construct
SEQUENCE: 45
DIQMTQSPSS LSASVGDRVT ITCKASQDIN SYLSWFQQKP GKAPKTLIYR ANRLVDGVPS    60
RFSGSGSGQD YTLTISSLQP EDFATYYCLQ YDEFPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 46            moltype = DNA  length = 642
FEATURE                  Location/Qualifiers
misc_feature             1..642
                         note = Nucleic acid sequence of hz39D2 light chain
source                   1..642
                         mol_type = other DNA
                         organism = synthetic construct
SEQUENCE: 46
gacattcaaa tgacacagtc tcccagctcc cttagtgctt cggtgggcga tcgggtgacc    60
ataacatgca aggcctcaca ggacatcaac agctatctct catggtttca gcagaagcca   120
ggaaaagcac ctaaaacgtt gatctacagg gccaatcgcc tcgttgacgg agtcccctcc   180
agattcagcg ggagtgggtc tggtcaggat tatactctga ccatctcctc tctgcagcct   240
gaagactttg ccacttacta ctgtctgcaa tacgatgagt tcccatggac cttcggccag   300
ggcaccaagg tggagattaa acggaccgtg gccgctccct ccgtgttcat cttcccaccc   360
```

```
tccgacgagc agctgaagtc cggcaccgcc agcgtggtct gcctgctgaa caacttctac    420
ccccgcgagg ccaaggtgca gtggaaggtg gacaacgccc tgcagtccgg caactcccag    480
gaatccgtca ccgagcagga ctccaaggac agcacctact ccctgtcctc caccctgacc    540
ctgtccaagg ccgactacga gaagcacaag gtgtacgcct gcgaagtgac ccaccagggc    600
ctgtccagcc ccgtgaccaa gtccttcaac cggggcgagt gc                       642

SEQ ID NO: 47           moltype = AA   length = 119
FEATURE                 Location/Qualifiers
REGION                  1..119
                        note = Amino acid sequence of 24D3 heavy chain variable
                        region
source                  1..119
                        mol_type = protein
                        organism = synthetic construct
SEQUENCE: 47
EVKLVESGGG LVKPGGSLKL SCAASGFTFS SCAMSWVRQT PEKRLEWVAT ISGGGSYTYY    60
PDSVKGRFTI SRDNAKNTLY LQMSSLRSED TAMYYCARHG GYESWFPYWG QGTLVTVSA    119

SEQ ID NO: 48           moltype = DNA   length = 357
FEATURE                 Location/Qualifiers
misc_feature            1..357
                        note = Nucleic acid sequence of 24D3 heavy chain variable
                        region
source                  1..357
                        mol_type = other DNA
                        organism = synthetic construct
SEQUENCE: 48
gaggtgaagc tggtggagtc tgggggaggc ttagtgaagc ctggagggtc cctgaaactc    60
tcctgtgcag cctctggatt cactttcagt agctgtgcca tgtcttgggt ccgccagact    120
ccggagaaga ggctggagtg ggtcgcaacc attagtgggg gtggtagtta cacctactat    180
ccagacagtg tgaaggggcg attcaccatc tccagagaca atgccaagaa caccctgtac    240
ctgcaaatga gcagtctgag gtctgaggac acggccatgt attactgtgc aagacatggc    300
gggtacgagt cctggtttcc ttactgggggc caagggactc tggtcactgt ctctgca     357

SEQ ID NO: 49           moltype = AA   length = 449
FEATURE                 Location/Qualifiers
REGION                  1..449
                        note = Amino acid sequence of 24D3 heavy chain
source                  1..449
                        mol_type = protein
                        organism = synthetic construct
SEQUENCE: 49
EVKLVESGGG LVKPGGSLKL SCAASGFTFS SCAMSWVRQT PEKRLEWVAT ISGGGSYTYY    60
PDSVKGRFTI SRDNAKNTLY LQMSSLRSED TAMYYCARHG GYESWFPYWG QGTLVTVSAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 50           moltype = DNA   length = 1347
FEATURE                 Location/Qualifiers
misc_feature            1..1347
                        note = Nucleic acid sequence of 24D3 heavy chain
source                  1..1347
                        mol_type = other DNA
                        organism = synthetic construct
SEQUENCE: 50
gaggtgaagc tggtggagtc tgggggaggc ttagtgaagc ctggagggtc cctgaaactc    60
tcctgtgcag cctctggatt cactttcagt agctgtgcca tgtcttgggt ccgccagact    120
ccggagaaga ggctggagtg ggtcgcaacc attagtgggg gtggtagtta cacctactat    180
ccagacagtg tgaaggggcg attcaccatc tccagagaca atgccaagaa caccctgtac    240
ctgcaaatga gcagtctgag gtctgaggac acggccatgt attactgtgc aagacatggc    300
gggtacgagt cctggtttcc ttactgggggc caagggactc tggtcactgt ctctgcagcc    360
tccaccaagg gcccctccgt gttccctctg gccccctcca gcaagtccac ctctggcggc    420
acagccgccc tgggctgcct ggtgaaagac tacttccccg agcccgtgac cgtgtcctgg    480
aactctggcg ccctgaccct cggcgtgcac accttccctg ccgtgctgca gtcctccggc    540
ctgtactccc tgtcctccgt ggtgaccgtg ccctccagca gtctgggcac ccagacctac    600
atctgtaacg tgaaccacaa gcctccaac accaaggtgg acaagaaggt ggaacccaag    660
tcctgcgaca gaccacacac ctgtcccccc tgccctgccc ctgaactgct gggcggacct    720
tccgtgttcc tgttcccccc aaagcccaag gacaccctga tgatctcccg acccccgaa    780
gtgacctgcg tggtggtgga cgtgtccac gaggaccctg aagtgaagtt caattggtac    840
gtggacggcg tggaagtgca caatgccaag accaagccac gagaggaaca gtacaactcc    900
acctaccggg tggtgtctgt gctgaccgtg ctgcaccagg actggctgaa cggcaaagaa    960
tacaagtgca agtctccaa caaggccctg cctgccccca tcgaaaagac catctccaag    1020
gccaagggcc agccccgcga gccccaggtg tacaccctgc ccctagccg ggacgagctg    1080
accaagaacc aggtgtccct gacctgtctg gtgaaaggct ctaccccctc cgacattgcc    1140
gtggaatggg agtccaacgg ccagcccgag aacaactaca gaccacccc cctgtgctg    1200
```

```
gactccgacg gctcattctt cctgtactcc aagctgaccg tggacaagtc ccggtggcag   1260
cagggcaacg tgttctcctg ctccgtgatg cacgaggccc tgcacaacca ctacacccag   1320
aagtccctgt ccctgagccc cggcaag                                      1347

SEQ ID NO: 51            moltype = AA   length = 113
FEATURE                  Location/Qualifiers
REGION                   1..113
                         note = Amino acid sequence of 24D3 light chain variable
                          region
source                   1..113
                         mol_type = protein
                         organism = synthetic construct
SEQUENCE: 51
DIVMTQSPLS LPVSLGDQAS ISCRSSQSLV HSNGNTYLHW YLQKPGQSPK LLIYKVSNRF    60
SGVPDRFSGS GSGTDFTLKI SRVEAEDLGV YFCSQSTHVP PWTFGGGTKL EIK          113

SEQ ID NO: 52            moltype = DNA   length = 339
FEATURE                  Location/Qualifiers
misc_feature             1..339
                         note = Nucleic acid sequence of 24D3 light chain variable
                          region
source                   1..339
                         mol_type = other DNA
                         organism = synthetic construct
SEQUENCE: 52
gatattgtga tgacccagtc tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggttc cagacaggtt cagtggcagt ggatcaggga cagatttcac actcaagatc   240
agcagagtgg aggctgagga tctgggagtt tatttctgct ctcaaagtac acatgttcct   300
ccgtggacgt tcggtggagg gaccaagctg gaaatcaaa                          339

SEQ ID NO: 53            moltype = AA   length = 220
FEATURE                  Location/Qualifiers
REGION                   1..220
                         note = Amino acid sequence of 24D3 light chain
source                   1..220
                         mol_type = protein
                         organism = synthetic construct
SEQUENCE: 53
DIVMTQSPLS LPVSLGDQAS ISCRSSQSLV HSNGNTYLHW YLQKPGQSPK LLIYKVSNRF    60
SGVPDRFSGS GSGTDFTLKI SRVEAEDLGV YFCSQSTHVP PWTFGGGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 54            moltype = DNA   length = 660
FEATURE                  Location/Qualifiers
misc_feature             1..660
                         note = Nucleic acid sequence of 24D3 light chain
source                   1..660
                         mol_type = other DNA
                         organism = synthetic construct
SEQUENCE: 54
gatattgtga tgacccagtc tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggttc cagacaggtt cagtggcagt ggatcaggga cagatttcac actcaagatc   240
agcagagtgg aggctgagga tctgggagtt tatttctgct ctcaaagtac acatgttcct   300
ccgtggacgt tcggtggagg gaccaagctg gaaatcaaac ggaccgtggc cgctcccagc   360
gtgttcatct tccccccctc cgacgagcag ctgaagtccg gcaccgccag cgtggtctgc   420
ctgctgaaca acttctaccc ccgcgaggcc aaggtgcagt ggaaggtgga caacgccctg   480
cagtccggca actcccagga atccgtcacc gagcaggact ccaaggacag cacctactcc   540
ctgtcctcca ccctgaccct gtccaaggcc gactacgaga gcacaaggt gtacgcctgc    600
gaagtgaccc accagggcct gtccagcccc gtgaccaagt ccttcaaccg ggccgagtgc   660

SEQ ID NO: 55            moltype = AA   length = 119
FEATURE                  Location/Qualifiers
REGION                   1..119
                         note = Amino acid sequence of 1G3 heavy chain variable
                          region
source                   1..119
                         mol_type = protein
                         organism = synthetic construct
SEQUENCE: 55
EVQLQQSGAE LVKPGASVKL SCTASDFNIV DTYMHWVKQR PEQGLEWIGR IDPANGYTRY    60
DPNFQGKATI TADTSSNTAY LQLSSLTSED TAVYYCARYY YGFYAMDYWG QGTTVTVSS    119

SEQ ID NO: 56            moltype = DNA   length = 357
FEATURE                  Location/Qualifiers
```

| | |
|---|---|
| misc_feature | 1..357 |
| | note = Nucleic acid sequence of 1G3 heavy chain variable region |
| source | 1..357 |
| | mol_type = other DNA |
| | organism = synthetic construct |

SEQUENCE: 56
```
gaggttcagc tgcagcagtc tggggcagag cttgtgaagc caggggcctc agtcaagttg    60
tcctgcacag cttctgactt caacattgta gacacctata tgcactgggt gaagcagagg   120
cctgaacagg gcctggagtg gattggaagg attgatcctg cgaatggtta tactagatat   180
gacccgaact tccagggcaa ggccactata acagcagaca catcctccaa cacagcctac   240
ctgcagctca gcagcctgac atctgaggac actgccgtct attactgtgc ccgttattac   300
tacggcttct atgctatgga ctactgggt caaggaacca cggtcaccgt ctcctca      357
```

| | |
|---|---|
| SEQ ID NO: 57 | moltype = AA length = 449 |
| FEATURE | Location/Qualifiers |
| REGION | 1..449 |
| | note = Amino acid sequence of 1G3 heavy chain |
| source | 1..449 |
| | mol_type = protein |
| | organism = synthetic construct |

SEQUENCE: 57
```
EVQLQQSGAE LVKPGASVKL SCTASDFNIV DTYMHWVKQR PEQGLEWIGR IDPANGYTRY    60
DPNFQGKATI TADTSSNTAY LQLSSLTSED TAVYYCARYY YGFYAMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449
```

| | |
|---|---|
| SEQ ID NO: 58 | moltype = DNA length = 1347 |
| FEATURE | Location/Qualifiers |
| misc_feature | 1..1347 |
| | note = Nucleic acid sequence of 1G3 heavy chain |
| source | 1..1347 |
| | mol_type = other DNA |
| | organism = synthetic construct |

SEQUENCE: 58
```
gaggttcagc tgcagcagtc tggggcagag cttgtgaagc caggggcctc agtcaagttg    60
tcctgcacag cttctgactt caacattgta gacacctata tgcactgggt gaagcagagg   120
cctgaacagg gcctggagtg gattggaagg attgatcctg cgaatggtta tactagatat   180
gacccgaact tccagggcaa ggccactata acagcagaca catcctccaa cacagcctac   240
ctgcagctca gcagcctgac atctgaggac actgccgtct attactgtgc ccgttattac   300
tacggcttct atgctatgga ctactgggt caaggaacca cggtcaccgt ctcctcagcc   360
tccaccaagg gcccctccgt gttccctctg gcccctcca gcaagtccac ctctggcggc   420
acagcggccc tgggctgcct ggtgaaagac tacttcccga gcccgtgtcctg          480
aactctggcg ccctgacctc cggcgtgcac accttccctg ccgtgctgca gtcctccggc   540
ctgtactccc tgtcctccgt ggtgaccgtg ccctccagct ctctgggcac ccagacctac   600
atctgtaacg tgaaccacaa gcctccaac accaaggtgg acaagaaggt ggaacccaag   660
tcctgcgaca gacccacac ctgtccccc tgccctgcc ctgaactgct gggcggaccct   720
tccgtgttcc tgttccccc aaagccaag gacaccctga tcatccgg gacccgaa        780
gtgacctgcg tggtggtgga cgtgtcccac gaggaccctg aagtgaagtt caattggtac   840
gtggacggcg tggaagtgca caatgccaag accaagccca gaggaaaca gtacaactcc   900
acctacgg tggtgtctgt gctgaccgtg ctgcaccagg actggctgaa cggcaaagaa     960
tacaagtgca agtctccaa caaggccctg cctgccccca tcgaaaagac catctccaag   1020
gccagggcc agccccgcga gccccaggtg tacaccctgc ccctagccg ggacgagctg   1080
accaagaacc aggtgtccct gacctgtctg gtgaaaggct ctaccccctc gacattgcc   1140
gtggaatggg agtccaacgg ccagcccgag aacaactaca agaccacccc cctgtgctg   1200
gactccgacg gctccttctt cctgtactcc aagctgaccg tggacaagtc ccggtggcag   1260
cagggcaacg tgttctcctg ctccgtgatg cacgaggccc tgcacaacca ctacacccag   1320
aagtccctgt ccctgagccc cggcaag                                     1347
```

| | |
|---|---|
| SEQ ID NO: 59 | moltype = AA length = 107 |
| FEATURE | Location/Qualifiers |
| REGION | 1..107 |
| | note = Amino acid sequence of 1G3 light chain variable region |
| source | 1..107 |
| | mol_type = protein |
| | organism = synthetic construct |

SEQUENCE: 59
```
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPPTFGG GTKLELK                107
```

| | |
|---|---|
| SEQ ID NO: 60 | moltype = DNA length = 321 |
| FEATURE | Location/Qualifiers |
| misc_feature | 1..321 |
| | note = Nucleic acid sequence of 1G3 light chain variable |

```
                           region
source                     1..321
                           mol_type = other DNA
                           organism = synthetic construct
SEQUENCE: 60
gatattgtga tgacgcagtc tcacaaattc atgtccacat cagtaggaga cagggtcagc   60
atcacctgca aggccagtca ggatgtgagt actgctgtag cctggtatca acagaaacca  120
ggacaatctc ctaaactact gatttactcg gcatcctacc ggtacactgg agtccctgat  180
cgcttcactg gcagtggatc tgggacggat ttcactttca ccatcagcag tgtgcaggct  240
gaagacctgg cagtttatta ctgtcagcaa cattatagta ctcctcccac gttcggaggg  300
gggaccaagc tggagctgaa a                                            321

SEQ ID NO: 61              moltype = AA  length = 214
FEATURE                    Location/Qualifiers
REGION                     1..214
                           note = Amino acid sequence of 1G3 light chain
source                     1..214
                           mol_type = protein
                           organism = synthetic construct
SEQUENCE: 61
DIVMTQSHKF MSTSVGDRVS ITCKASQDVS TAVAWYQQKP GQSPKLLIYS ASYRYTGVPD   60
RFTGSGSGTD FTFTISSVQA EDLAVYYCQQ HYSTPPTFGG GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 62              moltype = DNA  length = 642
FEATURE                    Location/Qualifiers
misc_feature               1..642
                           note = Nucleic acid sequence of 1G3 light chain
source                     1..642
                           mol_type = other DNA
                           organism = synthetic construct
SEQUENCE: 62
gatattgtga tgacgcagtc tcacaaattc atgtccacat cagtaggaga cagggtcagc   60
atcacctgca aggccagtca ggatgtgagt actgctgtag cctggtatca acagaaacca  120
ggacaatctc ctaaactact gatttactcg gcatcctacc ggtacactgg agtccctgat  180
cgcttcactg gcagtggatc tgggacggat ttcactttca ccatcagcag tgtgcaggct  240
gaagacctgg cagtttatta ctgtcagcaa cattatagta ctcctcccac gttcggaggg  300
gggaccaagc tggagctgaa acggaccgtg gccgctccct ccgtgttcat cttcccaccc  360
tccgacgagc agctgaagtc cggcaccgcc agcgtggtct gcctgctgaa caacttctac  420
ccccgcgagg ccaaggtgca gtggaaggtg gacaacgccc tgcagtccgg caactcccag  480
gaatccgtca ccgagcagga ctccaaggac agcacctact ccctgtcctc cacccctgacc  540
ctgtccaagg ccgactacga aaagcacaag gtgtacgcct gcgaagtgac ccaccagggc  600
ctgtccagcc ccgtgaccaa gtccttcaac cggggcgagt gc                     642

SEQ ID NO: 63              moltype = AA  length = 115
FEATURE                    Location/Qualifiers
REGION                     1..115
                           note = Amino acid sequence of hz8G11 heavy chain variable
                                region
source                     1..115
                           mol_type = protein
                           organism = synthetic construct
SEQUENCE: 63
QVQLVQSGQE VKKPGASVKV SCKASGYSFT GYYMHWVRQA PGQGLEWIGH INPNNGGTSY   60
NQKFKGRTTL TVDKSISTAY MELSRLRSDD TAVYYCAREE AFAYWGQGTL VTVSS       115

SEQ ID NO: 64              moltype = DNA  length = 345
FEATURE                    Location/Qualifiers
misc_feature               1..345
                           note = Nucleic acid sequence of hz8G11 heavy chain variable
                                region
source                     1..345
                           mol_type = other DNA
                           organism = synthetic construct
SEQUENCE: 64
caggtacagc tagtgcagag cggccaggaa gtaaagaagc caggcgcctc tgttaaggtg   60
tcatgtaagg ccagcggtta cagcttcact ggctattaca tgcactgggt ccggcaggca  120
cccggacaag ggctggaatg gataggtcac attaatccaa acaatggcgg taccagttat  180
aaccagaaat ttaaggggag gacaacccctg acagttgata aatccatcag tacagcatat  240
atggagctca gcagactgag aagcgacgat actgctgtgt actactgcgc gcgggaggag  300
gctttcgcct actggggcca aggaccttta gtgactgtct catca                  345

SEQ ID NO: 65              moltype = AA  length = 445
FEATURE                    Location/Qualifiers
REGION                     1..445
                           note = Amino acid sequence of hz8G11 heavy chain
source                     1..445
                           mol_type = protein
```

-continued

```
                              organism = synthetic construct
SEQUENCE: 65
QVQLVQSGQE VKKPGASVKV SCKASGYSFT GYYMHWVRQA PGQGLEWIGH INPNNGGTSY    60
NQKFKGRTTL TVDKSISTAY MELSRLRSDD TAVYYCAREE AFAYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGK                                        445

SEQ ID NO: 66              moltype = DNA   length = 1335
FEATURE                    Location/Qualifiers
misc_feature               1..1335
                           note = Nucleic acid sequence of hz8G11 heavy chain
source                     1..1335
                           mol_type = other DNA
                           organism = synthetic construct
SEQUENCE: 66
caggtacagc tagtgcagag cggccaggaa gtaaagaagc caggcgcctc tgttaaggtg     60
tcatgtaagg ccagcggtta cagcttcact ggctattaca tgcactgggt ccggcaggca   120
cccggacaag ggctggaatg gataggtcac attaatccaa acaatggcgg taccagttat   180
aaccagaaat ttaaggggag acaaccctg acagttgata atccatcag tacagcatat     240
atggagctca gcagactgag aagcgacgat actgctgtgt actactgcgc gcggaggag    300
gctttcgcct actgggcca aggaccttta gtgactgtct catcagcctc caccaagggc    360
ccctccgtgt tccctctggc ccctccagc aagtccacct ctggcggcac agccgccctg    420
ggctgcctgg tgaaagacta cttccccgag cccgtgaccg tgtcctggaa ctctggcgcc    480
ctgacctccg gcgtgcacac cttccctgcc gtgctgcagt cctccggcct gtactccctg    540
tcctccgtgg tgaccgtgcc ctccagctct ctgggcaccc agacctacat ctgtaacgtg    600
aaccacaagc cctccaacac caaggtggac aagaaggtg aacccaagtc ctgcgacaag    660
acccacacct gtccccctg ccctgccct gaactgctgg gcggaccttc cgtgttcctg     720
ttccccccaa agcccaagga caccctgatg atctccgga ccccgaagt gacctgcgtg     780
gtggtggacg tgtcccacga ggaccctgaa gtgaagttca attggtacgt ggacggcgtg   840
gaagtgcaca atgccaagac caagcccaga gaggaacagt acaactccac ctaccgggtg   900
gtgtctgtgc tgaccgtgct gcaccaggac tggctgaacg gcaaagaata caagtgcaaa   960
gtctccaaca aggccctgcc tgcccccatc gaaaagacca tctccaaggc caagggccag  1020
ccccgcgagc cccaggtgta cacctgcc cctagccggg acgagctgac caagaaccag    1080
gtgtccctga cctgtctggt gaaggcttc taccctccg acattgccgt ggaatgggag    1140
tccaacggc agcccgagaa caactacaag accccccc ctgtgctgga ctccgacggc     1200
tcattcttcc tgtactccaa gctgaccgtg gacaagccc ggtggcagca gggcaacgtg    1260
ttctcctgct ccgtgatgca cgaggccctg cacaaccact acacccagaa gtccctgtcc  1320
ctgagccccg gcaag                                                   1335

SEQ ID NO: 67              moltype = AA   length = 107
FEATURE                    Location/Qualifiers
REGION                     1..107
                           note = Amino acid sequence of hz8G11 light chain variable
                            region
source                     1..107
                           mol_type = protein
                           organism = synthetic construct
SEQUENCE: 67
DIQMTQSPSS LSASVGDRVT ISCRASQDIS NYLNWYQQKP GKAPKLLIYY TSRLHSGVPS    60
RFSGSGSGTD FSLTISSLQP EDIATYYCQQ GITPPWTFGG GTKVEIK                 107

SEQ ID NO: 68              moltype = DNA   length = 321
FEATURE                    Location/Qualifiers
misc_feature               1..321
                           note = Nucleic acid sequence of hz8G11 light chain variable
                            region
source                     1..321
                           mol_type = other DNA
                           organism = synthetic construct
SEQUENCE: 68
gacatacaga tgacgcagag ccctagttca ctgtctgcct ccgtcggcga cagagtgacg     60
atcagctgcc gagccagcca agatattagt aactacctca attggtacca gcagaaacct   120
ggaaaagcac ccaagctttt gatctattac accagcaggc tgcatagcgg agtgccgagc   180
agatttcgg gttctggcag cggcaccgat ttctctctga ctatcagtag cctgcaaccc    240
gaagacattg ctacatatta ttgtcagcag ggaatcaccc ctccatggac atttggaggg   300
ggaacaaagg tggagattaa a                                             321

SEQ ID NO: 69              moltype = AA   length = 214
FEATURE                    Location/Qualifiers
REGION                     1..214
                           note = Amino acid sequence of hz8G11 light chain
source                     1..214
                           mol_type = protein
                           organism = synthetic construct
SEQUENCE: 69
```

```
DIQMTQSPSS LSASVGDRVT ISCRASQDIS NYLNWYQQKP GKAPKLLIYY TSRLHSGVPS    60
RFSGSGSGTD FSLTISSLQP EDIATYYCQQ GITPPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 70           moltype = DNA  length = 642
FEATURE                 Location/Qualifiers
misc_feature            1..642
                        note = Nucleic acid sequence of hz8G11 light chain
source                  1..642
                        mol_type = other DNA
                        organism = synthetic construct
SEQUENCE: 70
gacatacaga tgacgcagag ccctagttca ctgtctgcct ccgtcggcga cagagtgacg    60
atcagctgcc gagccagcca agatattagt aactacctca attggtacca gcagaaacct   120
ggaaaagcac ccaagctttt gatctattac accagcaggc tgcatagcgg agtgccgagc   180
agattttcgg gttctggcag cggcaccgat ttctctctga ctatcagtag cctgcaaccc   240
gaagacattg ctacatatta ttgtcagcag gggatcaccc ctccatggac atttggaggg   300
ggaacaaagg tggagattaa acggaccgtg gccgctcccc ccgtgttcat cttcccaccc   360
tccgacgagc agctgaagtc cggcaccgcc agcgtggtct gcctgctgaa caacttctac   420
ccccgcgagg ccaaggtgca gtggaaggtg gacaacgccc tgcagtccgg caactcccag   480
gaatccgtca ccgagcagga ctccaaggac agcacctact ccctgtcctc caccctgacc   540
ctgtccaagg ccgactacga aaagcacaag gtgtacgcct gcgaagtgac ccaccagggc   600
ctgtccagcc ccgtgaccaa gtccttcaac cggggcgagt gc                      642

SEQ ID NO: 71           moltype = AA  length = 9
FEATURE                 Location/Qualifiers
REGION                  1..9
                        note = CDRH3 of hz39D2.14 antibody
source                  1..9
                        mol_type = protein
                        organism = synthetic construct
SEQUENCE: 71
DEYYVRTDY                                                             9

SEQ ID NO: 72           moltype = AA  length = 9
FEATURE                 Location/Qualifiers
REGION                  1..9
                        note = CDRH3 of hz39D2.22 and hz39D2.23 antibody
source                  1..9
                        mol_type = protein
                        organism = synthetic construct
SEQUENCE: 72
DEYYVRVDY                                                             9

SEQ ID NO: 73           moltype = AA  length = 9
FEATURE                 Location/Qualifiers
REGION                  1..9
                        note = CDRL3 of hz39D2.22 antibody
source                  1..9
                        mol_type = protein
                        organism = synthetic construct
SEQUENCE: 73
LELDEFPWT                                                             9

SEQ ID NO: 74           moltype = AA  length = 9
FEATURE                 Location/Qualifiers
REGION                  1..9
                        note = CDRL3 of hz39D2.23 antibody
source                  1..9
                        mol_type = protein
                        organism = synthetic construct
SEQUENCE: 74
LQLDEFPWT                                                             9

SEQ ID NO: 75           moltype = AA  length = 121
FEATURE                 Location/Qualifiers
REGION                  1..121
                        note = Amino acid sequence of 2G10 heavy chain variable
                         region
source                  1..121
                        mol_type = protein
                        organism = synthetic construct
SEQUENCE: 75
EVKLLESGGG LVQPGGSLKL SCATSGFTFS DYYMYWVRQT PEMRLEWVAY INSGGGSTYY    60
PDTVKGRFTI SRDNAKNTLY LQMSRLKSED TAMYYCAREA LYDYDYAMDY WGQGTTVTVS   120
S                                                                    121

SEQ ID NO: 76           moltype = DNA  length = 363
```

| | |
|---|---|
| FEATURE | Location/Qualifiers |
| misc_feature | 1..363 |
| | note = Nucleic acid sequence of 2G10 heavy chain variable region |
| source | 1..363 |
| | mol_type = other DNA |
| | organism = synthetic construct |

SEQUENCE: 76
```
gaggtgaagc ttctcgagtc tgggggaggc ttagtgcagc ctggagggtc cctgaaactc    60
tcctgtgcaa cctctggatt cactttcagt gactattaca tgtattgggt tcgccagact   120
ccagagatga ggctggagtg ggtcgcatat attaatagtg gtggtggtag cacctattat   180
ccagacactg taaagggccg attcaccatc tccagagaca tgccaagaa caccctgtac   240
ctgcaaatga gccgtctgaa gtctgaggac acagccatgt attactgtgc aagagaggcc   300
ctctatgatt acgactatgc tatggactac tggggtcaag gaaccacggt caccgtctcc   360
tca                                                                 363
```

| | |
|---|---|
| SEQ ID NO: 77 | moltype = AA  length = 112 |
| FEATURE | Location/Qualifiers |
| REGION | 1..112 |
| | note = Amino acid sequence of 2G10 light chain variable region |
| source | 1..112 |
| | mol_type = protein |
| | organism = synthetic construct |

SEQUENCE: 77
```
DIVMTQSPLT LSVTIGQPAS ISCKSSQSLL YSNGKTYLNW LLQRPGQSPK RLIYLVSKLD    60
SGVPDRFTGS GSGTDFTLKI SRVEAEDLGV YYCVQGTHFP LTFGAGTKLE LK           112
```

| | |
|---|---|
| SEQ ID NO: 78 | moltype = DNA  length = 336 |
| FEATURE | Location/Qualifiers |
| misc_feature | 1..336 |
| | note = Nucleic acid sequence of 2G10 light chain variable region |
| source | 1..336 |
| | mol_type = other DNA |
| | organism = synthetic construct |

SEQUENCE: 78
```
gatattgtga tgacccagtc tccactcact ttgtcggtta ccattggaca accagcctct    60
atctcttgca agtcaagtca gagcctctta tatagtaatg gaaaaaccta tttgaattgg   120
ttattacaga ggccaggcca gtctccaaag cgcctaatct atctggtgtc taaactggac   180
tctggagtcc ctgacaggtt cactggcagt gggtcaggaa cagatttttac actgaaaatc   240
agcagagtgg aggctgagga tttgggagtt tattactgcg tgcaaggtac acattttccg   300
ctcacgttcg gtgctgggac caagctggag ctgaaa                             336
```

| | |
|---|---|
| SEQ ID NO: 79 | moltype = AA  length = 115 |
| FEATURE | Location/Qualifiers |
| REGION | 1..115 |
| | note = Amino acid sequence of 8G11 heavy chain variable region |
| source | 1..115 |
| | mol_type = protein |
| | organism = synthetic construct |

SEQUENCE: 79
```
EVQLQQSGPD LVKPGTSVKI SCKASGYSFT GYYMHWVKQS HGKSLEWIGH INPNNGGTSY    60
NQKFKGKTIL TVDKSSSTAF MELRSLTSED SAVYYCAREE AFAYWGQGTL VTVSA        115
```

| | |
|---|---|
| SEQ ID NO: 80 | moltype = DNA  length = 345 |
| FEATURE | Location/Qualifiers |
| misc_feature | 1..345 |
| | note = Nucleic acid sequence of 8G11 heavy chain variable region |
| source | 1..345 |
| | mol_type = other DNA |
| | organism = synthetic construct |

SEQUENCE: 80
```
gaggtgcaac ttcagcagtc tggacctgac ctggtgaagc ctgggacttc agtgaagata    60
tcctgcaagg cttctggtta ctcattcact ggctactaca tgcactgggt gaagcagagc   120
catggaaaga gccttgagtg gattggacat attaatccta caaatggtgg tactagctac   180
aaccagaagt tcaagggcaa gaccatatta actgtggaca agagccttcc acagccttc    240
atggagctcc gcagcctgac atctgaggac tctgcggtct attactgcgc aagagaagaa   300
gccttttgctt actgggccca agggactctg tcactgtct ctgca                   345
```

| | |
|---|---|
| SEQ ID NO: 81 | moltype = AA  length = 107 |
| FEATURE | Location/Qualifiers |
| REGION | 1..107 |
| | note = Amino acid sequence of 8G11 light chain variable region |
| source | 1..107 |
| | mol_type = protein |

```
                                    organism = synthetic construct
SEQUENCE: 81
DIVMTQSTSS LSASLGDRVT ISCRASQDIS NYLNWYQQKP DGTVKLLIYY TSRLHSGVPS      60
RFSGSGSGTD FSLTISNVEQ EDIATYFCQQ GITPPWTFGG GTKLELK                  107

SEQ ID NO: 82              moltype = DNA  length = 321
FEATURE                    Location/Qualifiers
misc_feature               1..321
                           note = Nucleic acid sequence of 8G11 light chain variable
                             region
source                     1..321
                           mol_type = other DNA
                           organism = synthetic construct
SEQUENCE: 82
gatattgtga tgacccagtc tacatcctcc ctgtctgcct ctctgggaga cagagtcacc      60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat ttttctctca ccattagcaa cgtggagcaa    240
gaagacattg ccacttactt ttgccaacag ggtattacgc ctccgtggac gttcggtgga    300
gggaccaagc tggagctgaa a                                              321

SEQ ID NO: 83              moltype = AA  length = 118
FEATURE                    Location/Qualifiers
REGION                     1..118
                           note = Amino acid sequence of 39D2 heavy chain variable
                             region
source                     1..118
                           mol_type = protein
                           organism = synthetic construct
SEQUENCE: 83
EVQLQQSGPE LKKPGETVKI SCKASGYTFT NYGVNWVKQA PGKGLKWMGW INTHTGEPTY      60
AEEFKGRFAF SLETSASTAY LQINNLKNED TATYFCARDD YYVRVDYWGQ GTTLTVSS      118

SEQ ID NO: 84              moltype = DNA  length = 354
FEATURE                    Location/Qualifiers
misc_feature               1..354
                           note = Nucleic acid sequence of 39D2 heavy chain variable
                             region
source                     1..354
                           mol_type = other DNA
                           organism = synthetic construct
SEQUENCE: 84
gaggttcagc tgcagcagtc tggacctgag ctgaagaagc ctggagagac agtcaagatc      60
tcctgcaagg cttctgggta taccttcaca aactatggag tgaattgggt gaagcaggct    120
ccaggaaagg gtttaaagtg gatgggctgg ataaacaccc acactggaga gccaacatat    180
gctgaagagt tcaagggacg gtttgccttc tctttggaaa cctctgccag cactgcctat    240
ttgcagatca caaacctcaa aaatgaggac acggctacat atttctgtgc aagagatgat    300
tactacgtaa gggtagacta ctggggccaa ggcaccactc tcacagtctc ctca          354

SEQ ID NO: 85              moltype = AA  length = 107
FEATURE                    Location/Qualifiers
REGION                     1..107
                           note = Amino acid sequence of 39D2 light chain variable
                             region
source                     1..107
                           mol_type = protein
                           organism = synthetic construct
SEQUENCE: 85
DIVMTQSPSS MYASLGERVT ITCKASQDIN SYLSWFQQKP GKSPKTLIYR ANRLVDGVPS      60
RFSGSGSGQD YSLTISSLEY EDMGIYYCLQ YDEFPWTFGG GTKLELK                  107

SEQ ID NO: 86              moltype = DNA  length = 321
FEATURE                    Location/Qualifiers
misc_feature               1..321
                           note = Nucleic acid sequence of 39D2 light chain variable
                             region
source                     1..321
                           mol_type = other DNA
                           organism = synthetic construct
SEQUENCE: 86
gatattgtaa tgacccagtc tccatcttcc atgtatgcat ccctaggaga gagagtcact      60
atcacttgca aggcgagtca ggacattaat agctatttaa gctggttcca gcagaaacca    120
gggaaatctc ctaagaccct gatctatcgt gcaaacagat tggtagatgg ggtcccatca    180
aggttcagtg gcagtggatc tgggcaagat tattctctca ccatcagcag cctggagtat    240
gaagatatgg gaatttatta ttgtctacag tatgatgagt tccgtggacg ttcggtgga     300
gggaccaagc tggagctgaa a                                              321

SEQ ID NO: 87              moltype = AA  length = 118
FEATURE                    Location/Qualifiers
```

| | |
|---|---|
| REGION | 1..118<br>note = Amino acid sequence of hz39D2.14 heavy chain variable region |
| source | 1..118<br>mol_type = protein<br>organism = synthetic construct |

SEQUENCE: 87
```
QVQLVQSGSE LKKPGASVKV SCKASGYTFT NYGVNWVRQA PGQGLEWMGW INTHTGEPTY   60
AEEFKGRFVF SLDTSVSTAY LQISSLKAED TAVYYCARDE YYVRTDYWGQ GTTVTVSS   118
```

| | |
|---|---|
| SEQ ID NO: 88 | moltype = DNA  length = 354 |
| FEATURE | Location/Qualifiers |
| misc_feature | 1..354<br>note = Nucleic acid sequence of hz39D2.14 heavy chain variable region |
| source | 1..354<br>mol_type = other DNA<br>organism = synthetic construct |

SEQUENCE: 88
```
caagtccaac tcgtgcagtc aggatctgaa ctgaagaaac ctggagcgag cgttaaggtt    60
tcctgcaagg ccagcggcta tacgttcact aactatggtg tcaactgggt gagacaggca   120
cccggccagg gcctggagtg gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgag   300
tactatgtga ggaccgatta ctgggggcag ggaccaccg tgacagtctc aagt          354
```

| | |
|---|---|
| SEQ ID NO: 89 | moltype = AA  length = 448 |
| FEATURE | Location/Qualifiers |
| REGION | 1..448<br>note = Amino acid sequence of hz39D2.14 heavy chain |
| source | 1..448<br>mol_type = protein<br>organism = synthetic construct |

SEQUENCE: 89
```
QVQLVQSGSE LKKPGASVKV SCKASGYTFT NYGVNWVRQA PGQGLEWMGW INTHTGEPTY    60
AEEFKGRFVF SLDTSVSTAY LQISSLKAED TAVYYCARDE YYVRTDYWGQ GTTVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448
```

| | |
|---|---|
| SEQ ID NO: 90 | moltype = DNA  length = 1344 |
| FEATURE | Location/Qualifiers |
| misc_feature | 1..1344<br>note = Nucleic acid sequence of hz39D2.14 heavy chain |
| source | 1..1344<br>mol_type = other DNA<br>organism = synthetic construct |

SEQUENCE: 90
```
caagtccaac tcgtgcagtc aggatctgaa ctgaagaaac ctggagcgag cgttaaggtt     60
tcctgcaagg ccagcggcta tacgttcact aactatggtg tcaactgggt gagacaggca   120
cccggccagg gcctggagtg gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgag   300
tactatgtga ggaccgatta ctgggggcag ggaccaccg tgacagtctc aagtgcctcc   360
accaagggcc cctccgtgtt ccctctggcc cctccagca gtccacctc tggcggcaca    420
gccgccctgg gctgcctggt gaaagactac ttccccgagc ccgtgaccgt gtcctggaac   480
tctggcgccc tgacctccgg cgtgcacacc ttccctgccg tgctgcagtc ctccggcctg   540
tactccctgt cctccgtggt gaccgtgccc tccagctctc tgggcaccca gacctacatc   600
tgtaacgtga accacaagcc ctccaacacc aaggtggaca gaaggtgga acccaagtcc   660
tgcgacaaga cccacacctg tcccccctgc cctgcccctg aactgctggg cggaccttcc   720
gtgttcctgt tcccccccaa gcccaaggac accctgatga tctcccggac ccccgaagtg   780
acctgcgtgg tggacgtgtc cccacgag accctgaag tgaagttcaa ttggtacgtg    840
gacggcgtgg aagtgcacaa tgccaagacc aagcccagag gaacagta caactccacc   900
taccgggtgg tgtctgtgct gaccgtgctg caccaggact ggctgaacgg caaagaatac   960
aagtgcaaag tctccaacaa ggccctgcct gcccccatcg aaaagaccat ctccaaggcc  1020
aagggccagc cccgcgagcc ccaggtgtac accctgcccc ctagccggga cgagctgacc  1080
aagaaccagg tgtccctgac ctgtctggtg aaaggcttct acccctccga cattgccgtg  1140
gaatgggagt ccaacggcca gcccgagaac aactacaaga ccacccccc tgtgctggac  1200
tccgacggct cattcttcct gtactccaag ctgaccgtgg acaagtcccg gtggcagcag  1260
ggcaacgtgt tctcctgctc cgtgatgcac gaggccctgc acaaccacta cacccagaag  1320
tccctgtccc tgagccccgg caag                                         1344
```

| | |
|---|---|
| SEQ ID NO: 91 | moltype = AA  length = 107 |
| FEATURE | Location/Qualifiers |
| REGION | 1..107<br>note = Amino acid sequence of hz39D2.14 light chain |

```
                              variable region
source                        1..107
                              mol_type = protein
                              organism = synthetic construct
SEQUENCE: 91
DIQMTQSPSS LSASVGDRVT ITCKASQDIN SYLSWFQQKP GKAPKTLIYR ANRLVDGVPS    60
RFSGSGSGQD YTLTISSLQP EDFATYYCLQ YDEFPWTFGQ GTKVEIK                 107

SEQ ID NO: 92                 moltype = DNA  length = 321
FEATURE                       Location/Qualifiers
misc_feature                  1..321
                              note = Nucleic acid sequence of hz39D2.14 light chain
                              variable region
source                        1..321
                              mol_type = other DNA
                              organism = synthetic construct
SEQUENCE: 92
cggaccgtgg ccgctccctc cgtgttcatc ttcccaccct ccgacgagca gctgaagtcc    60
ggcaccgcca gcgtggtctg cctgctgaac aacttctacc ccgcgaggc caaggtgcag   120
tggaaggtgg acaacgccct gcagtccggc aactcccagg aatccgtcac cgagcaggac   180
tccaaggaca gcacctactc cctgtcctcc accctgaccc tgtccaaggc cgactacgag   240
aagcacaagg tgtacgcctg cgaagtgacc caccagggc tgtccagccc cgtgaccaag   300
tccttcaacc ggggcgagtg c                                             321

SEQ ID NO: 93                 moltype = AA  length = 214
FEATURE                       Location/Qualifiers
REGION                        1..214
                              note = Amino acid sequence of hz39D2.14 light chain
source                        1..214
                              mol_type = protein
                              organism = synthetic construct
SEQUENCE: 93
DIQMTQSPSS LSASVGDRVT ITCKASQDIN SYLSWFQQKP GKAPKTLIYR ANRLVDGVPS    60
RFSGSGSGQD YTLTISSLQP EDFATYYCLQ YDEFPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 94                 moltype = DNA  length = 642
FEATURE                       Location/Qualifiers
misc_feature                  1..642
                              note = Nucleic acid sequence of hz39D2.14 light chain
source                        1..642
                              mol_type = other DNA
                              organism = synthetic construct
SEQUENCE: 94
gacattcaaa tgacacagtc tcccagctcc cttagtgctt cggtgggcga tcgggtgacc    60
ataacatgca aggcctcaca ggacatcaac agctatctct catggtttca gcagaagcca   120
ggaaaagcac ctaaaacgtt gatctacagg gccaatcgcc tcgttgacgg agtcccctcc   180
agattcagcg ggagtgggtc tggtcaggat tatactctga ccatctcctc tctgcagcct   240
gaagactttg ccacttacta ctgtctgcaa tacgatgagt tccatggac cttcggccag   300
ggcaccaagg tggagattaa acggaccgtg gccgctccc cgtgttcat cttcccaccc   360
tccgacgagc agctgaagtc cggcaccgcc agcgtggtct gcctgctgaa caacttctac   420
ccccgcgagg ccaaggtgca gtggaaggtg gacaacgccc tgcagtccgg caactcccag   480
gaatccgtca ccgagcagga ctccaaggac agcacctact ccctgtcctc caccctgacc   540
ctgtccaagg ccgactacga gaagcacaag gtgtacgcct gcgaagtgac ccaccagggc   600
ctgtccagcc ccgtgaccaa gtccttcaac cggggcgagt gc                      642

SEQ ID NO: 95                 moltype = AA  length = 118
FEATURE                       Location/Qualifiers
REGION                        1..118
                              note = Amino acid sequence of hz39D2.22 heavy chain
                              variable region
source                        1..118
                              mol_type = protein
                              organism = synthetic construct
SEQUENCE: 95
QVQLVQSGSE LKKPGASVKV SCKASGYTFT NYGVNWVRQA PGQGLEWMGW INTHTGEPTY    60
AEEFKGRFVF SLDTSVSTAY LQISSLKAED TAVYYCARDE YVRVDYWGQ GTTVTVSS     118

SEQ ID NO: 96                 moltype = DNA  length = 354
FEATURE                       Location/Qualifiers
misc_feature                  1..354
                              note = Nucleic acid sequence of hz39D2.22 heavy chain
                              variable region
source                        1..354
                              mol_type = other DNA
                              organism = synthetic construct
SEQUENCE: 96
caagtccaac tcgtgcagtc aggatctgaa ctgaagaaac ctggagcgag cgttaaggtt    60
```

-continued

```
tcctgcaagg ccagcggcta tacgttcact aactatggtg tcaactgggt gagacaggca   120
cccggccagg gcctggagtg gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgag   300
tactatgtga gggtggatta ctgggggcag gggaccaccg tgacagtctc aagt         354
```

SEQ ID NO: 97          moltype = AA    length = 448
FEATURE                  Location/Qualifiers
REGION                    1..448
                          note = Amino acid sequence of hz39D2.22 heavy chain
source                    1..448
                          mol_type = protein
                          organism = synthetic construct
SEQUENCE: 97

```
QVQLVQSGSE LKKPGASVKV SCKASGYTFT NYGVNWVRQA PGQGLEWMGW INTHTGEPTY    60
AEEFKGRFVF SLDTSVSTAY LQISSLKAED TAVYYCARDE YYVRVDYWGQ GTTVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448
```

SEQ ID NO: 98          moltype = DNA   length = 1344
FEATURE                  Location/Qualifiers
misc_feature           1..1344
                          note = Nucleic acid sequence of hz39D2.22 heavy chain
source                    1..1344
                          mol_type = other DNA
                          organism = synthetic construct
SEQUENCE: 98

```
caagtccaac tcgtgcagtc aggatctgaa ctgaagaaac ctggagcgag cgttaaggtt    60
tcctgcaagg ccagcggcta tacgttcact aactatggtg tcaactgggt gagacaggca   120
cccggccagg gcctggagtg gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgag   300
tactatgtga gggtggatta ctgggggcag gggaccaccg tgacagtctc aagtgcctcc   360
accaagggcc cctccgtgtt ccctctggcc cctccagca  agtccacctc tggcggcaca   420
gccgccctgg gctgcctggt gaaagactac ttccccgagc ccgtgaccgt gtcctggaac   480
tctggcgccc tgacctccgg cgtgcacacc ttccctgccg tgctgcagtc ctccggcctg   540
tactccctgt cctccgtggt gaccgtgccc tccagctctc tgggcaccca gacctacatc   600
tgtaacgtga accacaagcc ctccaacacc aaggtggaca gaaggtggaa acccaagtcc   660
tgcgacaaga cccacacctg tcccccctgc cctgcccctg aactgctggg cggacctcc   720
gtgttcctgt tccccccaaa gcccaaggac accctgatga tctcccggac ccccgaagtg   780
acctgcgtgg tggtggacgt gtcccacgag gaccctgaag tgaagttcaa ttggtacgtg   840
gacggcgtgg aagtgcacaa tgccaagacc aagcccagag gaacagta caactccacc   900
taccgcgtgg tgtctgtgct gaccgtgctg caccaggact ggctgaacgg caaagaatac   960
aagtgcaaag tctccaacaa ggccctgcct gccccatcg aaaagaccat ctccaaggcc  1020
aagggccagc ccgcgagcc ccaggtgtac acctgccccc ctagcggga cgagctgacc  1080
aagaaccagg tgtccctgac ctgtctggtg aaaggcttct accctccga cattgccgtg  1140
gaatgggagt ccaacggcca gcccgagaac aactacaaga ccacccccccc tgtgctggac  1200
tccgacggct cattcttcct gtactccaag ctgaccgtgg acaagtcccg gtggcagcag  1260
ggcaacgtgt tctcctgctc cgtgatgcac gaggccctgc acaaccacta cacccagaag  1320
tccctgtccc tgagcccggg caag                                        1344
```

SEQ ID NO: 99          moltype = AA    length = 107
FEATURE                  Location/Qualifiers
REGION                    1..107
                          note = Amino acid sequence of hz39D2.22 light chain
                          variable region
source                    1..107
                          mol_type = protein
                          organism = synthetic construct
SEQUENCE: 99

```
DIQMTQSPSS LSASVGDRVT ITCKASQDIN SYLSWFQQKP GKAPKTLIYR ANRLVDGVPS    60
RFSGSGSGQD YTLTISSLQP EDFATYYCLE LDEFPWTFGQ GTKVEIK                107
```

SEQ ID NO: 100         moltype = DNA   length = 321
FEATURE                  Location/Qualifiers
misc_feature           1..321
                          note = Nucleic acid sequence of hz39D2.22 light chain
                          variable region
source                    1..321
                          mol_type = other DNA
                          organism = synthetic construct
SEQUENCE: 100

```
gacattcaaa tgacacagtc tcccagctcc cttagtgctt cggtgggcga tcgggtgacc    60
ataacatgca aggcctcaca ggacatcaac agctatctct catggtttca gcagaagcca   120
ggaaaagcac ctaaaacgtt gatctacagg gccaatcgcc tcgttgacgg agtccccctcc  180
```

```
agattcagcg ggagtgggtc tggtcaggat tatactctga ccatctcctc tctgcagcct    240
gaagactttg ccacttacta ctgtctggag ctcgatgagt tcccatggac cttcggccag    300
ggcaccaagg tggagattaa a                                              321

SEQ ID NO: 101          moltype = AA   length = 214
FEATURE                 Location/Qualifiers
REGION                  1..214
                        note = Amino acid sequence of hz39D2.22 light chain
source                  1..214
                        mol_type = protein
                        organism = synthetic construct
SEQUENCE: 101
DIQMTQSPSS LSASVGDRVT ITCKASQDIN SYLSWFQQKP GKAPKTLIYR ANRLVDGVPS     60
RFSGSGSGQD YTLTISSLQP EDFATYYCLE LDEFPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 102          moltype = DNA   length = 642
FEATURE                 Location/Qualifiers
misc_feature            1..642
                        note = Nucleic acid sequence of hz39D2.22 light chain
source                  1..642
                        mol_type = other DNA
                        organism = synthetic construct
SEQUENCE: 102
gacattcaaa tgacacagtc tcccagctcc cttagtgctt cggtgggcga tcgggtgacc     60
ataacatgca aggcctcaca ggacatcaac agctatctct catggtttca gcagaagcca    120
ggaaaagcac ctaaaacgtt gatctacagg gccaatcgcc tcgttgacgg agtccctcc    180
agattcagcg ggagtgggtc tggtcaggat tatactctga ccatctcctc tctgcagcct    240
gaagactttg ccacttacta ctgtctggag ctcgatgagt tcccatggac cttcggccag    300
ggcaccaagg tggagattaa acggaccgtg gccgctcccc ccgtgttcat cttcccaccc    360
tccgacgagc agctgaagtc cggcaccgcc agcgtggtct gctgctgaa caacttctac    420
ccccgcgagg ccaaggtgca gtggaaggtg gacaacgccc tgcagtccgg caactcccag    480
gaatccgtca ccgagcagga ctccaaggac agcacctact ccctgtcctc caccctgacc    540
ctgtccaagg ccgactacga gaagcacaag gtgtacgcct gcgaagtgac ccaccagggc    600
ctgtccagcc ccgtgaccaa gtccttcaac cgggcgagt gc                       642

SEQ ID NO: 103          moltype = AA   length = 118
FEATURE                 Location/Qualifiers
REGION                  1..118
                        note = Amino acid sequence of hz39D2.23 heavy chain
                               variable region
source                  1..118
                        mol_type = protein
                        organism = synthetic construct
SEQUENCE: 103
QVQLVQSGSE LKKPGASVKV SCKASGYTFT NYGVNWVRQA PGQGLEWMGW INTHTGEPTY     60
AEEFKGRFVF SLDTSVSTAY LQISSLKAED TAVYYCARDE YYVRVDYWGQ GTTVTVSS     118

SEQ ID NO: 104          moltype = DNA   length = 354
FEATURE                 Location/Qualifiers
misc_feature            1..354
                        note = Nucleic acid sequence of hz39D2.23 heavy chain
                               variable region
source                  1..354
                        mol_type = other DNA
                        organism = synthetic construct
SEQUENCE: 104
caagtccaac tcgtgcagtc aggatctgaa ctgaagaaac ctggagcgag cgttaaggtt     60
tcctgcaagg ccagcggcta tacgttcact aactatggtg tcaactgggt gagacaggca    120
cccggccagg gcctggagtg gatgggttgg atcaatactc acacagggga accaacatat    180
gctgaggagt tcaaaggacg gtttgttttt agtctggaca cctccgtgtc taccgcctac    240
ctgcagattt ccagccttaa agcagaggac actgctgtat actactgtgc cagagacgag    300
tactatgtga gggtggatta ctgggggcag gggaccaccg tgacagtctc aagt          354

SEQ ID NO: 105          moltype = AA   length = 448
FEATURE                 Location/Qualifiers
REGION                  1..448
                        note = Amino acid sequence of hz39D2.23 heavy chain
source                  1..448
                        mol_type = protein
                        organism = synthetic construct
SEQUENCE: 105
QVQLVQSGSE LKKPGASVKV SCKASGYTFT NYGVNWVRQA PGQGLEWMGW INTHTGEPTY     60
AEEFKGRFVF SLDTSVSTAY LQISSLKAED TAVYYCARDE YYVRVDYWGQ GTTVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSRDELT    360
```

KNQVSLTCLV KGFYPSDIAV EWESNGQPEN NYKTTPPVLD SDGSFFLYSK LTVDKSRWQQ 420
GNVFSCSVMH EALHNHYTQK SLSLSPGK                                  448

SEQ ID NO: 106          moltype = DNA   length = 1344
FEATURE                 Location/Qualifiers
misc_feature            1..1344
                        note = Nucleic acid sequence of hz39D2.23 heavy chain
source                  1..1344
                        mol_type = other DNA
                        organism = synthetic construct
SEQUENCE: 106
caagtccaac tcgtgcagtc aggatctgaa ctgaagaaac tggagcgag cgttaaggtt  60
tcctgcaagg ccagcggcta tacgttcact aactatggtg tcaactgggt gagacaggca 120
cccgccagg gcctggagtg gatggttgg atcaatactc acacagggga accaactat  180
gctgaggagt tcaaaggacg gtttgttttt agtctggaca cctccgtgtc taccgcctac 240
ctgcagattt ccagccttaa agcagaggac actgctgtat actactgtgc cagagacgag 300
tactatgtga gggtggatta ctgggggcag ggaccaccg tgacagtctc aagtgcctcc 360
accaagggcc cctccgtgtt ccctctggcc ccctccagca gtccacctc tggcggcaca 420
gccgccctgg gctgcctggt gaaagactac ttccccgagc ccgtgaccgt gtcctggaac 480
tctggcgccc tgacctccgg cgtgcacacc ttccctgccg tgctgcagtc ctccggcctg 540
tactccctgt cctccgtggt gaccgtgccc tccagctctc tgggcaccca gacctacatc 600
tgtaacgtga accacaagcc ctccaacacc aaggtgacaa agaaggtgaa acccaagtcc 660
tgcgacaaga cccacacctg tccccctgc cctgccctg aactgctggg cggaccttcc 720
gtgttcctgt tccccccaaa gcccaaggac accctgatga tctcccggac cccgaagtg 780
acctgcgtgt ggtggacgt gtcccacgag accctgaag tgaagttcaa ttggtacgtg 840
gacggcgtgg aagtgcacaa tgccaagacc aagcccgga aggaacagta caactccacg 900
taccgggtgg tgtctgtgct gaccgtgctg caccaggact ggctgaacgg caaagaatac 960
aagtgcaaag tctccaacaa ggcctgcct gccccatcg aaaagaccat ctccaaggcc 1020
aagggccagc ccgcgagcc ccaggtgtac accctgcccc ctagccggga cgagctgacc 1080
aagaaccagg tgtccctgac ctgtctggtg aaaggcttct accctcga cattgccgtg 1140
gaatgggagt ccaacggcca gcccgagaac aactacaaga ccacccccc tgtgctggac 1200
tccgacggct cattcttcct gtactccaag ctgaccgtgg acaagtccg gtggcagcag 1260
ggcaacgtgt tctcctgctc cgtgatgcac gaggccctgc acaaccacta cacccagaag 1320
tccctgtccc tgagccccgg caag                                       1344

SEQ ID NO: 107          moltype = AA   length = 107
FEATURE                 Location/Qualifiers
REGION                  1..107
                        note = Amino acid sequence of hz39D2.23 light chain
                         variable region
source                  1..107
                        mol_type = protein
                        organism = synthetic construct
SEQUENCE: 107
DIQMTQSPSS LSASVGDRVT ITCKASQDIN SYLSWFQQKP GKAPKTLIYR ANRLVDGVPS  60
RFSGSGSGQD YTLTISSLQP EDFATYYCLQ LDEFPWTFGQ GTKVEIK               107

SEQ ID NO: 108          moltype = DNA   length = 321
FEATURE                 Location/Qualifiers
misc_feature            1..321
                        note = Nucleic acid sequence of hz39D2.23 light chain
                         variable region
source                  1..321
                        mol_type = other DNA
                        organism = synthetic construct
SEQUENCE: 108
gacattcaaa tgacacagtc tcccagctcc cttagtgctt cggtgggcga tcgggtgacc  60
ataacatgca aggcctcaca ggacatcaac agctatctct catggtttca gcagaagcca 120
ggaaaagcac ctaaaacgtt gatctacagg gccaatcgcc tcgttgacgg agtccctcc  180
agattcagcg ggagtgggtc tggtcaggat tatactctga ccatctcctc tctgcagcct 240
gaagactttg ccacttacta ctgtctgcaa ctcgatgagt tcccatggac cttcggccag 300
ggcaccaagg tggagattaa a                                          321

SEQ ID NO: 109          moltype = AA   length = 214
FEATURE                 Location/Qualifiers
REGION                  1..214
                        note = Amino acid sequence of hz39D2.23 light chain
source                  1..214
                        mol_type = protein
                        organism = synthetic construct
SEQUENCE: 109
DIQMTQSPSS LSASVGDRVT ITCKASQDIN SYLSWFQQKP GKAPKTLIYR ANRLVDGVPS  60
RFSGSGSGQD YTLTISSLQP EDFATYYCLQ LDEFPWTFGQ GTKVEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                             214

SEQ ID NO: 110          moltype = DNA   length = 642
FEATURE                 Location/Qualifiers
misc_feature            1..642

```
                       note = Nucleic acid sequence of hz39D2.23 light chain
source                 1..642
                       mol_type = other DNA
                       organism = synthetic construct
SEQUENCE: 110
gacattcaaa tgacacagtc tcccagctcc cttagtgctt cggtgggcga tcgggtgacc    60
ataacatgca aggcctcaca ggacatcaac agctatctct catggtttca gcagaagcca   120
ggaaaagcac ctaaaacgtt gatctacagg gccaatcgcc tcgttgacgg agtcccctcc   180
agattcagcg ggagtgggtc tggtcaggat tatactctga ccatctcctc tctgcagcct   240
gaagactttg ccacttacta ctgtctgcaa tacgatgagt tcccatggac cttcggccag   300
ggcaccaagg tggagattaa acggaccgtg gccgctccct ccgtgttcat cttcccaccc   360
tccgacgagc agctgaagtc cggcaccgcc agcgtggtct gcctgctgaa caacttctac   420
ccccgcgagg ccaaggtgca gtggaaggtg gacaacgccc tgcagtccgg caactcccag   480
gaatccgtca ccgagcagga ctccaaggac agcacctact cccctgtcct caccctgacc   540
ctgtccaagg ccgactacga aagcacaag gtgtacgcct gcgaagtgac ccaccagggc   600
ctgtccagcc ccgtgaccaa gtccttcaac cggggcgagt gc                     642

SEQ ID NO: 111         moltype = AA   length = 21
FEATURE                Location/Qualifiers
REGION                 1..21
                       note = Signal peptide (CD8alpha)
source                 1..21
                       mol_type = protein
                       organism = synthetic construct
SEQUENCE: 111
MALPVTALLL PLALLLHAAR P                                              21

SEQ ID NO: 112         moltype = DNA   length = 63
FEATURE                Location/Qualifiers
misc_feature           1..63
                       note = Signal peptide (CD8alpha)
source                 1..63
                       mol_type = other DNA
                       organism = synthetic construct
SEQUENCE: 112
atggctctgc cagtgactgc actgctgctg ccactggccc tgctgctgca cgcagctcga    60
cct                                                                  63

SEQ ID NO: 113         moltype = AA   length = 240
FEATURE                Location/Qualifiers
REGION                 1..240
                       note = Anti-HER2 scFv
source                 1..240
                       mol_type = protein
                       organism = synthetic construct
SEQUENCE: 113
DIQMTQSPSS LSASVGDRVT ITCKASQDIN SYLSWFQQKP GKAPKTLIYR ANRLVDGVPS    60
RFSGSGSGQD YTLTISSLQP EDFATYYCLQ YDEFPWTFGQ GTKVEIKGGG GSGGGGSGGG   120
GSQVQLVQSG SELKKPGASV KVSCKASGYT FTNYGVNWVR QAPGQGLEWM GWINTHTGEP   180
TYAEEFKGRF VFSLDTSVST AYLQISSLKA EDTAVYYCAR DDYYVRVDYW GQGTTVTVSS   240

SEQ ID NO: 114         moltype = DNA   length = 720
FEATURE                Location/Qualifiers
misc_feature           1..720
                       note = Anti-HER2 scFv
source                 1..720
                       mol_type = other DNA
                       organism = synthetic construct
SEQUENCE: 114
gacatccaga tgacccagag ccccagcagc ctgagcgcca gcgtgggcga cagagtgacc    60
atcacctgca aggccagcca ggacatcaac agctacctga gctggttcca gcagaagccc   120
ggcaaggccc ccaagaccct gatctacaga gccaacagac tggtggacgg cgtgccccagc 180
agattcagcg gcagcggcag cggccaggac tacaccctga ccatcagcag cctgcagccc   240
gaggactttg ccacctacta ctgcctgcag tacgacgagt tcccctggac cttcggccag   300
ggcaccaagg tggagatcaa gggtggcggt ggatcggggc gtggtggatc tggaggaggt   360
ggctccaggt gcagctggt gcagagcggc agcgagctga agaagccgg cgccagcgtg    420
aaggtgagct gcaaggccag cggctacacc ttcaccaact acggcgtgaa ctgggtgaga   480
caggcccccg gccagggcct ggagtggatg ggctggatca acacccacac cggcgagccc   540
acctacgccg aggagttcaa gggcagattc gtgttcagcc tggacaccag cgtgagccc   600
gcctacctgc agatcagcag cctgaaggcc gaggacaccg ccgtgtacta ctgcgccaga   660
gacgactact acgtgagagt ggactactgg ggccagggca ccaccgtgac cgtgagcagc   720

SEQ ID NO: 115         moltype = AA   length = 48
FEATURE                Location/Qualifiers
REGION                 1..48
                       note = Hinge (CD8alpha)
source                 1..48
                       mol_type = protein
                       organism = synthetic construct
```

```
SEQUENCE: 115
AKPTTTPAPR PPTPAPTIAS QPLSLRPEAC RPAAGGAVHT RGLDFACD                 48

SEQ ID NO: 116           moltype = DNA   length = 144
FEATURE                  Location/Qualifiers
misc_feature             1..144
                         note = Hinge (CD8alpha)
source                   1..144
                         mol_type = other DNA
                         organism = synthetic construct
SEQUENCE: 116
gcaaaaccta ccacaactcc tgcaccacgc ccccctactc agcacctac catcgcatct     60
cagccactga gtctgcgacc agaggcctgc cggcccgccg ccggcggggc cgtccatacc   120
agagggctgg actttgcctg cgat                                          144

SEQ ID NO: 117           moltype = AA   length = 24
FEATURE                  Location/Qualifiers
REGION                   1..24
                         note = Transmembrane (CD8alpha)
source                   1..24
                         mol_type = protein
                         organism = synthetic construct
SEQUENCE: 117
IYIWAPLAGT CGVLLLSLVI TLYC                                           24

SEQ ID NO: 118           moltype = DNA   length = 72
FEATURE                  Location/Qualifiers
misc_feature             1..72
                         note = Transmembrane (CD8alpha)
source                   1..72
                         mol_type = other DNA
                         organism = synthetic construct
SEQUENCE: 118
atctacattt gggcccctct ggctggaaca tgtggcgtgc tgctgctgtc cctggtcatt     60
actctgtatt gt                                                        72

SEQ ID NO: 119           moltype = AA   length = 27
FEATURE                  Location/Qualifiers
REGION                   1..27
                         note = Transmembrane (CD28)
source                   1..27
                         mol_type = protein
                         organism = synthetic construct
SEQUENCE: 119
FWVLVVVGGV LACYSLLVTV AFIIFWV                                        27

SEQ ID NO: 120           moltype = DNA   length = 81
FEATURE                  Location/Qualifiers
misc_feature             1..81
                         note = Transmembrane (CD28)
source                   1..81
                         mol_type = other DNA
                         organism = synthetic construct
SEQUENCE: 120
ttttgggtcc tggtggtcgt gggaggggtg ctggcatgtt actcactgct ggtcaccgtg     60
gccttcatca tcttctgggt g                                               81

SEQ ID NO: 121           moltype = AA   length = 112
FEATURE                  Location/Qualifiers
REGION                   1..112
                         note = Intracellular stimulatory Signal- (CD3-lambda)
source                   1..112
                         mol_type = protein
                         organism = synthetic construct
SEQUENCE: 121
RVKFSRSADA PAYQQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR            112

SEQ ID NO: 122           moltype = DNA   length = 339
FEATURE                  Location/Qualifiers
misc_feature             1..339
                         note = Intracellular stimulatory Signal- (CD3-lambda)
source                   1..339
                         mol_type = other DNA
                         organism = synthetic construct
SEQUENCE: 122
cgagtgaagt tcagcaggtc cgccgacgct cctgcatacc agcagggaca gaaccagctg     60
tataacgagc tgaatctggg ccggagagag gaatacgacg tgctggacaa aaggcggggc    120
cgggaccccg aaatgggagg gaagccacga cggaaaaacc cccaggaggg cctgtacaat    180
```

```
gagctgcaaa aggacaaaat ggccgaggct tattctgaaa tcgggatgaa gggagagaga    240
aggcgcggaa aaggccacga tggcctgtac caggggctga gcaccgctac aaaggacacc    300
tatgatgcac tgcacatgca ggccctgccc cctcggtga                            339
```

```
SEQ ID NO: 123              moltype = AA  length = 42
FEATURE                     Location/Qualifiers
REGION                      1..42
                            note = Intracellular stimulatory signal (4-1BB)
source                      1..42
                            mol_type = protein
                            organism = synthetic construct
SEQUENCE: 123
KRGRKKLLYI FKQPFMRPVQ TTQEEDGCSC RFPEEEEGGC EL                        42

SEQ ID NO: 124              moltype = DNA  length = 126
FEATURE                     Location/Qualifiers
misc_feature                1..126
                            note = Intracellular stimulatory signal (4-1BB)
source                      1..126
                            mol_type = other DNA
                            organism = synthetic construct
SEQUENCE: 124
aagcggggaa gaaagaaact gctgtacatc ttcaaacagc cctttatgag gcctgtgcag    60
accacacagg aggaagacgg ctgctcctgc cggttccccg aggaagagga aggcgggtgc    120
gagctg                                                                126

SEQ ID NO: 125              moltype = AA  length = 41
FEATURE                     Location/Qualifiers
REGION                      1..41
                            note = Intracellular stimulatory signal (CD28)
source                      1..41
                            mol_type = protein
                            organism = synthetic construct
SEQUENCE: 125
RSKRSRLLHS DYMNMTPRRP GPTRKHYQPY APPRDFAAYR S                          41

SEQ ID NO: 126              moltype = DNA  length = 123
FEATURE                     Location/Qualifiers
misc_feature                1..123
                            note = Intracellular stimulatory signal (CD28)
source                      1..123
                            mol_type = other DNA
                            organism = synthetic construct
SEQUENCE: 126
cggagcaaga ggtcccgcct gctgcacagc gactatatga acatgacccc acggagaccc    60
ggccctacac ggaaacatta ccagccctat gctccacccc gggacttcgc agcttacaga    120
agt                                                                   123

SEQ ID NO: 127              moltype = AA  length = 22
FEATURE                     Location/Qualifiers
REGION                      1..22
                            note = Intracellular stimulatory signal (OX40 ligand)
source                      1..22
                            mol_type = protein
                            organism = synthetic construct
SEQUENCE: 127
ERVQPLEENV GNAARPRFER NK                                              22

SEQ ID NO: 128              moltype = DNA  length = 66
FEATURE                     Location/Qualifiers
misc_feature                1..66
                            note = Intracellular stimulatory signal (OX40 ligand)
source                      1..66
                            mol_type = other DNA
                            organism = synthetic construct
SEQUENCE: 128
gaaagagtgc agcccctgga agagaatgtc gggaatgccg ctcgcccaag atttgaaagg    60
aacaaa                                                                66

SEQ ID NO: 129              moltype = AA  length = 445
FEATURE                     Location/Qualifiers
REGION                      1..445
                            note = Her2-Z CAR (Clone #2)
source                      1..445
                            mol_type = protein
                            organism = synthetic construct
SEQUENCE: 129
MALPVTALLL PLALLLHAAR PDIQMTQSPS SLSASVGDRV TITCKASQDI NSYLSWFQQK    60
PGKAPKTLIY RANRLVDGVP SRFSGSGSGQ DYTLTISSLQ PEDFATYYCL QYDEFPWTFG    120
```

```
QGTKVEIKGG GGSGGGGSGG GGSQVQLVQS GSELKKPGAS VKVSCKASGY TFTNYGVNWV  180
RQAPGQGLEW MGWINTHTGE PTYAEEFKGR FVFSLDTSVS TAYLQISSLK AEDTAVYYCA  240
RDDYYVRVDY WGQGTTVTVS SAKPTTTPAP RPPTPAPTIA SQPLSLRPEA CRPAAGGAVH  300
TRGLDFACDI YIWAPLAGTC GVLLLSLVIT LYCRVKFSRS ADAPAYQQGQ NQLYNELNLG  360
RREEYDVLDK RRGRDPEMGG KPRRKNPQEG LYNELQKDKM AEAYSEIGMK GERRRGKGHD  420
GLYQGLSTAT KDTYDALHMQ ALPPR                                       445

SEQ ID NO: 130          moltype = DNA   length = 1338
FEATURE                 Location/Qualifiers
misc_feature            1..1338
                        note = Her2-Z CAR (Clone #2)
source                  1..1338
                        mol_type = other DNA
                        organism = synthetic construct
SEQUENCE: 130
atggctctgc cagtgactgc actgctgctg ccactggccc tgctgctgca cgcagctcga   60
cctgacatca gatgaccca gagccccagc agcctgagcg ccagcgtggg cgacagagtg  120
accatcacct gcaaggccag ccaggacatc aacagctgcc tgagctggtt ccagcagaag  180
cccggcaagg cccccaagac cctgatctac agagccaaca gactggtgga cggcgtgccc  240
agcagattca gcggcagcgg cagcggccag gactacaccc tgaccatcag cagcctgcag  300
cccgaggact tcgccaccta ctactgcctg cagtacgacg agttccctg gaccttcggc  360
cagggcacca aggtggagat caagggtggc ggtggatcgg gcggtggtgg atctggagga  420
ggtggctccc aggtgcagct ggtgcagagc ggcagcgagc tgaagaagcc cggcgccagc  480
gtgaaggtga gctgcaaggc cagcggctac accttcacca ctacggcgt gaactgggtg  540
agacaggccc ccggccaggg cctggagtgg atgggctgga tcaacaccca caccggcgag  600
cccacctacg ccgaggagtt caagggcaga ttcgtgttca gcctggacac cagcgtgagc  660
accgcctacc tgcagatcag cagcctgaag gccgaggaca ccgccgtgta ctactgcgcc  720
agagacgact actacgtgag agtggactac tggggccagg gcaccaccgt gaccgtgagc  780
agcgcaaaac ctaccacaac tcctgcacca cgccccccta ctccagcacc taccatcgca  840
tctcagccac tgagtctgcg accagaggcc tgccgccccg cccggggcgc ggccgtccat  900
accagagggc tggactttgc ctgcgatatc tacatttggg cccctctggc tggaacatgt  960
ggcgtgctgc tgctgtccct ggtcattact ctgtattgtc gagtgaagtt cagcaggtcc 1020
gccgacgctc ctgcatacca gcagggacag aaccagctgt ataacgagct gaatctgggc 1080
cggagagagg aatacgacgt gctggacaaa aggcggggcc gggaccccga aatgggaggg 1140
aagccacgac ggaaaaaccc caggagggc ctgtacaatg agctgcaaaa ggacaaaatg 1200
gccgaggctt attctgaaat cgggatgaag ggagagagaa ggcgcggaaa aggccacgat 1260
ggcctgtacc aggggctgag caccgctaca aaggacacct atgatgcact gcacatgcag 1320
gccctgcccc ctcggtga                                               1338

SEQ ID NO: 131          moltype = AA   length = 487
FEATURE                 Location/Qualifiers
REGION                  1..487
                        note = Her2-BBZ CAR (Clone #3)
source                  1..487
                        mol_type = protein
                        organism = synthetic construct
SEQUENCE: 131
MALPVTALLL PLALLLHAAR PDIQMTQSPS SLSASVGDRV TITCKASQDI NSYLSWFQQK   60
PGKAPKTLIY RANRLVDGVP SRFSGSGSGQ DYTLTISSLQ PEDFATYYCL QYDEFPWTFG  120
QGTKVEIKGG GGSGGGGSGG GGSQVQLVQS GSELKKPGAS VKVSCKASGY TFTNYGVNWV  180
RQAPGQGLEW MGWINTHTGE PTYAEEFKGR FVFSLDTSVS TAYLQISSLK AEDTAVYYCA  240
RDDYYVRVDY WGQGTTVTVS SAKPTTTPAP RPPTPAPTIA SQPLSLRPEA CRPAAGGAVH  300
TRGLDFACDI YIWAPLAGTC GVLLLSLVIT LYCKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                           487

SEQ ID NO: 132          moltype = DNA   length = 1464
FEATURE                 Location/Qualifiers
misc_feature            1..1464
                        note = Her2-BBZ CAR (Clone #3)
source                  1..1464
                        mol_type = other DNA
                        organism = synthetic construct
SEQUENCE: 132
atggctctgc cagtgactgc actgctgctg ccactggccc tgctgctgca cgcagctcga   60
cctgacatcc agatgaccca gagccccagc agcctgagcg ccagcgtggg cgacagagtg  120
accatcacct gcaaggccag ccaggacatc aacagctacc tgagctggtt ccagcagaag  180
cccggcaagg cccccaagac cctgatctac agagccaaca gactggtgga cggcgtgccc  240
agcagattca gcggcagcgg cagcggccag gactacaccc tgaccatcag cagcctgcag  300
cccgaggact tcgccaccta ctactgcctg cagtacgacg agttccctg gaccttcggc  360
cagggcacca aggtggagat caagggtggc ggtggatcgg gcggtggtgg atctggagga  420
ggtggctccc aggtgcagct ggtgcagagc ggcagcgagc tgaagaagcc cggcgccagc  480
gtgaaggtga gctgcaaggc cagcggctac accttcacca ctacggcgt gaactgggtg  540
agacaggccc ccggccaggg cctggagtgg atgggctgga tcaacaccca caccggcgag  600
cccacctacg ccgaggagtt caagggcaga ttcgtgttca gcctggacac cagcgtgagc  660
accgcctacc tgcagatcag cagcctgaag gccgaggaca ccgccgtgta ctactgcgcc  720
agagacgact actacgtgag agtggactac tggggccagg gcaccaccgt gaccgtgagc  780
agcgcaaaac ctaccacaac tcctgcacca cgccccccta ctccagcacc taccatcgca  840
```

```
tctcagccac tgagtctgcg accagaggcc tgccggcccg ccgcggcgg ggccgtccat    900
accagagggc tggactttgc ctgcgatatc tacatttggg cccctctggc tggaacatgt   960
ggcgtgctgc tgctgtccct ggtcattact ctgtattgta agcggggaag aaagaaactg  1020
ctgtacatct tcaaacagcc ctttatgagg cctgtgcaga ccacacagga ggaagacggc  1080
tgctcctgcc ggttccccga ggaagaggaa ggcgggtgcg aactgcgagt gaagttcagc  1140
aggtccgccg acgctcctgc ataccagcag ggacagaacc agctgtataa cgagctgaat  1200
ctgggccgga gagaggaata cgacgtgctg gacaaaaggc ggggccggga ccccgaaatg  1260
ggagggaagc cacgacggaa aaaccccag gagggcctgt acaatgagct gcaaaaggac   1320
aaaatggccg aggcttattc tgaaatcggg atgaaggag agagaaggcg cggaaaaggc   1380
cacgatggcc tgtaccaggg gctgagcacc gctacaaagg acacctatga tgcactgcac  1440
atgcaggccc tgccccctcg gtga                                         1464

SEQ ID NO: 133        moltype = AA   length = 489
FEATURE               Location/Qualifiers
REGION                1..489
                      note = Her2-28Z CAR (Clone #6)
source                1..489
                      mol_type = protein
                      organism = synthetic construct
SEQUENCE: 133
MALPVTALLL PLALLLHAAR PDIQMTQSPS SLSASVGDRV TITCKASQDI NSYLSWFQQK   60
PGKAPKTLIY RANRLVDGVP SRFSGSGSGQ DYTLTISSLQ PEDFATYYCL QYDEFPWTFG  120
QGTKVEIKGG GGSGGGGSGG GGSQVQLVQS GSELKKPGAS VKVSCKASGY TFTNYGVNWV  180
RQAPGQGLEW MGWINTHTGE PTYAEEFKGR FVFSLDTSVS TAYLQISSLK AEDTAVYYCA  240
RDDYYVRVDY WGQGTTVTVS SAKPTTTPAP RPPTPAPTIA SQPLSLRPEA CRPAAGGAVH  300
TRGLDFACDF WVLVVVGGVL ACYSLLVTVA FIIFWVRSKR SRLLHSDYMN MTPRRPGPTR  360
KHYQPYAPPR DFAAYRSRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 134        moltype = DNA   length = 1470
FEATURE               Location/Qualifiers
misc_feature          1..1470
                      note = Her2-28Z CAR (Clone #6)
source                1..1470
                      mol_type = other DNA
                      organism = synthetic construct
SEQUENCE: 134
atggctctgc cagtgactgc actgctgctg ccactggccc tgctgctgca cgcagctcga    60
cctgacatcc agatgaccca gagccccagc agcctgagcg ccagcgtggg cgacagagtg   120
accatcacct gcaaggccag ccaggacatc aacagctacc tgagctggtt ccagcagaag   180
cccggcaagg cccccaagac cctgatctac agagccaaca gactggtgga cggcgtgccc   240
agcagattca gcggcagcgg cagcggccag gactacctga ccctgaccat cagcagcctg   300
cccgaggact tcgccaccta ctactgcctg cagtacgacg agttccccctg gaccttcggc   360
cagggcacca aggtggagat caagggtggc ggtggatcgg cggtggtggg atctggagga   420
ggtggctccc aggtgcagct ggtgcagagc ggcagcgagc tgaagaagcc cggcgccagc   480
gtgaaggtga gctgcaaggc caccttcaca actacggcgt gaactgggtg   540
agacaggccc ccggccaggg cctggagtgg atgggctgga tcaacaccca caccggcgag   600
cccacctacg ccgaggagtt caagggcaga ttcgtgttca gcctggacac cagcgtgagc   660
accgcctacc tgcagatcag cagcctgaag gccgaggaca ccgccgtgta ctactgcgcc   720
agagacgact actacgtgag agtgactac tggggccagg gcaccaccgt gaccgtgagc   780
agcgcaaaac ctaccacaac tcctgcacca cgcccccta ctccagcacc taccatcgca   840
tctcagccac tgagtctgcg accagaggcc tgccggcccg ccgcggcgg ggccgtccat    900
accagagggc tggactttgc ctgcgatttt gggtcctgg tggtcgtggg aggggtgctg    960
gcatgttact cactgctggt caccgtgtgg ccttcatcatct tctgggtgcg gagcaagagg   1020
tcccgcctgc tgcacagcga ctatatgaac atgacccccc ggagaccgg cctacacg     1080
aaacattacc agcccatgc tccaccccgg gacttcgcag cttacagaag tcagtgaag   1140
ttcagcaggt ccgccgacgc tcctgcatac cagcagggac agaaccagct gtataacgag   1200
ctgaatctgg gccggagaga ggaatacgac gtgctggaca aaaggcgggg ccgggaccc   1260
gaaatgggag ggaagccacg acggaaaaac ccccaggagg gcctgtacaa tgagctgcaa   1320
aaggacaaaa tggccgaggc ttattctgaa atcgggatga aggagagag aaggcgcgga   1380
aaaggccacg atggcctgta ccaggggctg agcaccgcta caaaggacac ctatgatgca   1440
ctgcacatgc aggccctgcc ccctcggtga                                    1470

SEQ ID NO: 135        moltype = AA   length = 511
FEATURE               Location/Qualifiers
REGION                1..511
                      note = Her2-28OX40LZ CAR (Clone #14)
source                1..511
                      mol_type = protein
                      organism = synthetic construct
SEQUENCE: 135
MALPVTALLL PLALLLHAAR PDIQMTQSPS SLSASVGDRV TITCKASQDI NSYLSWFQQK   60
PGKAPKTLIY RANRLVDGVP SRFSGSGSGQ DYTLTISSLQ PEDFATYYCL QYDEFPWTFG  120
QGTKVEIKGG GGSGGGGSGG GGSQVQLVQS GSELKKPGAS VKVSCKASGY TFTNYGVNWV  180
RQAPGQGLEW MGWINTHTGE PTYAEEFKGR FVFSLDTSVS TAYLQISSLK AEDTAVYYCA  240
RDDYYVRVDY WGQGTTVTVS SAKPTTTPAP RPPTPAPTIA SQPLSLRPEA CRPAAGGAVH  300
TRGLDFACDF WVLVVVGGVL ACYSLLVTVA FIIFWVRSKR SRLLHSDYMN MTPRRPGPTR  360
KHYQPYAPPR DFAAYRSERV QPLEENVGNA ARPRFERNKR VKFSRSADAP AYQQGQNQLY  420
```

```
NELNLGRREE YDVLDKRRGR DPEMGGKPRR KNPQEGLYNE LQKDKMAEAY SEIGMKGERR    480
RGKGHDGLYQ GLSTATKDTY DALHMQALPP R                                  511

SEQ ID NO: 136         moltype = DNA  length = 1536
FEATURE                Location/Qualifiers
misc_feature           1..1536
                       note = Her2-28OX40LZ CAR (Clone #14)
source                 1..1536
                       mol_type = other DNA
                       organism = synthetic construct
SEQUENCE: 136
atggctctgc cagtgactgc actgctgctg ccactggccc tgctgctgca cgcagctcga   60
cctgacatcc agatgaccca gagccccagc agcctgagcg ccagcgtggg cgacagagtg  120
accatcacct gcaaggccag ccaggacatc aacagctacc tgagctggtt ccagcagaag  180
cccggcaagg cccccaagac cctgatctac agagccaaca gactggtgga cggcgtgccc  240
agcagattca gcggcagcgg cagcggccag gactacaccc tgaccatcag cagcctgcag  300
cccgaggact tcgccaccta ctactgcctg cagtacgacg agttcccctg gaccttcggc  360
cagggcacca aggtggagat caagggtggc ggtggatcgg gcggtggtgg atctggagga  420
ggtggctccc aggtgcagct ggtgcagagc ggcagcgagc tgaagaagcc cggcgccagc  480
gtgaaggtga gctgcaaggc cagcggctac accttcacca actacggcgt gaactggaag  540
agacaggccc ccggccaggg cctggagtgg atgggctgga tcaacaccca caccggcgag  600
cccacctacg ccgaggagtt caagggcaga ttcgtgttca gcctggacac cagcgtgagc  660
accgcctacc tgcagatcag cagcctgaag gccgaggaca ccgccgtgta ctactgcgcc  720
agagacgact actacgtgag agtggactac tggggccagg gcaccaccgt gaccgtgagc  780
agcgcaaaac ctaccacaac tcctgcacca cgcccccta ctccagcacc taccatcgca  840
tctcagccac tgagtctgcg accagaggcc tgccggcccg ccgccggcgg ggccgtccat  900
accagagggc tggactttgc ctgcgatttt tgggtcctgg tggtcgtggg aggggtgctg  960
gcatgttact cactgctggt caccgtggcc ttcatcatct tctgggtgcg gagcaagagg 1020
tcccgcctgc tgcacagcga ctatatgaac atgacccac ggagaccgg ccctacacgg 1080
aaacattacc agccctatgc tccaccccgg gacttcgcca cttacagaag tgaaagaggt 1140
cagcccctgg aagagaatgt cgggaatgcc gctcgcccca gatttgaaag gaacaaacga 1200
gtgaagttca gcaggtccgc cgacgctcct gcataccagc agggacagaa ccagctgtat 1260
aacgagctga atctgggccg gagagaggaa tacgacgtgc tggacaaaag gcggggccgg 1320
gaccccgaaa tgggagggaa gccacgacgg aaaaacccc aggagggcct gtacaatgag 1380
ctgcaaaagg acaaaatggc cgaggcttat tctgaaatcg ggatgaaggg agagagaagg 1440
cgcggaaaag gccacgatgg cctgtaccag gggctgagca ccgctacaaa ggacacctat 1500
gatgcactgc acatgcaggc cctgcccct cggtga                            1536
```

ANTI-HER2 ANTIBODY OR ANTIGEN-BINDING FRAGMENT THEREOF, AND CHIMERIC ANTIGEN RECEPTOR COMPRISING SAME

CROSS-REFERENCE TO RELATED APPLICATIONS

This application is a continuation application of and claims the benefit of priority to U.S. application Ser. No. 18/298,310, filed on Apr. 10, 2023, which is a divisional application of and claims the benefit of priority to U.S. application Ser. No. 16/881,650, filed on May 22, 2020, now U.S. Pat. No. 11,649,294, which is a continuation-in-part application of and claims the benefit of priority to U.S. application Ser. No. 16/764,276, filed on Sep. 28, 2020, which is a National Stage of International Application No. PCT/KR2018/013928, filed on Nov. 14, 2018, claiming priority based on Korean Patent Application No. 10-2017-0151841, filed Nov. 14, 2017, the contents of which are hereby incorporated by reference.

REFERENCE TO SEQUENCE LISTING SUBMITTED ELECTRONICALLY

This application contains a Sequence Listing that has been submitted electronically as an XML file named 49755-0034003_SL_ST26.xml. The XML file, created on Mar. 27, 2024, is 214,314 bytes in size. The material in the XML file is hereby incorporated by reference in its entirety.

TECHNICAL FIELD

The research was conducted under the support of the Ministry of Trade, Industry and Energy of Korea with the project number 1415118385. The R&D management agency of the project is the Korea Institute for Advancement of Technology, the R&D project title is "Global innovation technology alliance", and the research title is "Development of global antibody drug based on novel epitope screening platform technology". The research was conducted by AbClon Inc. from Nov. 1, 2011 until Oct. 31, 2014.

This application claims the priority of Korean Patent Application No. 10-2017-0151841 filed on Nov. 14, 2017 in the Korean Intellectual Property Office, the disclosure of which is incorporated herein by reference in its entirety.

The present disclosure relates to a novel anti-HER2 antibody or an antigen-binding fragment thereof, a chimeric antigen receptor including the same, and uses thereof.

BACKGROUND ART

The Her2/neu (ErbB2) gene encodes a 185-kDa transmembrane glycoprotein that belongs to the family of epidermal growth factor receptors (EGFRs). The Her2 protein is composed of an extracellular domain consisting of 620 amino acid residues, a transmembrane domain 23 amino acid residues, and an intracellular domain with tyrosine kinase activity, consisting of 490 amino acid residues (Akiyama T, et al., Science, 232 (4758): 1644-1646 (1986)).

Anti-HER2 antibodies with various characteristics have been described: Tagliabue et al., Int. J. Cancer 47: 933-937 (1991); McKenzie et al., Oncogene 4: 543-548 (1989); Maier et al., Cancer Res. 51: 5361-5369 (1991); Bacus et al., Molecular Carcinogenesis 3: 350-362 (1990); Stancovski et al., PNAS USA 88: 8691-8695 (1991); Bacus et al., Cancer Research 52: 2580-2589 (1992); Xu et al., Int. J. Cancer 53: 401-408 (1993); WO94/00136; Kasprzyk et al., Cancer Research 52: 2771-2776 (1992); Hancock et al., Cancer Res. 51: 4575-4580 (1991); Shawver et al., Cancer Res. 54: 1367-1373 (1994); Arteaga et al., Cancer Res. 54: 3758-3765 (1994); Harwerth et al., J. Biol. Chem. 267: 15160-15167 (1992); U.S. Pat. No. 5,783,186; Kao et al., US Patent Application Publication No. 2009/0285837 (2009); Ross et al., The Oncologist 8: 307-325 (2003); and Klapper et al., Oncogene 14: 2099-2109 (1997).

The most commercially successful anti-HER2 antibody is trastuzumab antibody (commercially available as Herceptin™, U.S. Pat. No. 5,821,337) and many researches have been conducted thereon: Sapino, A., et al., Annals of Oncology (2007) 18: 1963-1968; Bussolati, G, et al., British Journal of Cancer (2005) 92, 1261-1267; and Glazyrin A, et al., J Histology & Cytochemistry (2007) 55 (1): 25-33.

Although the trastuzumab antibody has been commercially successful, use of the trastuzumab antibody for therapeutic purposes is limited because there are various cancer cells which have non-reactivity (or resistance) to the antibody or have reduced sensitivity. Accordingly, there have been attempts to resolve the therapeutic problem of the antibody.

For example, U.S. Pat. No. 7,674,460 discloses a method for increasing the HER2 sensitivity of cancer cells using an HER2 antagonist such as the trastuzumab antibody and a PC cell-derived growth factor (PCDGF) antagonist. WO 2011/127297 discloses a method for inhibiting the proliferation of trastuzumab-resistant tumor cells using a combination of a FoxM1 inhibitor and the trastuzumab antibody.

US Patent Application Publication No. 2010-0183604 discloses a method for treating trastuzumab-resistant cancer using a cofilin inhibitor, a PAK1 inhibitor, a LIMK inhibitor, an RHO inhibitor, a ROCK1 inhibitor or a ROCK2 inhibitor.

DISCLOSURE

Technical Problem

The inventors of the present disclosure have made efforts to develop a novel antibody which is capable of preventing or treating cancer (particularly, breast cancer and gastric cancer), exhibits better killing ability (or proliferation-inhibiting ability) for cancer cells which have non-reactivity (or resistance) to the trastuzumab antibody or have reduced sensitivity, and is capable of preventing or treating cancer with improved anticancer activity when co-administered with the trastuzumab antibody as compared to single administration of trastuzumab. As a result, they have developed a novel antibody which exhibits better killing ability for HER2-overexpressed cancer cells on which the trastuzumab antibody hardly acts, or exhibits improved anticancer activity when co-administered with the trastuzumab antibody, and have completed the present disclosure.

SUMMARY OF THE INVENTION

The present disclosure provides an antibody or an antigen binding fragment thereof against HER2 (human epidermal growth factor receptor 2) comprising any one of: (a) a heavy chain variable region comprising a CDRH1 of SEQ ID NO 1, a CDRH2 of SEQ ID NO 2 and a CDRH3 of SEQ ID NO 3, and a light chain variable region comprising a CDRL1 of SEQ ID NO 4, a CDRL2 of SEQ ID NO 5 and a CDRL3 of SEQ ID NO 6; (b) a heavy chain variable region comprising a CDRH1 of SEQ ID NO 7, a CDRH2 of SEQ ID NO 8 and a CDRH3 of SEQ ID NO 9, 71 or 72, and a light chain variable region comprising a CDRL1 of SEQ ID NO 10, a CDRL2 of SEQ ID NO 11 and a CDRL3 of SEQ ID NO 12, 73 or 74; (c) a heavy chain variable region comprising a CDRH1 of SEQ ID NO 13, a CDRH2 of SEQ ID NO 14 and a CDRH3 of SEQ ID NO 15, and a light chain variable region comprising a CDRL1 of SEQ ID NO 16, a CDRL2 of SEQ ID NO 17 and a CDRL3 of SEQ ID NO 18; (d) a heavy chain variable region comprising a CDRH1 of SEQ ID NO 19, a CDRH2 of SEQ ID NO 20 and a CDRH3 of SEQ ID NO 21, and a light chain variable region comprising a CDRL1 of SEQ ID NO 22, a CDRL2 of SEQ ID NO 23 and a CDRL3 of SEQ ID NO 24; or (d) a heavy chain variable region comprising a CDRH1 of SEQ ID NO 25, a CDRH2 of SEQ ID NO 26 and a CDRH3 of SEQ ID NO 27, and a light chain variable region comprising a CDRL1 of SEQ ID NO 28, a CDRL2 of SEQ ID NO 29 and a CDRL3 of SEQ ID NO 30.

In some aspects of the disclosure, the heavy chain variable region of (a) comprises an amino acid sequence of SEQ ID NO 31 or 75; the heavy chain variable region of (b) comprises an amino acid sequence of SEQ ID NO 39, 83, 87, 95 or 103; the heavy chain variable region of (c) comprises an amino acid sequence of SEQ ID NO 47; the heavy chain variable region of (d) comprises an amino acid sequence of SEQ ID NO 55; and the heavy chain variable region of (e) comprises an amino acid sequence of SEQ ID NO 63 or 79.

In some aspects of the disclosure, the light chain variable region of (a) comprises an amino acid sequence of SEQ ID NO 35 or 77; the light chain variable region of (b) comprises an amino acid sequence of SEQ ID NO 43, 85, 91, 99 or 107; the light chain variable region of (c) comprises an amino acid sequence of SEQ ID NO 51; the light chain variable region of (d) comprises an amino acid sequence of SEQ ID NO 59; and the light chain variable region of (e) comprises an amino acid sequence of SEQ ID NO 67 or 81.

In some aspects of the disclosure, the antibody or the antigen-binding fragment thereof comprising (a) comprises a heavy chain comprising an amino acid sequence of SEQ ID NO 33; the antibody or the antigen-binding fragment thereof comprising (b) comprises a heavy chain comprising an amino acid sequence of SEQ ID NO 41, 89, 97 or 105; the antibody or the antigen-binding fragment thereof comprising (c) comprises a heavy chain comprising an amino acid sequence of SEQ ID NO 49; the antibody or the antigen-binding fragment thereof comprising (d) comprises a heavy chain comprising an amino acid sequence of SEQ ID NO 57; and the antibody or the antigen-binding fragment thereof comprising (e) comprises a heavy chain comprising an amino acid sequence of SEQ ID NO 65.

In some aspects of the disclosure, the antibody or the antigen-binding fragment thereof comprising (a) comprises a light chain comprising an amino acid sequence of SEQ ID NO 37; the antibody or the antigen-binding fragment thereof comprising (b) comprises a light chain comprising an amino acid sequence of SEQ ID NO 45, 93, 101 or 109; the antibody or the antigen-binding fragment thereof comprising (c) comprises a light chain comprising an amino acid sequence of SEQ ID NO 53; the antibody or the antigen-binding fragment thereof comprising (d) comprises a light chain comprising an amino acid sequence of SEQ ID NO 61; and the antibody or the antigen-binding fragment thereof comprising (e) comprises a light chain comprising an amino acid sequence of SEQ ID NO 69.

The present disclosure further provides a fusion protein comprising the antibody or the antigen-binding fragment as described herein.

The present disclosure further provides a chimeric antigen receptor polypeptide comprising an HER2-binding domain; a transmembrane domain (TM); a costimulatory domain; and an intracellular signaling domain (ICD).

In some aspects of the disclosure, the HER2-binding domain comprises the antibody or the antigen-binding fragment thereof as described herein.

In some aspects of the disclosure, the transmembrane domain is a transmembrane domain of a protein selected from a group consisting of T-cell receptor alpha, beta or zeta chain, CD28, CD3 epsilon, CD45, CD4, CD5, CD8, CD9, CD16, CD22, CD33, CD37, CD64, CD80, CD86, CD134, CD137 and CD154.

In some aspects of the disclosure, the costimulatory domain is a functional signaling domain obtained from a protein selected from a group consisting of MHC class I molecule, TNF receptor protein, immunoglobulin-like protein, cytokine receptor, integrin, signaling lymphocytic activation molecule (SLAM), activating NK cell receptor, BTLA (B- and T-lymphocyte attenuator), Toll-like ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand binding specifically to CD83.

In some aspects of the disclosure, the intracellular signaling domain comprises a functional signaling domain of 4-1BB, CD28, OX40 or CD3 zeta, or a combination thereof.

In some aspects of the disclosure, the intracellular signaling domain comprises a functional signaling domain of OX40 ligand.

The present disclosure further provides a nucleic acid molecule encoding the anti-HER2 antibody or the antigen-binding fragment thereof as described herein.

The present disclosure further provides a nucleic acid molecule encoding the chimeric antigen receptor polypeptide as described herein.

The present disclosure further provides a recombinant vector comprising the nucleic acid molecule encoding the anti-HER2 antibody or the antigen-binding fragment thereof as described herein or the chimeric antigen receptor polypeptide as described herein.

The present disclosure further provides a host cell transformed with the recombinant vector as described herein.

The present disclosure further provides an effector cell expressing the chimeric antigen receptor polypeptide as described herein.

In some aspects of the disclosure, the effector cell is selected from a group consisting of a dendritic cell, a killer dendritic cell, a mast cell, a natural killer cell, a B lymphocyte, a T lymphocyte, a macrophage and precursor cells thereof.

In some aspects of the disclosure, the T lymphocyte is selected from a group consisting of an inflammatory T lymphocyte, a cytotoxic T lymphocyte, a regulatory T lymphocyte or a helper T lymphocyte.

The present disclosure further provides a pharmaceutical composition for preventing or treating cancer, comprising a pharmaceutically effective amount of the anti-HER2 antibody or the antigen-binding fragment thereof as described herein a pharmaceutically acceptable carrier.

The present disclosure further provides a pharmaceutical composition for treating cancer, comprising the effector cell expressing the chimeric antigen receptor polypeptide as described herein.

In some aspects of the disclosure, the cancer is breast cancer, ovarian cancer, gastric cancer, lung cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer or ureteral cancer.

In some aspects of the disclosure, the pharmaceutical composition further comprises the trastuzumab antibody.

The present disclosure further provides a kit for diagnosing cancer, comprising the anti-HER2 antibody or the antigen-binding fragment thereof as described herein.

The present disclosure further provides a chimeric antigen receptor comprising an extracellular domain that binds Her2, wherein the extracellular domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)).

In some aspects of the disclosure, the chimeric antigen receptor further comprises an extracellular signaling domain linked to the extracellular domain; a hinge domain linked to the extracellular domain; a transmembrane domain linked to the hinge domain; and
  an intracellular stimulatory signal linked to the hinge domain.

In some aspects of the disclosure, the extracellular signaling domain comprises an amino acid sequence having at least 80%, at least 85%, at least 90% at least 91%, at least 92%, at least 93%, at least 94%, at least 95%, at least 96%, at least 97%, at least 98%, or at least 99% sequence identity with SEQ ID NO: 111 (CD8a signal peptide). In some aspects, the extracellular signaling domain comprises SEQ ID NO: 111 (CD8a signal peptide).

In some aspects of the disclosure, the hinge domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 115 (CD8α hinge). In some aspects of the disclosure, the hinge domain comprises SEQ ID NO: 115 (CD8α hinge).

In some aspects of the disclosure, the transmembrane domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 117 (CD8α TM) or SEQ ID NO: 119 (CD28 TM). In some aspects of the disclosure, the transmembrane domain comprises SEQ ID NO: 117 CD8α TM) or SEQ ID NO: 119 (CD28 TM).

In some aspects of the disclosure, the intracellular stimulatory signal comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 121 (CD3-ζ). In some aspects, the intracellular stimulatory signal comprises SEQ ID NO: 121 (CD3-ζ).

In some aspects of the disclosure, the chimeric antigen receptor further comprises a second intracellular stimulatory signal, wherein the second intracellular stimulatory signal comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 123 (4-1BB) or SEQ ID NO: 125 (CD28). In some aspects of the disclosure, the second intracellular stimulatory signal comprises SEQ ID NO: 123 (4-1BB) or SEQ ID NO: 125 (CD28).

In some aspects of the disclosure, the chimeric antigen receptor further comprises a third intracellular stimulatory signal, wherein the third intracellular stimulatory signal comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 127 (OX40L). In some aspects of the disclosure, wherein the third intracellular stimulatory signal comprises SEQ ID NO: 127 (OX40L).

In some aspects of the disclosure, the chimeric antigen receptor comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 129 (Clone 2), SEQ ID NO: 131 (Clone 3), SEQ ID NO: 133 (Clone 6), or SEQ ID NO: 135 (Clone 14). In some aspects of the disclosure, the chimeric antigen receptor comprises SEQ ID NO: 129 (Clone 2), SEQ ID NO: 131 (Clone 3), SEQ ID NO: 133 (Clone 6), or SEQ ID NO: 135 (Clone 14).

The present disclosure further provides a nucleic acid molecule encoding the chimeric antigen receptor having an extracellular domain comprising an amino acid sequence with at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)) as described herein.

The present disclosure further provides a vector comprising the nucleic acid molecule encoding the chimeric antigen receptor having an extracellular domain comprising an amino acid sequence with at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)) as described herein.

The present disclosure further provides an immune cell expressing the chimeric antigen having an extracellular domain comprising an amino acid sequence with at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)) as described herein.

In some aspects of the disclosure, the immune cell is a natural killer cell.

The present disclosure further provides a pharmaceutical composition comprising the immune cell as described herein and a pharmaceutically acceptable carrier.

The present disclosure further provides a method for treating cancer comprising administering to a subject in need thereof a therapeutically effective amount of the pharmaceutical composition as described herein.

In some aspects of the disclosure, the cancer is selected from the group consisting of breast cancer, ovarian cancer, gastric cancer, lung cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer and ureteral cancer.

BRIEF DESCRIPTION OF DRAWINGS

FIG. 7 is a table providing a summary of HER2-CAR constructs according to the present disclosure.

FIGS. 8A-8C are line graphs showing the results of a cell killing assay (Calcein releasing cytotoxicity assay) assessing the cytotoxicity of cord-blood derived NK cells (CBNKs) expressing HER2-CAR constructs against HER2 positive target cancer cell lines.

DETAILED DESCRIPTION OF THE INVENTION

Figure 1:
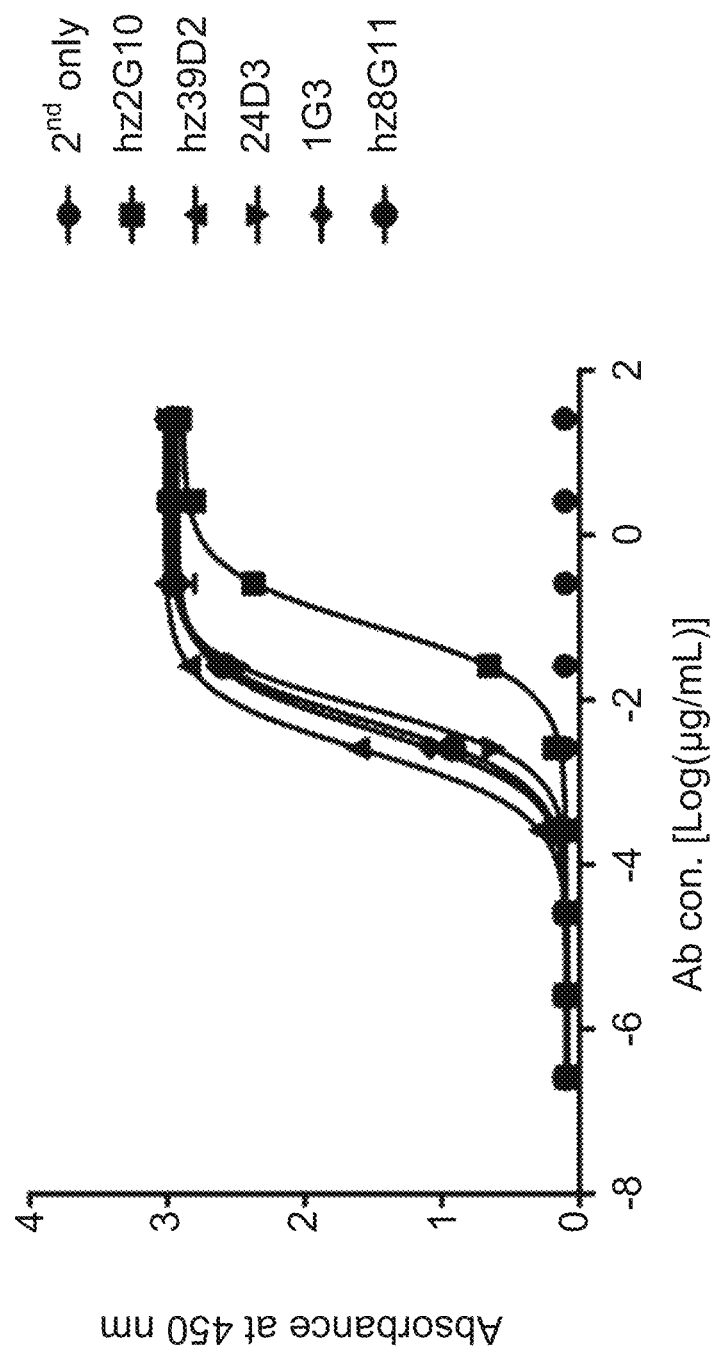
FIG. 1 is a line graph showing the a results of analyzing the affinity of hz2G10, hz39D2, 24D3, 1G3 and hz8G11 clones for the HER2-ECD-Fc antigen by ELISA.

The present disclosure is directed to providing an antibody (anti-HER2 antibody) against HER2 (human epidermal growth factor receptor 2) or an antigen-binding fragment thereof.

The present disclosure is also directed to providing a fusion protein including the anti-HER2 antibody or an antigen-binding fragment thereof.

The present disclosure is also directed to providing a chimeric antigen receptor (CAR) including the anti-HER2 antibody or an antigen-binding fragment thereof and an effector cell expressing the same.

The present disclosure is also directed to providing a nucleic acid molecule encoding the anti-HER2 antibody or an antigen-binding fragment thereof; or the chimeric antigen receptor.

The present disclosure is also directed to providing a recombinant vector including the nucleic acid molecule.

The present disclosure is also directed to providing a host cell transformed with the recombinant vector.

The present disclosure is also directed to providing a pharmaceutical composition for preventing or treating cancer, which contains the anti-HER2 antibody or an antigen-binding fragment thereof.

The present disclosure is also directed to providing a kit for diagnosing cancer, which includes the anti-HER2 antibody or an antigen-binding fragment thereof.

The present disclosure is also directed to providing a method for preventing or treating cancer by administering a composition containing the anti-HER2 antibody or an antigen-binding fragment thereof to a subject.

The present disclosure is also directed to providing a method for treating a disease related with HER2 overexpression (e.g., cancer) by administering an effector cell expressing the chimeric antigen receptor to a subject.

Technical Solution

The present disclosure provides an antibody binding specifically to HER2 (human epidermal growth factor receptor 2) and modified antibodies thereof that have undergone affinity maturation.

A first aspect of the present disclosure provides an antibody against HER2 (human epidermal growth factor receptor 2) including the followings or an antigen-binding fragment thereof:
(a) a heavy chain variable region including the following heavy chain CDR (complementarity-determining region) amino acid sequences:
CDRH1 of SEQ ID NO 1, CDRH2 of SEQ ID NO 2 and CDRH3 of SEQ ID NO 3; and
(b) a light chain variable region including the following light chain CDR amino acid sequences:
CDRL1 of SEQ ID NO 4, CDRL2 of SEQ ID NO 5 and CDRL3 of SEQ ID NO 6.

A second aspect of the present disclosure provides an antibody against HER2 (human epidermal growth factor receptor 2) including the followings or an antigen-binding fragment thereof:
(a) a heavy chain variable region including the following heavy chain CDR (complementarity-determining region) amino acid sequences:
CDRH1 of SEQ ID NO 7, CDRH2 of SEQ ID NO 8 and CDRH3 of SEQ ID NO 9, 71 or 72; and
(b) a light chain variable region including the following light chain CDR amino acid sequences:
CDRL1 of SEQ ID NO 10, CDRL2 of SEQ ID NO 11 and CDRL3 of SEQ ID NO 12, 73 or 74.

A third aspect of the present disclosure provides an antibody against HER2 (human epidermal growth factor receptor 2) including the following or an antigen-binding fragment thereof:
(a) a heavy chain variable region including the following heavy chain CDR (complementarity-determining region) amino acid sequences:
CDRH1 of SEQ ID NO 13, CDRH2 of SEQ ID NO 14 and CDRH3 of SEQ ID NO 15; and
(b) a light chain variable region including the following light chain CDR amino acid sequences:
CDRL1 of SEQ ID NO 16, CDRL2 of SEQ ID NO 17 and CDRL3 of SEQ ID NO 18.

A fourth aspect of the present disclosure provides an antibody against HER2 (human epidermal growth factor receptor 2) including the following or an antigen-binding fragment thereof:
(a) a heavy chain variable region including the following heavy chain CDR (complementarity-determining region) amino acid sequences:
CDRH1 of SEQ ID NO 19, CDRH2 of SEQ ID NO 20 and CDRH3 of SEQ ID NO 21; and
(b) a light chain variable region including the following light chain CDR amino acid sequences:
CDRL1 of SEQ ID NO 22, CDRL2 of SEQ ID NO 23 and CDRL3 of SEQ ID NO 24.

A fifth aspect of the present disclosure provides an antibody against HER2 (human epidermal growth factor receptor 2) including the following or an antigen-binding fragment thereof:
(a) a heavy chain variable region including the following heavy chain CDR (complementarity-determining region) amino acid sequences:
CDRH1 of SEQ ID NO 25, CDRH2 of SEQ ID NO 26 and CDRH3 of SEQ ID NO 27; and
(b) a light chain variable region including the following light chain CDR amino acid sequences:
CDRL1 of SEQ ID NO 28, CDRL2 of SEQ ID NO 29 and CDRL3 of SEQ ID NO 30.

The antibody of the first aspect, the antibody of the second aspect, the antibody of the third aspect, the antibody of the fourth aspect and the antibody of the fifth aspect are referred to, respectively, as 2G10, 39D2, 24D3, 1G3 and 8G11 antibodies. They are mouse antibodies or chimeric antibodies. Among them, the humanized antibodies are expressed with the prefix hz, e.g., as hz2G10, hz39D2 and hz8G11 antibodies.

The inventors of the present disclosure have made efforts to develop a novel antibody which is capable of preventing or treating cancer (particularly, breast cancer and gastric cancer), exhibits better killing ability (or proliferation-inhibiting ability) for cancer cells which have non-reactivity (or resistance) to the trastuzumab antibody or have reduced sensitivity, and is capable of preventing or treating cancer with improved anticancer activity when co-administered with the trastuzumab antibody as compared to single administration of trastuzumab. As a result, they have developed a novel antibody which exhibits better killing ability for HER2-overexpressed cancer cells on which the trastuzumab antibody hardly acts, or exhibits improved anticancer activity when co-administered with the trastuzumab antibody, and have completed the present disclosure.

The antibody of the present disclosure or an antigen-binding fragment thereof has a specific binding ability for HER2. In particular, among the antibodies of the present disclosure, hz2G10 and hz39D2 bind to an epitope in domain 1 of domains 1-4 of HER2, 24D3 binds to an epitope in domain 3, and 1G3 and hz8G11 bind to an epitope in domain 4, like trastuzumab, which is different from the epitope to which trastuzumab binds.

In the present disclosure, the term "trastuzumab" refers to an antibody disclosed in U.S. Pat. No. 5,821,337.

The antibody of the present disclosure has superior killing ability or proliferation-inhibiting ability for cancer cells which have non-reactivity (or resistance) to the trastuzumab antibody or have reduced sensitivity, when used either alone or in combination with trastuzumab. In the present disclosure, the terms "killing", "proliferation-inhibiting" or "growth-inhibiting" are used interchangeable with the same meaning with regard to cancer cells.

In the present disclosure, the term "antibody" refers to an antibody specific for HER2, and includes not only the whole antibody but also an antigen-binding fragment of the antibody molecule.

A whole antibody has two full-length light chains and two full-length heavy chains. The light chains and heavy chains are connected by disulfide bonds. The constant region of the heavy chain has gamma ($\gamma$), mu ($\mu$), alpha ($\alpha$), delta ($\delta$) and epsilon ($\epsilon$) types, and has subclasses gamma1 ($\gamma$1), gamma2 ($\gamma$2), gamma3 ($\gamma$3), gamma4 ($\gamma$4), alpha1 ($\alpha$1) and alpha2 ($\alpha$2). The constant region of the light chain has kappa ($\kappa$) and lambda ($\lambda$) types.

In the present disclosure, the term "antigen-binding fragment" refers to a fragment having antigen-binding ability, and includes Fab, F(ab'), F(ab')$_2$, Fv, etc. Among the antibody fragments, Fab (fragment antigen-binding) has a structure having a variable region of the light and heavy chains, a constant region of the light chain and the first constant region ($C_{H1}$) of the heavy chain and has one antigen-binding site. Fab' differs from Fab in that it has a hinge region including at least one cysteine residue at the C-terminus of the heavy chain CH1 domain. In the F(ab')$_2$ antibody, a cysteine residue in the hinge region of Fab' forms a disulfide bond. Recombinant techniques for generating Fv fragments with minimal antibody fragments in which Fv has only the heavy chain variable region and the light chain variable region are known in the related art. A double-chain variable fragment (dcFv) is linked to a heavy chain variable region and a light chain variable region via a non-covalent bond, and a single-chin variable fragment (scFv) is generally linked to covalently to the variable region of a heavy chain via a peptide linker, or to the C-terminus, to form a dimer such as the double-chain Fv. These antibody fragments can be obtained using proteases (for example, Fab can be obtained by cleaving a whole antibody with papain, and the F(ab')2 fragment can be obtained by cleaving with pepsin), or can be prepared using genetic recombination techniques.

Specifically, in the present disclosure, the antibody includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (dsFv), an anti-idiotypic (anti-Id) antibody, and epitope-binding fragments of these antibodies, although not being limited thereto.

In the present disclosure, the term "heavy chain" encompasses a full-length heavy chain including a variable region domain VH and three constant region domains $C_{H1}$, $C_{H2}$ and $C_{H3}$, including an amino acid sequence having a variable region sequence sufficient for conferring specificity to an antigen, and fragments thereof. Also, in the present disclosure, the term "light chain" encompasses a full-length light chain including a variable region domain $V_L$ and a constant region domain $C_L$, including an amino acid sequence having a variable region sequence sufficient for conferring specificity to an antigen, and fragments thereof.

In the present disclosure, the term "variable region" or "variable domain" refers to a domain of an antibody heavy chain or light chain associated with binding of an antibody to an antigen. In general, the variable domains of a heavy chain and a light chain ($V_H$ and $V_L$, respectively) of a native antibody have similar structures, and each domain includes four conserved framework region (FRs) and three hypervariable regions (HVRs) (Kindt et al., Kuby Immunology, 6th ed., W.H. Freeman and Co., page 91 (2007)).

In the present disclosure, the term "CDR (complementarity-determining region)" refers to the amino acid sequence of the hypervariable region of a heavy chain and a light chain of an immunoglobulin (Kabat et al., Sequences of Proteins of Immunological Interest, 4th ed., U.S. Department of Health and Human Services, National Institutes of Health (1987)). Each of the heavy chain (CDRH1, CDRH2 and CDRH3) and the light chain (CDRL1, CDRL2 and CDRL3) includes three CDRs. The CDR provides major contact residue for binding of an antibody to an antigen or an epitope.

In the present disclosure, the term "framework region" or "FR" refers to a variable domain residue other than a hypervariable region (HVR) residue. The FR of a variable domain generally consists of four FR domains: FR1, FR2, FR3 and FR4. Accordingly, the HVR and FR sequences generally appear in the following order in $V_H$:

FRH1 (framework region 1 of heavy chain)-CDRH1 (complementarity-determining region 1 of heavy chain)-FRH2-CDRH2-FRH3-CDRH3-FRH4.

And, the HVR and FR sequences generally appear in the following order in $V_L$ (or $V_k$):

FRL1 (framework region 1 of light chain)-CDRL1 (complementarity-determining region 1 of light chain)-FRL2-CDRL2-FRL3-CDRL3-FRL4.

In the present disclosure, the term "specific binding" means that an antibody or an antigen-binding fragment thereof, or another construct such as scFv forms a relatively stable complex with an antigen under physiological conditions. The specific binding may be characterized by an equilibrium dissociation constant of about $1\times10^{-6}$ M or smaller (e.g., the smaller the $K_d$, the tighter the binding). Methods for determining if two molecules bind specifically are well known in the art, for example, equilibrium dialysis, surface plasmon resonance, etc.

In the present disclosure, the term "affinity" refers to the strength of the sum of noncovalent interactions between a single binding site of a molecule (e.g., an antibody) and its binding partner (e.g., an antigen). Unless specified otherwise, "binding affinity" refers to intrinsic binding affinity which reflects a 1:1 interaction between the members of a binding pair (e.g., an antibody and an antigen). The affinity of a molecule X for its partner Y may generally be represented by a dissociation constant ($K_d$). The affinity can be measured by common methods known in the art, including those described in the present disclosure.

In the present disclosure, the "human antibody" or "humanized antibody" possesses an amino acid sequence which corresponds to an antibody produced by human or a human cell, or an antibody derived from a non-human source that utilizes human antibody repertoires or other human antibody-encoding sequences.

In the present disclosure, the term "chimeric antibody" refers to an antibody in which a portion of the heavy chain and/or light chain is derived from a particular source or species while the remainder of the heavy chain and/or light chain is derived from a different source or species.

The anti-HER2 antibody of the present disclosure or an antigen-binding fragment thereof may include variants of the amino acid sequences described in the attached sequence listings within the scope of specifically recognizing HER2. For example, the amino acid sequence of an antibody may be modified to improve the binding affinity and/or other biological properties of the antibody. Such modification includes, for example, deletion, insertion and/or substitution of the amino acid sequence residue of the antibody.

Such amino acid variation is made based on the relative similarity of amino acid side chain substituents, such as hydrophobicity, hydrophilicity, charge, size, etc. From analysis of the size, shape and type of amino acid side chain substituents, it is recognized that arginine, lysine and histidine are positively charged residues; alanine, glycine and serine have similar sizes; and phenylalanine, tryptophan and tyrosine have similar shapes. Based on these considerations, it is thus recognized that arginine, lysine and histidine; alanine, glycine and serine; and phenylalanine, tryptophan and tyrosine are biologically functional equivalents.

For introduction of mutation, the hydropathy indices of amino acids may be considered. Each amino acid is assigned a hydropathy index according to its hydrophobicity and charge: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydropathy indices of amino acids are very important in imparting the interactive biological function of proteins. It is well known that similar biological activity can be retained when substitution is made with an amino acid having a similar hydropathy index. In this regard, when mutation is introduced, substitution is made between amino acids showing difference in the hydropathy index preferably within ±2, more preferably within ±1, even more preferably within ±0.5.

Meanwhile, it is also well known that substitution between amino acids having similar hydrophilicity values leads to proteins with equivalent biological activity. As disclosed in U.S. Pat. No. 4,554,101, the following hydrophilicity values are assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In this regard, when mutation is introduced, substitution is made between amino acids showing difference in the hydrophilicity value preferably within ±2, more preferably within ±1, even more preferably within ±0.5.

Amino acid substitutions in proteins that do not entirely alter the activity of the molecules are known in the art (H. Neurath, R. L. Hill, The Proteins, Academic Press, New York, 1979). The most commonly occurring substitutions are substitutions between the following amino acid residues: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly.

In an exemplary embodiment of the present disclosure, the heavy chain variable region of the hz2G10 antibody and the 2G10 antibody respectively includes amino acid sequences of SEQ ID NO 31 and 32.

In an exemplary embodiment of the present disclosure, the light chain variable region of the hz2G10 antibody and the 2G10 antibody respectively includes amino acid sequences of SEQ ID NO 35 and 77.

In an exemplary embodiment of the present disclosure, the heavy chain variable region of the hz39D2 antibody and the 39D2 antibody respectively includes amino acid sequences of SEQ ID NO 39 and 83.

In an exemplary embodiment of the present disclosure, the light chain variable region of the hz39D2 antibody and the 39D2 antibody respectively includes amino acid sequences of SEQ ID NO 43 and 85.

In an exemplary embodiment of the present disclosure, the heavy chain variable region of the 24D3 antibody includes an amino acid sequence of SEQ ID NO 47.

In an exemplary embodiment of the present disclosure, the light chain variable region of the 24D3 antibody includes an amino acid sequence of SEQ ID NO 51.

In an exemplary embodiment of the present disclosure, the heavy chain variable region of the 1G3 antibody includes an amino acid sequence of SEQ ID NO 55.

In an exemplary embodiment of the present disclosure, the light chain variable region of the 1G3 antibody includes an amino acid sequence of SEQ ID NO 59.

In an exemplary embodiment of the present disclosure, the heavy chain variable region of the hz8G11 antibody and the 8G11 antibody respectively includes amino acid sequences of SEQ ID NO 63 and 79.

In an exemplary embodiment of the present disclosure, the light chain variable region of the hz8G11 antibody and the 8G11 antibody respectively includes amino acid sequences of SEQ ID NO 67 and 81.

The antibody of the present disclosure includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (dsFv), an anti-idiotypic (anti-Id) antibody, and epitope-binding fragments of these antibodies, although not being limited thereto.

Meanwhile, the antibody of the present disclosure is unique in that its CDR sequence has very low homology (similarity) to the CDR sequences of existing anti-HER2 antibodies. For example, as a result of BLAST search for hz2G10 from among the antibodies of the present disclosure, the highest CDR sequence homology of the antibody of the present disclosure to the antibodies disclosed in U.S. Pat. Nos. 8,314,213 and 8,404,811 was less than 50%. In addition, the antibodies disclosed in U.S. Pat. Nos. 8,314,213 and 8,404,811 bind to CD25 and EGFL7, respectively, and are different from the antibody of the present disclosure in their targets.

In addition, the anti-HER2 antibody of the present disclosure or an antigen-binding fragment thereof encompasses an anti-HER2 antibody including a slight change in the amino acid sequence described above, including the modification that hardly affects the tertiary structure and function of the antibody, or an antigen-binding fragment thereof. Accordingly, in some exemplary embodiments, the antibody may have an amino acid sequence with at least 90%, 93%, 95% or 98% similarity to the above-described sequence.

Also, in the present disclosure, the heavy chain variable region and the light chain variable region of the antibody or an antigen-binding fragment thereof may be linked by a linker composed of an amino acid sequence represented by the general formula $(G_nS_m)_p$ or $(S_mG_n)_p$.

In the formula, n, m and p satisfy the followings:
n is an integer from 1 to 7;
m is an integer from 0 to 7;
n+m is an integer which is 8 or smaller; and
p is an integer from 1 to 7.

In a specific exemplary embodiment of the present disclosure, n=1-5 and m=0-5. In a more specific exemplary embodiment, n=4 and m=1. In a further more specific exemplary embodiment, the linker is $(G_4S)_3$ or $(S_4G)_3$.

In another exemplary embodiment, the linker is VDGS. In another exemplary embodiment, the linker is ASGS.

In addition, the light chain variable region and the heavy chain variable region of the antibody according to the present disclosure or an antigen-binding fragment may in the following orientations:
light chain variable region-linker-heavy chain variable region; or
heavy chain variable region-linker-light chain variable region.

Another aspect of the present disclosure provides a fusion protein including an anti-HER2 antibody or an antigen-binding fragment thereof.

In the present disclosure, the fusion protein is prepared for the productivity purification efficiency, improved biological activity, increased stability, improved folding and/or binding to a functional moiety for additional function of the anti-HER2 antibody of the present disclosure or an antigen-binding fragment thereof. The fusion protein may be formed as two or more polypeptide chains are linked by a covalent bond, or may be in the form of a conjugate wherein two or more polypeptide chains are linked by chemical conjugation.

Another aspect of the present disclosure provides a chimeric antigen receptor polypeptide including the followings:
(a) an HER2-binding domain;
(b) a transmembrane domain (TM);
(c) a costimulatory domain (domain); and
(d) an intracellular signaling domain (ICD).

In the present disclosure, the term "chimeric antigen receptor (CAR)" refers to an artificially constructed hybrid protein (fusion protein) or polypeptide containing a target-binding domain (e.g. single-chain variable fragment (scFv)) linked to an effector cell-signaling or effector cell-activating domain (e.g. T-cell signaling or T-cell activating domain). In general, the chimeric antigen receptor has the ability of redirecting T-cell specificity and reactivity toward a selected target in a non-MHC restricted manner by taking advantage of the antigen-binding property of a monoclonal antibody. The non-MHC-restricted antigen recognition confers the ability to recognize an antigen on T-cells expressing CAR, thus bypassing the major mechanism of tumor escape. Moreover, when expressed in T-cells, the CAR advantageously does not dimerize with the endogenous T-cell receptor (TCR) alpha and beta chains.

In an exemplary embodiment of the present disclosure, the chimeric antigen receptor of the present disclosure recognizes the HER2 antigen and is expressed on the cell surface since it includes the HER2-binding domain including the anti-HER2 antibody of the present disclosure or an antigen-binding fragment thereof.

The chimeric antigen receptor of the present disclosure includes a transmembrane domain because it is expressed on the cell surface. The transmembrane domain may be a transmembrane domain of a protein selected from a group consisting of the T-cell receptor alpha, beta or zeta chain, CD28, CD3 epsilon, CD45, CD4, CD5, CD8, CD9, CD16, CD22, CD33, CD37, CD64, CD80, CD86, CD134, CD137 and CD154, although not being limited thereto.

In a specific exemplary embodiment of the present disclosure, the transmembrane domain may be a transmembrane domain of CD8 or CD28.

The costimulatory domain of the chimeric antigen receptor of the present disclosure may be a functional signaling domain obtained from a protein selected from a group consisting of MHC class I molecule, TNF receptor protein, immunoglobulin-like protein, cytokine receptor, integrin, signaling lymphocytic activation molecule (SLAM), activating NK cell receptor, BTLA (B- and T-lymphocyte attenuator), Toll-like ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand binding specifically to CD83, although not being limited thereto.

In a specific exemplary embodiment of the present disclosure, the costimulatory domain may be a functional signaling domain obtained from a protein selected from a group consisting of CD28, OX40, 4-1BB (CD137) and/or ICOS (CD278), more specifically a functional signaling domain of CD28 and/or OX40.

In another exemplary embodiment of the present disclosure, the intracellular signaling domain is a functional signaling domain of 4-1BB, CD28, OX40 or CD3 zeta, or a combination thereof. Most specifically, the intracellular signaling domain is a functional signaling domain of CD3 zeta.

In another embodiment of the present disclosure, the intracellular signaling domain may be a functional signaling domain of OX40 ligand (OX40L). In another embodiment, the intracellular signaling domain is OX40 ligand.

The HER2-binding domain of the chimeric antigen receptor of the present disclosure is linked to the transmembrane domain by a hinge domain.

In another exemplary embodiment of the present disclosure, the hinge domain may be IgG4 hinge, CD8 hinge or IgD hinge.

Another aspect of the present disclosure provides a nucleic acid molecule encoding the anti-HER2 antibody or an antigen-binding fragment thereof, or the chimeric antigen receptor polypeptide described above.

In the present disclosure, the term "nucleic acid molecule" encompasses DNA (gDNA and cDNA) and RNA molecules, and the nucleotides that are the basic building blocks of the nucleic acid molecule include not only natural nucleotides but also analogues having modified sugar or base moieties (Scheit, *Nucleotide Analogs*, John Wiley, New York (1980); Uhlman and Peyman, *Chemical Reviews*, 90: 543-584 (1990)).

A nucleotide sequence encoding the antibody of the present disclosure or an antigen-binding fragment thereof, or the chimeric antigen receptor polypeptide is not limited to a specific nucleotide sequence as long as it is a nucleotide sequence encoding the amino acid sequences constituting the chimeric antigen receptor molecule.

This is because the variation in nucleotide sequences may not lead to change in protein sequences through expression. This is called codon degeneracy. Accordingly, the nucleotide sequence includes a nucleotide sequence including functionally equivalent codons, or codons encoding the same amino acid (for example, six codons encode arginine or serine due to codon degeneracy) or codons encoding a biologically equivalent amino acid.

In a specific exemplary embodiment of the present disclosure, the nucleotide sequence encoding the polypeptide constituting the heavy chain CDR, light chain CDR, heavy chain variable region, light chain variable region, heavy chain or light chain of the anti-HER2 antibody of the present disclosure or an antigen-binding fragment thereof is described in the attached sequence listings.

The nucleic acid molecule of the present disclosure, which encodes the anti-HER2 antibody or an antigen-binding fragment thereof, or the chimeric antigen receptor polypeptide, is understood to encompass a nucleotide sequence exhibiting substantial identity for the nucleotide sequence. The substantial identity means that, when the nucleotide sequence of the present disclosure is aligned to another sequence correspond to each other as much as possible and the aligned sequences are analyzed using an algorithm commonly used in the art, the nucleotide sequences exhibit at least 80% homology, more specifically at least 90% homology, most specifically at least 95% homology.

When considering the variation of biologically equivalent activity, it is understood that the nucleic acid molecule encoding the antibody of the present disclosure or an antigen-binding fragment; or the chimeric antigen receptor polypeptide encompasses a sequence exhibiting substantial identity to the sequences described in the sequence listings. The substantial identity means that, when the sequence of the present disclosure and another sequence are aligned to correspond to each other as much as possible and the aligned sequences are analyzed using an algorithm commonly used in the art, the sequences have at least 61% homology, more specifically 70% homology, further more specifically 80% homology, most specifically 90% homology. Methods of the alignment for sequence comparison are known in the art. Various methods and algorithms for the alignment are disclosed in Smith and Waterman, *Adv. Appl. Math.* 2: 482 (1981); Needleman and Wunsch, *J. Mol. Bio.* 48: 443 (1970); Pearson and Lipman, *Methods in Mol. Biol.* 24: 307-31 (1988); Higgins and Sharp, *Gene* 73: 237-44 (1988); Higgins and Sharp, *CABIOS* 5: 151-3 (1989); Corpet et al., *Nuc. Acids Res.* 16: 10881-90 (1988); Huang et al., *Comp. Appl. BioSci.* 8: 155-65 (1992) and Pearson et al., *Meth. Mol. Biol.* 24: 307-31 (1994). The NCBI's basic local alignment search tool (BLAST) (Altschul et al., *J. Mol. Biol.* 215: 403-10 (1990)) is accessible from the NBCI (National Center for Biotechnology Information) and on the Internet and may be used in connection with sequence analysis programs such as blastp, blastn, blastx, tblastn and tblastx. BLAST may be accessed through the BLAST webpage of the NCBI's website. The method for comparing sequence homology using such a program is available from the BLAST help page of the NCBI's website.

In connection with the claims of the application/patent, sequence identity is determined according to the Needleman and Wunsch algorithm.

Another aspect of the present disclosure provides a recombinant vector including the nucleic acid molecule.

In the present disclosure, the term "vector" includes a delivery vector and an expression vector.

In the present disclosure, the term "delivery vector" refers to a composition of a material which contains an isolated nucleic acid and can be used to deliver the isolated nucleic acid into a cell. It includes a linear polynucleotide, a polynucleotide associated with an ionic or amphiphilic compound, a plasmid and a virus, although not being limited thereto. More specifically, the delivery vector includes a self-replicating plasmid or virus. The term is also construed to include non-plasmid and non-viral compounds which facilitate transfer of nucleic acids into cells, such as, for example, polylysine compounds, liposomes, etc. Examples of the viral delivery vector include an adenoviral vector, an adeno-associated viral vector, a retroviral vector and a lentiviral vector, although not being limited thereto.

In the present disclosure, the term "expression vector" refers to a vector including a recombinant nucleotide including an expression control sequence operably linked to a nucleotide sequence to be expressed for expression of a target gene in a host cell. The expression vector includes a cis-acting element sufficient for expression and other elements for expression can be provided by a host cell or an in-vitro expression system. The expression vector includes a plasmid vector including a recombinant polynucleotide; a cosmid vector; and a viral vector such as a bacteriophage vector, an adenoviral vector, a lentiviral vector, a retroviral vector and an adeno-associated viral vector. In a specific exemplary embodiment of the present disclosure, a nucleic acid molecule encoding a switch molecule is operatively linked to a promoter of the vector of the present disclosure. In the present disclosure, the term "operatively linked" refers to functional linkage between a nucleic acid expression control sequence (e.g., a promoter, a signal sequence, or an array of a transcription factor binding site) and another nucleic acid sequence, wherein the control sequence affects the transcription and/or translation of the another nucleic acid sequence.

The recombinant vector system of the present disclosure may be constructed according to various methods known in the art. Specific methods are described in Sambrook et al., Molecular Cloning, A Laboratory Manual, Cold Spring Harbor Laboratory Press (2001), which is incorporated into the present disclosure by reference.

The vector of the present disclosure may be constructed as a vector for gene cloning, a vector for protein expression, or a vector for gene delivery. In addition, the vector of the present disclosure may be constructed by using a prokaryotic cell or a eukaryotic cell as a host cell.

For example, when the vector of the present disclosure is an expression vector and a eukaryotic cell is used as a host cell, a promoter derived from the genome of a mammalian cell (e.g., metallothionein promoter, β-actin promoter, human hemoglobin promoter and human muscle creatine promoter) or a promoter derived from a mammalian virus (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, Moloney virus promoter, Epstein-Barr virus (EBV) promoter and Rous sarcoma virus (RSV) promoter) may be used, and they generally have a polyadenylation sequence as a transcription termination sequence.

In an exemplary embodiment of the present disclosure, when the vector is a delivery vector, it may be a "retroviral vector". Retrovirus provides a convenient platform for a gene delivery system. A gene selected for gene delivery may be inserted in the retroviral vector and may be packaged within a retroviral particle. Then, the recombinant retrovirus may be delivered to a target host cell in vivo or in vitro. Many retroviral vectors are known in the art. In a specific exemplary embodiment of the present disclosure, the retroviral vector may be a pMT retroviral vector which is an MLV-based retroviral vector, although not being limited thereto.

In another exemplary embodiment of the present disclosure, the vector is a lentiviral vector or an adenoviral vector.

The vector of the present disclosure may be fused with other sequences for easy purification of the polypeptide or protein expressed thereby. For example, the fused sequence may be glutathione S-transferase (Pharmacia, USA), maltose-binding protein (NEB, USA), FLAG (IBI, USA), 6× His (hexahistidine; Quiagen, USA), etc. Meanwhile, the expression vector of the present disclosure may include a selectable marker gene and/or a reporter gene for evaluating the expression of the antibody of the present disclosure or an antigen-binding fragment thereof, or a CAR polypeptide including the same. The selectable marker gene includes an antibiotic-resistant gene commonly used in the art, e.g., genes resistant to ampicillin, gentamicin, carbenicillin, chloramphenicol, streptomycin, kanamycin, geneticin, neomycin and tetracycline. The reporter gene includes luciferase, beta-galactosidase, chloramphenicol, acetyltransferase or green fluorescent protein gene.

Methods for introducing the recombinant vector of the present disclosure into a cell and expressing the same are well known in the related art. The vector may be easily introduced into a host cell, e.g., a mammalian cell, a bacterial cell, a yeast cell or an insect cell according to methods known in the art. For example, the vector may be delivered into a host cell by physical, chemical or biological means. The physical means includes calcium phosphate coprecipitation, lipofection, particle bombardment, microinjection, electroporation, etc. The chemical means includes a colloidal dispersion system, e.g., a macromolecular complex, a nanocapsule, a microsphere, a bead, and a lipid-based system including an oil-in-water emulsion, a micelle, a mixed micelle and a liposome. And, the biological means includes use of a DNA or RNA vector such as a lentiviral vector, a retroviral vector, etc. as described above.

Another aspect of the present disclosure provides a host cell transformed with the recombinant vector.

The host cell capable of cloning and expressing the vector of the present disclosure stably and continuously may be any host cell known in the art. For example, a eukaryotic host cell suitable for the vector includes a monkey kidney cell 7 (COS7), an NSO cell, an SP2/0 cell, a Chinese hamster ovary (CHO) cell, a W138 cell, a baby hamster kidney (BHK) cell, a MDCK cell, a myeloma cell, a HuT 78 cell and an HEK-293 cell, although not being limited thereto.

Another aspect of the present disclosure provides an effector cell expressing the chimeric antigen receptor (CAR) polypeptide.

In an exemplary embodiment of the present disclosure, the effector cell is selected from a group consisting of a dendritic cell, a killer dendritic cell, a mast cell, a natural killer cell, a B lymphocyte, a T lymphocyte, a macrophage and precursor cells thereof, although not being limited thereto. The T lymphocyte cell is selected from a group consisting of an inflammatory T lymphocyte, a cytotoxic T lymphocyte, a regulatory T lymphocyte or a helper T lymphocyte.

In the present disclosure, the effector cell includes a group of autologous cells or allogenic cells. That is to say, the effector cell includes a group of autologous cells or allogenic cells expressing the HER2-specific CAR polypeptide.

In another exemplary embodiment of the present disclosure, the effector cell includes a group of cells transfected or transduced with a vector including a nucleic acid molecule encoding the HER2-specific CAR polypeptide. The transfection or transduction may be achieved by various means known in the art without limitation.

Accordingly, in a specific exemplary embodiment of the present disclosure the present disclosure, the HER2-specific CAR-encoding nucleic acid molecule is delivered into an effector cell, e.g., a T lymphocyte or a natural killer cell, and transcribed into mRNA. The HER2-specific CAR polypeptide is translated from the mRNA and expressed on the surface of the effector cell.

Another aspect of the present disclosure provides a pharmaceutical composition for preventing or treating cancer, which contains: (a) a pharmaceutically effective amount of the anti-HER2 antibody of the present disclosure or the antigen-binding fragment thereof described above; and (b) a pharmaceutically acceptable carrier.

Another aspect of the present disclosure provides a pharmaceutical composition for treating cancer or an inflammatory disease, which contains an effector cell expressing the chimeric antigen receptor polypeptide described above.

The pharmaceutical composition is a pharmaceutical composition for immunotherapy, which contains an effector cell expressing the anti-HER2 antibody or an antigen-binding fragment thereof; or the chimeric antigen receptor polypeptide.

In the present disclosure, "immunotherapy" refers to treatment of cancer by activating the immune system. Immunotherapy is classified into active immunotherapy and passive immunotherapy. Active immunotherapy includes i) cancer vaccine therapy of activating the immune system by injecting cancer cells or substances produced by cancer cells into human body, and ii) immunomodulatory therapy of activating specific leukocytes by administering immunomodulatory agents such as cytokines (interferons, interleukins, etc.), growth factors, etc. Passive immunotherapy includes antibody therapy and immune cell therapy. Specifically, immune cell therapy includes dendritic cell vaccine therapy, chimeric antigen receptor T (CAR-T) cell therapy, natural killer (NK) cell therapy, cytotoxic T lymphocyte (CTL) therapy, adoptive cell transfer, etc., although not being limited thereto. In the present disclosure, the immunotherapy mainly refers to antibody therapy using the anti-HER2 antibody and immune cell therapy using the HER2-specific CAR.

The pharmaceutical composition of the present disclosure contains an effector cell expressing the anti-HER2 antibody of the present disclosure or an antigen-binding fragment thereof; the chimeric antigen receptor polypeptide; or the chimeric antigen receptor as an active ingredient. Therefore, description of the details described above will be omitted to avoid redundancy.

As demonstrated in the following examples, the anti-HER2 antibody of the present disclosure exhibits better killing ability for MCF-7 cells on which the trastuzumab antibody hardly acts. In addition, the anti-HER2 antibody of the present disclosure exhibits improved killing ability for SKBR3 breast cancer cells when co-administered with trastuzumab. Accordingly, the composition of the present disclosure is very effective for combined administration with the trastuzumab antibody for treatment of cancer and for treatment of cancer not treated with trastuzumab.

The cancer that can be prevented or treated by the composition of the present disclosure includes various cancers known in the art. For example, it includes breast cancer, ovarian cancer, gastric cancer, lung cancer, liver cancer, bile duct cancer, bronchial cancer, nasopharyngeal cancer, laryngeal cancer, pancreatic cancer, bladder cancer, kidney cancer, colorectal cancer, colon cancer, cervical cancer, brain cancer, prostate cancer, bone cancer, head and neck cancer, skin cancer, thyroid cancer, parathyroid cancer or ureteral cancer.

Specifically, the cancer that can be prevented or treated by the composition of the present disclosure is HER2-expressing cancer, more specifically HER2-expressing breast cancer or gastric cancer.

The pharmaceutically acceptable carrier contained in the pharmaceutical composition of the present disclosure is one commonly used in preparation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain a lubricant, a wetting agent, a sweetener, a flavor, an emulsifier, a suspending agent, a preservative, etc. in addition to the above-described ingredients. Suitable pharmaceutically acceptable carriers and preparations are described in detail in Remington's Pharmaceutical Sciences (19th ed., 1995).

The pharmaceutical composition of the present disclosure may be administered orally or parenterally. For example, it may be administered intravenously, subcutaneously, intramuscularly, intraperitoneally, topically, intranasally, intrapulmonarily, intrathecally, ocularly, intradermally, transdermally, etc.

An administration dosage of the pharmaceutical composition of the present disclosure varies depending on such factors as formulation method, administration method, the age, body weight, sex of a patient, pathological condition, food, administration time, administration route, excretion rate and responsiveness. A normally trained physician can easily determine and prescribe an administration dosage for effective treatment or prevention. In a specific exemplary embodiment of the present disclosure, a daily administration dosage of the pharmaceutical composition of the present disclosure is 0.0001-100 mg/kg. In the present disclosure, the term "pharmaceutically effective amount" refers to an amount sufficient for preventing or treating cancer.

The pharmaceutical composition of the present disclosure may be formulated into a unit-dosage form or a multiple-dosage form using a pharmaceutically acceptable carrier and/or excipient according to a method that can be easily employed by those of ordinary skill in the art to which the present disclosure belongs. The formulation may be in the form of a solution in an oily or aqueous medium, a suspension, an emulsion, an extract, a pulvis, a suppository, a powder, a granule, a tablet or a capsule, and may further contain a dispersant or a stabilizer.

In an exemplary embodiment of the present disclosure, the pharmaceutical composition of the present disclosure may further contain the trastuzumab antibody.

The pharmaceutical composition of the present disclosure may further contain, in addition to the active ingredient derived above, another pharmaceutically active medication or drug, e.g., a chemotherapy agent such as asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc., a targeted therapy agent such bevacizumab, olaparib, etc., or an immune checkpoint inhibitor such as nivolumab or pembrolizumab, or may be co-administered with them.

Another aspect of the present disclosure provides a method for treating cancer, which includes a step of administering a composition containing an effector cell expressing the anti-HER2 antibody or an antigen-binding fragment thereof; or the HER2-specific chimeric antigen receptor to a subject in need of treatment.

The cancer to be treated by the therapeutic method of the present disclosure is the same as defined above with regard to the pharmaceutical composition.

In an exemplary embodiment of the present disclosure, the subject may be a mammal or human.

Since the method for treating cancer or an inflammatory disease of the present disclosure uses an effector cell expressing the antibody or an antigen-binding fragment; or the chimeric antigen receptor described above as an active ingredient, description of the details described above will be omitted to avoid redundancy.

The anti-HER2 antibody or an antigen-binding fragment thereof described above may be used for diagnosis, e.g., diagnosis of cancer.

Accordingly, another aspect of the present disclosure provides a kit for diagnosing cancer, which includes the anti-HER2 antibody of the present disclosure or an antigen-binding fragment thereof.

Since the diagnostic kit of the present disclosure includes the anti-HER2 antibody of the present disclosure or an antigen-binding fragment thereof described above and diagnoses the same disease as described above with regard to the pharmaceutical composition of the present disclosure, description of the details described above will be omitted to avoid redundancy.

Since the kit includes an antibody, it can be prepared to be suitable for various immunoassay or immunostaining applications. The immunoassay or immunostaining includes radioimmunoassay, radioimmunoprecipitation, immunoprecipitation, enzyme-linked immunosorbent assay (ELISA), capture ELISA, inhibition or competition assay, sandwich assay, flow cytometry, immunofluorescence staining and immunoaffinity purification, although not being limited thereto. Methods for the immunoassay or immunostaining are described in Enzyme Immunoassay, E. T. Maggio, ed., CRC Press, Boca Raton, Florida, 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies: A Laboratory Manual, Cold Spring Harbor Laboratory Press, 1999, which are incorporated in the present disclosure by reference.

For example, when the method of the present disclosure is carried out by radioimmunoassay, an antibody labeled with a radioisotope (e.g., $C^{14}$, $I^{125}$, $P^{32}$ or $S^{35}$) may be used to detect the HER2 protein. When the method of the present disclosure is carried out by ELISA, a specific exemplary embodiment of the present disclosure includes: (i) a step of coating a sample to be analyzed on the surface of a solid substrate; (ii) a step of reacting the sample with the anti-HER2 antibody of the present disclosure as a primary antibody; (iii) a step of reacting the resultant of the step (ii) with a secondary antibody coupled with an enzyme; and (iv) a step of measuring the activity of the enzyme.

Appropriate examples of the solid substrate are a hydrocarbon polymer (e.g., polystyrene or polypropylene), glass, a metal or a gel, most specifically, a microtiter plate.

The enzyme coupled with the secondary antibody may include an enzyme that catalyzes chromogenic reaction, fluorescence reaction, luminescent reaction or infrared reaction, although not being limited thereto. For example, it includes alkaline phosphatase, 0-galactosidase, horseradish peroxidase, luciferase and cytochrome P450. When alkaline phosphatase is used as the enzyme coupled with the secondary antibody, a chromogenic substrate such as bromochloroindolyl phosphate (BCIP), nitro blue tetrazolium (NBT), naphthol-AS-B1-phosphate and enhanced chemifluorescence (ECF) may be used as the substrate. When horseradish peroxidase is used, a substrate such as chloronaphthol, aminoethylcarbazole, diaminobenzidine, D-luciferin, lucigenin (bis-N-methylacridinium nitrate), resorufin benzyl ether, luminol, Amplex Red (10-acetyl-3,7-dihydroxyphenoxazine), HYR (p-phenylenediamine-HCl and pyrocatechol), tetramethylbenzidine (TMB), 2,2-azino-di[3-ethylbenzthiazoline sulfonate] (ABTS), o-phenylenediamine (OPD), naphthol/pyronin, glucose oxidase, t-NBT (nitro blue tetrazolium) and m-PMS (phenzaine methosulfate) may be used.

When the method of the present disclosure is carried out by capture ELISA, the method includes: (i) a step of coating the HER2 antibody as a capture antibody on the surface of a solid substrate; (ii) a step of reacting the capture antibody with a sample; (iii) a step of reacting the resultant of the step (ii) with an HER2 detection antibody conjugated with a label; and (iv) a step of measuring a signal generated from the label.

The anti-HER2 antibody of the present disclosure has a label that generates a signal that can be detected by the detection antibody. The label includes a chemical substance (e.g., biotin), an enzyme (alkaline phosphatase, 0-galactosidase, horseradish peroxidase or cytochrome P450), a radioactive substance (e.g., $C^{14}$, $I^{125}$, $P^{32}$ and $S^{35}$), a fluorescent material (e.g., fluorescein), a light-emitting material, a chemiluminescent material and a FRET (fluorescence resonance energy transfer) material, although not being limited thereto. Various labels and labeling method are described in Ed Harlow and David Lane, Using Antibodies: A Laboratory Manual, Cold Spring Harbor Laboratory Press, 1999.

In the ELISA method and the capture ELISA, the measurement of the enzyme activity or the measurement of the signal may be carried out according to various methods known in the art. The signal may be detected easily by using streptavidin when biotin is used as the label, and using luciferin when luciferase is used.

The sample to which the kit of the present disclosure can be applied includes a cell, a tissue, a tissue-derived extract, a lysate, a purification product, a blood, a plasma, a serum, a lymph or ascites, although not being limited thereto.

The antibody of the present disclosure may be used in in-vivo or in-vitro imaging. Another aspect of the present disclosure provides a composition for imaging, which contains a conjugate in which the antibody of the present disclosure is conjugated to a label generating a detectable signal.

The label generating a detectable signal includes a T1 contrast agent (e.g., a Gd chelate compound), a T2 contrast agent (e.g., a superparamagnetic material (e.g., magnetite, $Fe_3O_4$, $\gamma$-$Fe_2O_3$, manganese ferrite, cobalt ferrite and nickel ferrite)), a radioiosotope (e.g., $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$ and $^{206}Bi$), a fluorescent material (fluorescein, phycoerythrin, rhodamine, lissamine, Cy3 and Cy5), a chemiluminescent material, a magnetic particle, a mass label or an electron-dense particle, although not being limited thereto.

Advantageous Effects

The features and advantages of the present disclosure may be summarized as follows:
(a) The antibody of the present disclosure or an antigen-binding fragment is an antibody that specifically binds to HER2 which is highly expressed in cancer cells (particularly, breast cancer or gastric cancer cells), and binds to an epitope that is different from an epitope to which trastuzumab binds. The present disclosure provides the antibody or the antigen-binding fragment, a chimeric antigen receptor including the same, and uses thereof.
(b) The antibody of the present disclosure or an antigen-binding fragment is unique in that its CDR sequence has very low homology to the CDR sequences of existing HER2-targeting antibodies.
(c) When compared with trastuzumab, the antibody of the present disclosure exhibits better killing ability for HER2-unexpressed cancer cells which have non-reactivity (or resistance) to the trastuzumab antibody or have reduced sensitivity. In addition, when the anti-HER2 antibody of the present disclosure is administered in combination with trastuzumab, a synergistic killing ability is achieved for cancer cells on which the trastuzumab antibody acts. Therefore, a composition of the present disclosure can be used for combined administration with the trastuzumab antibody for the treatment of cancer, or for the treatment of cancer not treated with trastuzumab. In particular, when expressed in effector cells such as T lymphocytes, etc., the chimeric antigen receptor including the anti-HER2 antibody of the present disclosure or an antigen-binding fragment may be used for immune cell therapy of various HER2-related cancers.
(d) Without wishing to be bound by theory, it is considered that the antibody of the present disclosure exhibits the above-described effects since it binds to an epitope that is different from an epitope to which trastuzumab binds and inhibits HER2 in a different manner from that of trastuzumab.

BEST MODE FOR CARRYING OUT INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1: Development of Anti-HER2 Antibody

For development of antibodies, the extracellular domain (ECD) of the HER2 protein was produced using animal cells. The DNA in which a hinge and an Fc region ($CH_2$—$CH_3$) of human IgG1 were bound to the C-terminus of ECD was cloned into pCEP4 (Invitrogen, Cat. No. V044-50) using HindIII and BamHI restriction enzymes. Then, the cloned vector was transiently transformed into FreeStyle 293F (Invitrogen, Cat. No. R790-07) cells using polyethyleneimine (Polyscience Inc., Cat. No. 23966) and then purified from the cell culture using a Protein-A Ceramic HyperD F resin (PALL, Cat No. 20078-028). The purified protein was quantitated using a protein assay dye (Bio-Rad, Cat. No. 500-0006) and its concentration and purity were investigated via Coomassie Blue staining following SDS-PAGE. 100 μg of the protein antigen was mixed with a Freund's adjuvant (Sigma, Cat. No. F5506) and then injected intraperitoneally into BALB/c mouse (Dae Han Bio). 2 weeks later, 100 μg of the antigen diluted in PBS was injected further. 3 days later, the spleen of the mouse was taken out and lymphocytes were isolated. The isolated lymphocytes were mixed with SP2/0-Ag14 myeloma cells (ATCC, Cat. No. CRL-1581) at a ratio of 5:1 and then fused using PEG-1500 (Roche, Cat. No. 783641). The fused cells (hybridoma) were selectively sorted out and cultured in a medium containing a HAT supplement (Sigma, Cat. No. H0262).

The obtained hybridoma cells were examined via ELISA to determine whether they were the cells producing an antibody that bind to the antigen. HER2-ECD-Fc or ChromPure human IgG (hIgG, Jackson Immunoresearch Lab. Inc., Cat. No. 009-000-003) was immobilized at room temperature onto a Costar 96-well plate (Corning, Cat. No. 3590) at a concentration of 1 μg/mL for 1 hour. The resultant was washed 3 times with TBS-T (0.05% Triton X-100) and then blocked at room temperature for 30 minutes with 300 μL of TBS-T/SM (2% skim milk). After washing the blocked plate 3 times and adding the hybridoma culture, the antibody was allowed to bind at 37° C. for 1 hour. After washing 3 times and then adding anti-mIgG-HRP (Pierce, Cat. No. 31439) diluted to 1:5,000 in TBS-T/SM, as a secondary antibody, the antibody was allowed to bind at 37° C. for 1 hour. After washing the resultant 3 times and adding TMB (SurModics, Cat. No. TMBC-1000-01), the mixture was allowed to develop color at room temperature for 5 minutes. Then, the color development was stopped by adding 1 N sulfuric acid (DukSan, Cat. No. 254). Absorbance was measured at 450 nm using Victor X3 (PerkinElmer, Cat. No. 2030-0030) and the antibody binding specifically to HER2-ECD-Fc was selected.

Since HER2 is a protein expressed on cell surface, it was investigated whether the developed antibody was bound to HER2-overexpressing cells via cell-based ELISA. HER2-overexpressing SKOV-3 ovary cancer cells (Korean Cell Line Bank, Cat. No. 30077) were aliquoted onto a Costar 96-well cell culture plate (Corning, Cat. No. 3595) at 10,000 cell/well and then cultured for 24 hours. On the following day, after removing the cell culture supernatant, the resultant was washed 3 times with PBS and cultured further at 37° C. for 2 hours after adding the hybridoma cell culture. After washing 3 times with TBS-T and adding goat anti-mIgG-HRP diluted in PBS/FBS (3% FBS) to 1:5,000, as a secondary antibody, the resultant was treated at room temperature for 1 hour. After washing 3 times with TBS-T, it was allowed to develop color using TMB. 61 clones showing higher absorbance than that of the SP2/0 cell culture as a negative control group were selected.

The five antibodies (hz2G10, hz39D2, 24D3, 1G3, hz8G11) finally selected from the monoclonal antibodies binding specifically to HER2 were modified to chimeric antibodies or humanized antibodies (hz). The amino acid sequences of the chimeric antibodies or humanized antibodies are described in the attached sequence listings.

The absorbance of the finally selected five antibodies (hz2G10, hz39D2, 24D3, 1G3, hz8G11) is shown in FIG. 1 and Table 1.

Verification of Binding of HER2 Proteins of Five Selected Antibodies to Extracellular Domain (ECD)

TABLE 1

| | Concentration (μg/mL) | | | | | | | | |
|---|---|---|---|---|---|---|---|---|---|
| Antibodies | $5 \times 10^{-7}$ | $5 \times 10^{-6}$ | $5 \times 10^{-5}$ | $5 \times 10^{-4}$ | $5 \times 10^{-3}$ | $5 \times 10^{-2}$ | $5 \times 10^{-1}$ | 5 | 50 |
| PBS | 0.13 | 0.13 | 0.14 | 0.14 | 0.14 | 0.13 | 0.16 | 0.15 | 0.14 |
| hz2G10 | 0.12 | 0.12 | 0.12 | 0.12 | 0.22 | 1.16 | 2.69 | 2.79 | 2.81 |
| hz39D2 | 0.12 | 0.12 | 0.15 | 0.47 | 2.29 | 2.92 | 2.78 | 2.90 | 2.83 |
| 24D3 | 0.11 | 0.11 | 0.12 | 0.22 | 1.13 | 2.76 | 2.90 | 2.92 | 2.75 |
| 1G3 | 0.11 | 0.11 | 0.14 | 0.35 | 1.77 | 2.79 | 2.78 | 2.81 | 2.76 |
| hz8G11 | 0.12 | 0.12 | 0.14 | 0.34 | 1.67 | 2.72 | 2.94 | 2.90 | 2.74 |

Example 2: Verification of Binding Site of Developed Antibody for HER2 Protein

The binding site of the selected five antibodies (hz2G10, hz39D2, 24D3, 1G3, hz8G11) for the extracellular domain (ECD) of the HER2 protein was verified by ELISA. For ELISA, the extracellular domain (ECD) of the ERBB family protein was produced using animal cells and was used as an antigen. Specifically, the DNA in which a hinge and an Fc region ($CH_2$—$CH_3$) of human IgG1 were bound to the C-terminus of ECD was cloned into pCEP4 (Invitrogen, Cat. No. V044-50) using HindIII and BamHI restriction enzymes. Then, the cloned vector was transiently transformed into FreeStyle 293F (Invitrogen, Cat. No. R790-07) cells using polyethyleneimine (Polyscience Inc., Cat. No. 23966) and then HER2-ECD DI Fc, HER2-ECD DII Fc, HER2-ECD DIII Fc, HER2-ECD DIV Fc and HER2-ECD Fc fusion proteins were purified from the cell culture using a Protein-A Ceramic HyperD F resin (PALL, Cat No. 20078-028). The purified protein was quantitated using a protein assay dye (Bio-Rad, Cat. No. 500-0006) and its concentration and purity were investigated via Coomassie Blue staining following SDS-PAGE.

The HER2-ECD DI Fc, HER2-ECD DII Fc, HER2-ECD DIII Fc, HER2-ECD DIV Fc and HER2-ECD Fc fusion proteins were immobilized at 4° C. overnight onto a Costar 96-well plate (Corning, Cat. No. 3590) at a concentration of 1 μg/mL for 1 hour. The resultant was washed 3 times with TBS-T (0.05% Triton X-100) and then blocked at room temperature for 1 hour with 100 μL of TBS-T/BSA (5% BSA). After washing the blocked plate 3 times and adding the anti-HER2 antibody, the antibody was allowed to bind at room temperature for 1 hour. After washing 3 times and then adding anti-human IgG-HRP diluted to 1:3,000 in TBS-T/BSA, as a secondary antibody, the antibody was allowed to bind at room temperature for 1 hour. After washing the resultant 3 times and adding TMB (SurModics, Cat. No. TMBC-1000-01), the mixture was allowed to develop color at room temperature for 5 minutes. Then, the color development was stopped by adding 1 N sulfuric acid (DukSan, Cat. No. 254). Absorbance was measured at 450 nm using Victor X3 (PerkinElmer, Cat. No. 2030-0030).

Figure 2:
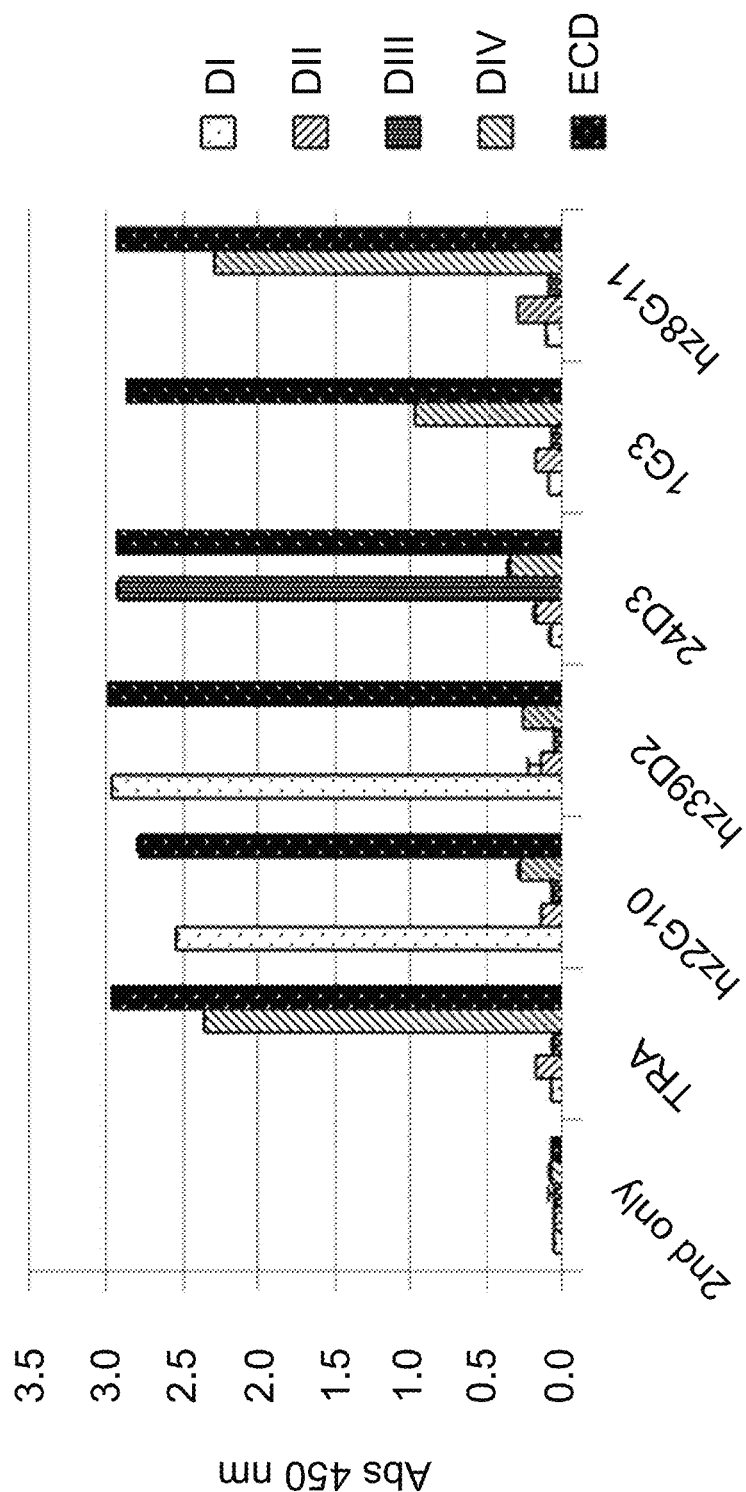
FIG. 2 is a bar graph showing the a results of investigating the extracellular domain of HER2 to which hz2G10, hz39D2, 24D3, 1G3 and hz8G11 clones bind.

The result is shown in FIG. 2.

As show in FIG. 2, among the antibodies developed in the present disclosure, hz2G10 and hz39D2 were bound to the domain 1 of the extracellular domains of the HER2 protein, 24D3 was bound to the domain 3, and 1G3 and hz8G11 were bound to the domain 4.

From this result, it can be seen that the five antibodies of the present disclosure can inhibit the growth of the HER2-overexpressed cancer cells by binding to the HER domain which is different from the extracellular domain 4 of the HER2 protein to which trastuzumab (TRA) binds (hz2G10, hz39D2, 24D3), or can exhibit remarkably superior effect of inhibiting cellular growth when used alone or co-administered with trastuzumab. Therefore, they can be usefully used for prevention or treatment of cancer related with the expression of the HER2 proteins either alone or together with trastuzumab.

Example 3: Comparison of Inhibitory Effect of Developed Antibody Against Growth of Breast Cancer Cells Cell viability was analyzed by treating HER2-overexpressed SKBR3 breast cancer cells or HER2-unexpressed breast cancer cells with MCF-7 either alone or together with trastuzumab. For co-administration, the developed antibody and trastuzumab were mixed at a weight ratio of 1:1. SKBR3 cells (Korean Cell Line Bank, Cat. No. 30030, 5,000 cells/well) and MCF-7 cells (ATCC, Cat. No. HTB22, 5,000 cells/well) were aliquoted onto a 96-well plate and cultured for 24 hours. The cells were cultured further for 4 days after treating with the purified antibody at a final concentration of 20 μg/mL. For measurement of cell viability, CCK-8 (Dojindo, Cat. No. CK-04-13) was added to a final concentration of 10% and absorbance was measured after treating at 37° C. for 3 hours. Relative cell viability was calculated with respect to the absorbance of the antibody-untreated well as 100%.

The result is shown in FIGS. 3a-3d and Table 2.

Relative Cell Viability of HER2-Positive SKBR3 Breast Cancer Cells and HER2-Negative MCF-7 Breast Cancer Cells Treated with Antibody (Single Treatment)

TABLE 2

| Clones | Relative cell viability at 20 µg/mL (%) | |
| --- | --- | --- |
|  | SKBR3 | MCF-7 |
| hIgG | 94.68 | 92.11 |
| TRA (trastuzumab) alone | 63.68 | 98.22 |
| hz2G10 | 89.06 | 97.43 |
| hz39D2 | 96.46 | 91.42 |
| 24D3 | 93.97 | 87.33 |
| 1G3 | 74.81 | 98.66 |
| hz8G11 | 74.02 | 98.95 |

Figure 3A:
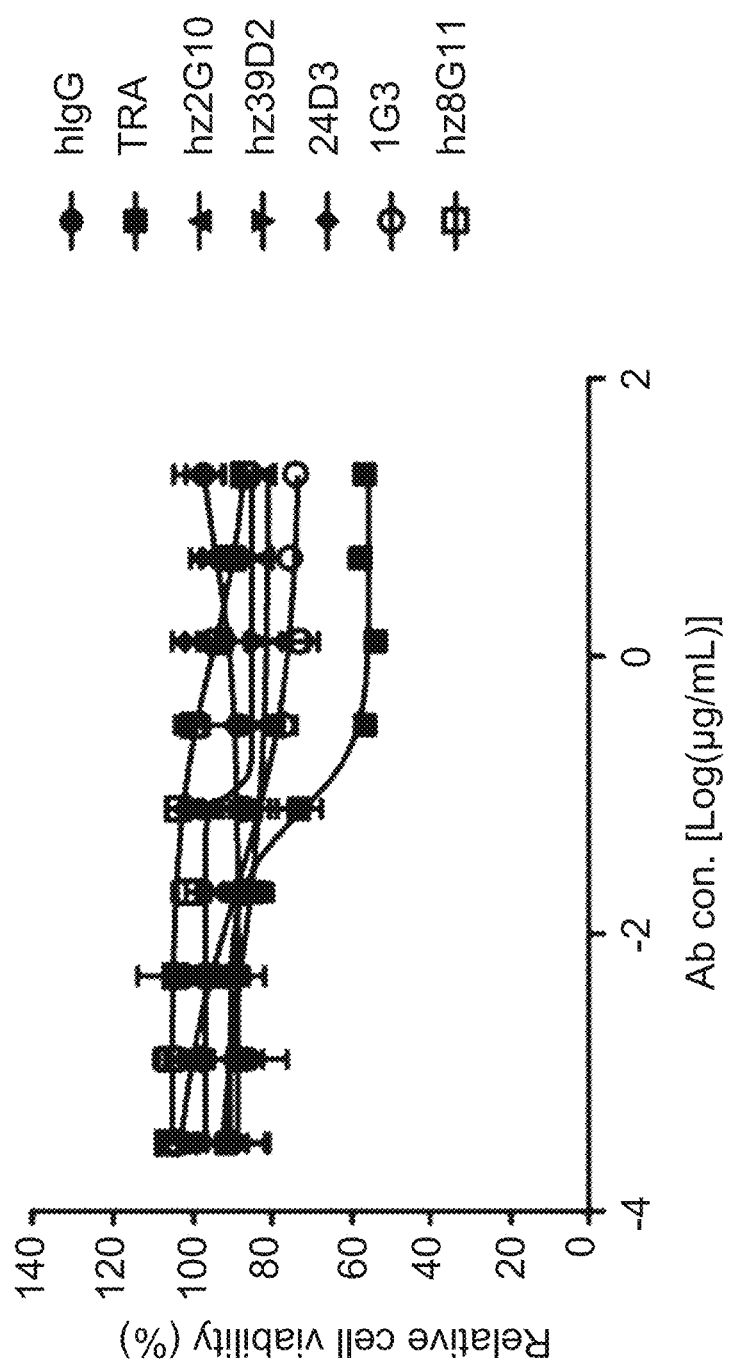
FIG. 3A and FIG. 3B are line graphs showing the results of analyzing the effect of single administration of five antibodies of the present disclosure (hz2G10, hz39D2, 24D3, 1G3 and hz8G11) on the inhibition of the growth of HER2-overexpressed breast cancer cells (SKBR3) and HER2-unexpressed breast cancer cells (MCF-7).
Figure 3B:
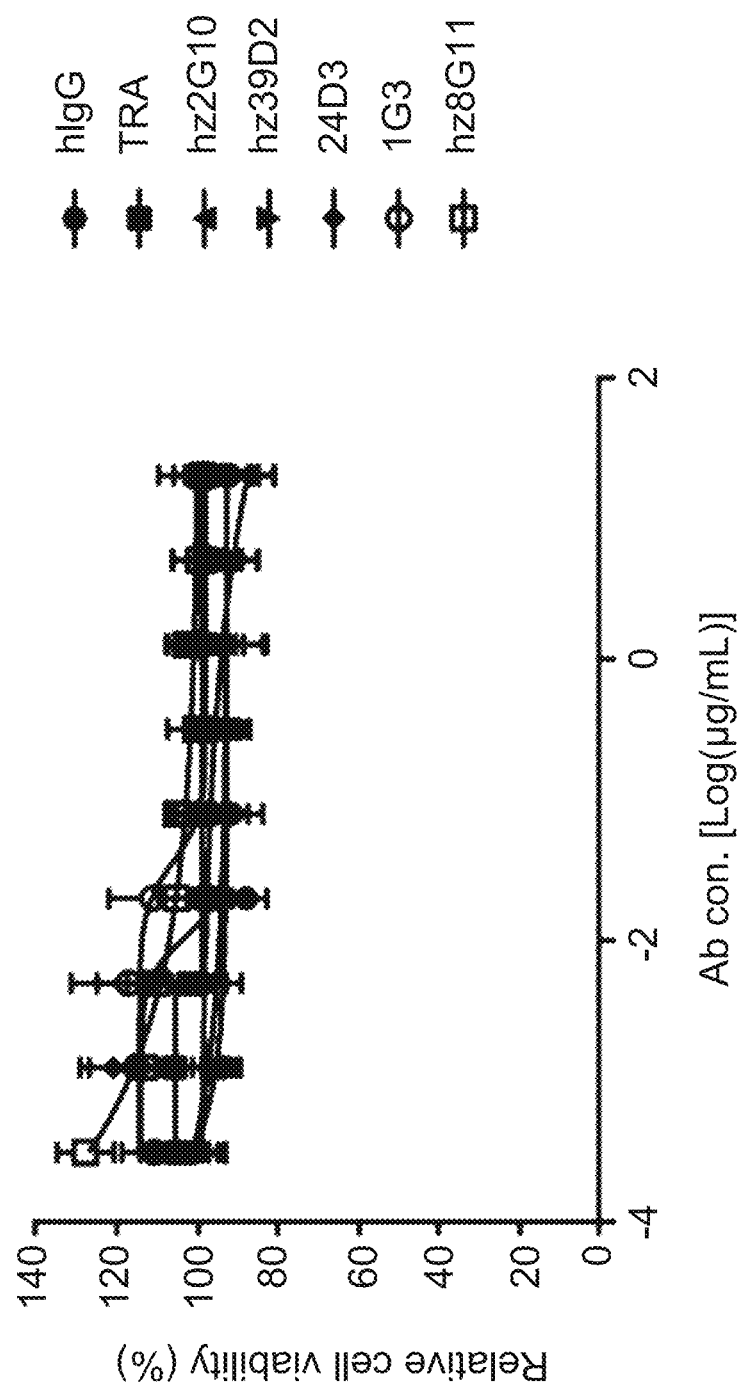

In the above table, hIgG stands for human IgG. As seen from FIG. 3A, FIG. 3B and Table 2, the five antibodies of present disclosure showed the effect of inhibiting the proliferation of SKBR3 breast cancer cells when treated alone. They showed comparable or better effect of inhibiting cellular growth as compared to the positive control trastuzumab at different concentrations (FIG. 3A). However, the five antibodies of present disclosure did not show significant effect of inhibiting cell proliferation of the HER2-negative MCF-7 cells like the positive control trastuzumab (FIG. 3B).

Relative Cell Viability of HER2-Positive SKBR3 Breast Cancer Cells and HER2-Negative MCF-7 Breast Cancer Cells Treated with Antibody (Co-Treatment)

TABLE 3

| Clones | Relative cell viability at 20 µg/mL (%) | |
| --- | --- | --- |
|  | SKBR3 | MCF-7 |
| hIgG | 94.68 | 92.11 |
| TRA (trastuzumab) alone | 63.68 | 98.22 |
| TRA + hz2G10 | 68.98 | 90.56 |
| TRA + hz39D2 | 77.29 | 90.62 |
| TRA + 24D3 | 63.75 | 97.21 |
| TRA + 1G3 | 62.16 | 102.33 |
| TRA + hz8G11 | 52.62 | 98.41 |

Figure 3C:
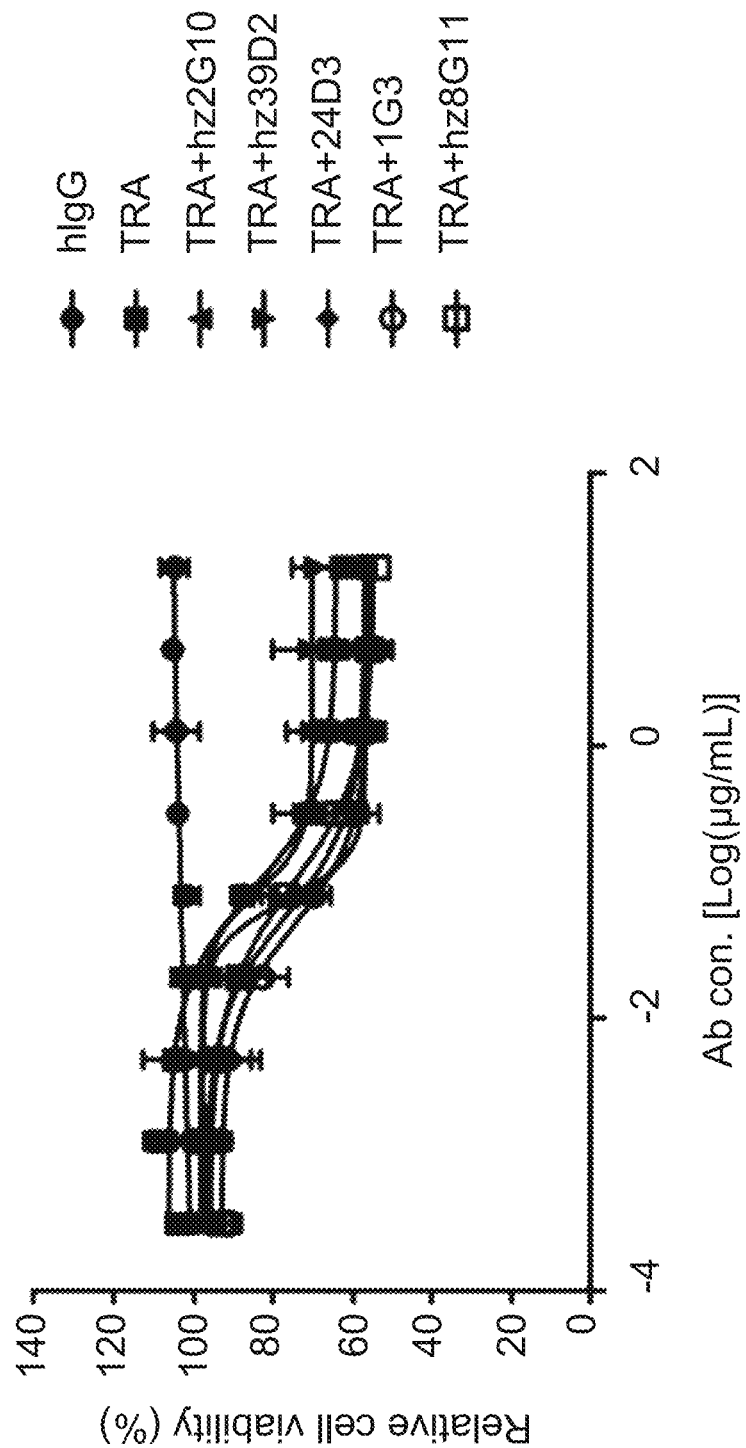
FIG. 3C and FIG. 3D are line graphs showing the results of analyzing the effect of co-administration of five antibodies of the present disclosure (hz2G10, hz39D2, 24D3, 1G3 and hz8G11) and the trastuzumab (TRA) antibody on the inhibition of the growth of HER2-overexpressed breast cancer cells (SKBR3) and HER2-unexpressed breast cancer cells (MCF-7).
Figure 3D:
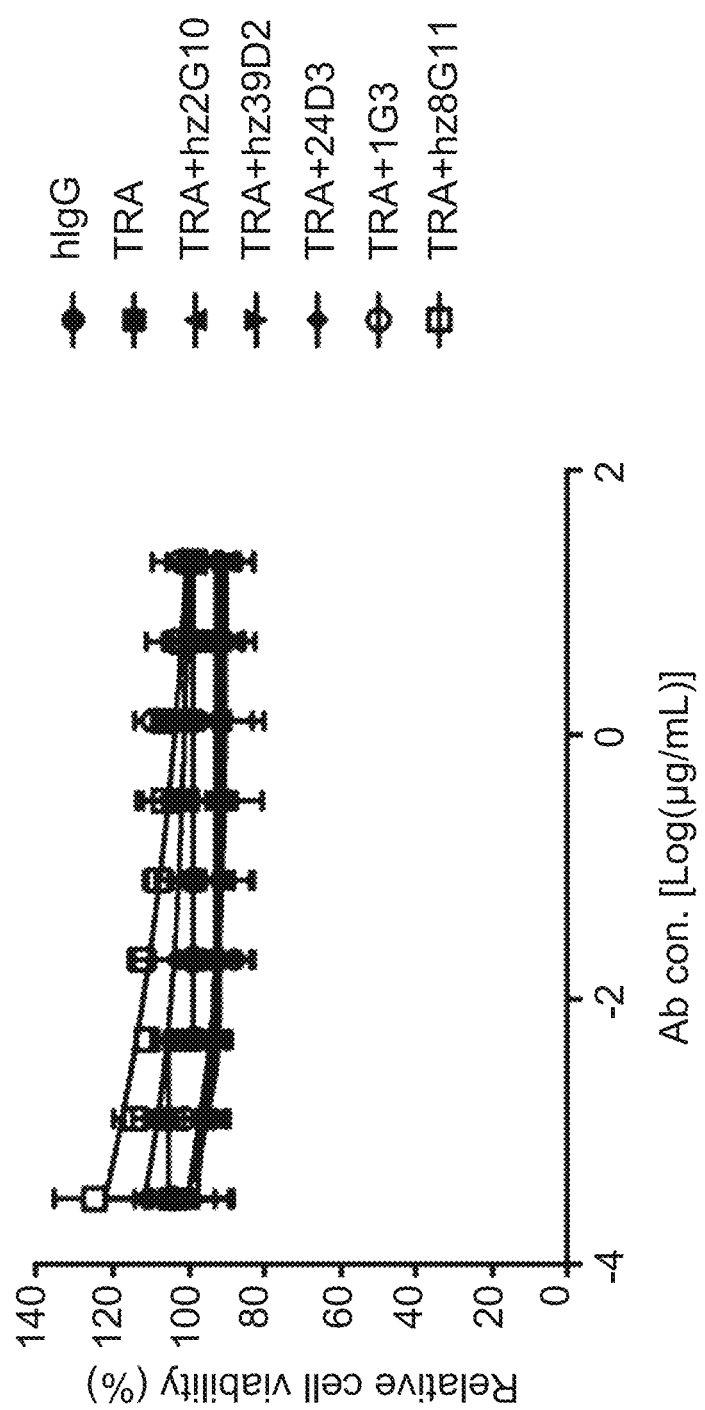

In the above table, hIgG denotes the test group treated with human IgG, and TRA + denotes the test groups co-administered with trastuzumab and the antibody of the present disclosure. As seen from FIG. 3C, FIG. 3D and Table 3, all of the five antibodies of present disclosure (hz2G10, hz39D2, 24D3, 1G3, hz8G11) showed comparable or better effect of inhibiting cellular growth when treated to the SKBR3 breast cancer cells together with trastuzumab as compared to single treatment with trastuzumab (FIG. 3C).

Without wishing to be bound by theory, it is considered that the antibody of the present disclosure exhibits the above-described effect since it binds to an epitope on HER2 that is different from an epitope to which trastuzumab binds and inhibits HER2 in a different manner from that of trastuzumab.

Example 4: Antibody Sequence Analysis

For analysis of the antibody sequence, a phage Fab antibody library was constructed using the respective hybridoma RNAs and a 3-step panning was conducted to obtain a phage that binds to HER2-ECD-Fc (Phage display: a laboratory manual, Carlos Barbas III, et al., Cold Spring Harbor Laboratory Press). After culturing the hybridoma, RNA was isolated using the SV total RNA isolation system (Promega, Cat. No. Z3100) and cDNA was synthesized therefrom. Using a known primer set (see Phage display: a laboratory manual, Carlos Barbas III, et al., Cold Spring Harbor Laboratory Press), the variable region of the antibody was amplified and cloned into the pComb3X vector (Barbas Laboratory, Scripps Research Institute) using a Sfi-I restriction enzyme after ligating to human Ck (kappa chain) and CH1, and then transformed into ER2537 bacteria (New England Biolabs, Cat. No. 801-N). The transformed bacteria were transfected with the VCSM13 helper phage (Stratagene, Cat. No. 200251) and a clone which binds to HER2-ECD-Fc was obtained using an immunotube to which HER2-ECD-Fc was immobilized.

From the colonies of the antibodies, the antibody that binds to HER2-ECD-Fc was confirmed via ELISA. The colonies of the transformed bacteria were cultured at 37° C. until the absorbance at 600 nm reached 0.5, treated with IPTG at a final concentration of 1 mM, and allowed to express antibodies in the form of Fab while culturing overnight at 30° C. After collecting cells by centrifuging 5 mL of the culture, the cells were suspended in 0.4 mL of 1×TES (50 mM Tris, 1 mM EDTA, 20% (v/v) sucrose, pH 8.0) and then treated at 4° C. for 10 minutes. After adding 0.6 mL of 0.2×TES thereto and treating further at 4° C. for 30 minutes, the resultant was centrifuged and a supernatant was taken. After washing a Costar 96-well half area plate (Corning Inc., Cat. No. 3690) coated with HER2-ECD-Fc at a concentration of 1 µg/mL 3 times with TBS-T, it was blocked with TBS-T/SM (3% non-fat skim milk, 0.05% Triton X-100) at room temperature for 1 hour. The culture broth or periplasmic extract (periplasm) of each colony was diluted at a ratio of 1:3 using TBS-T/SM and allowed to bind at room temperature for 1 hour. After washing 3 times and diluting to 1:5000 with anti-HA-HRP (Roche, Cat. No. 120-138-190-01) as a secondary antibody, the resultant was allowed to bind at room temperature for 1 hour. After washing 3 times, the resultant was allowed to develop color using TMB.

Most colonies showed absorbance of 0.2 or higher in the cell culture or periplasmic extract, and the base sequence of the antibody was analyzed for these clones. The base sequence analysis revealed that the colonies derived from the single hybridoma had the same sequences.

The CDR sequence of the antibody produced from each clone is summarized in Table 4 and Table 5.

TABLE 4

| Clones | CDRH1 | CDRH2 | CDRH3 |
| --- | --- | --- | --- |
| hz2G10 | DYYMY (SEQ ID NO 1) | YINSGGG STYYPDT VKG (SEQ ID NO 2) | EALYDYD YAMDY (SEQ ID NO 3) |
| hz39D2 | NYGVN (SEQ ID NO 7) | WINTHTGEP TYAEEFKG (SEQ ID NO 8) | DDYYVRV DY (SEQ ID NO 9) |

TABLE 4-continued

| Clones | CDRH1 | CDRH2 | CDRH3 |
|---|---|---|---|
| 24D3 | SCAMS (SEQ ID NO 13) | TISGGGS YTYYPDS VKG (SEQ ID NO 14) | HGGYESW FPY (SEQ ID NO 15) |
| 1G3 | DTYMH (SEQ ID NO 19) | RID PANGYTR YDPNFQG (SEQ ID NO 20) | YYYGFYA MDY (SEQ ID NO 21) |
| hz8G11 | GYYMH (SEQ ID NO 25) | HINPNNG GTSYNQK FKG (SEQ ID NO 26) | EEAFAY (SEQ ID NO 27) |

TABLE 5

| Clones | CDRL1 | CDRL2 | CDRL3 |
|---|---|---|---|
| hz2G10 | KSSQSLL YSNGKTY LN (SEQ ID NO 4) | LVSKLDS (SEQ ID NO 5) | VQGTHFP LT (SEQ ID NO 6) |
| hz39D2 | KASQDIN SYLS (SEQ ID NO 10) | RANRLVD (SEQ ID NO 11) | LQYDEFP WT (SEQ ID NO 12) |
| 24D3 | RSSQSLV HSNGNTY LH (SEQ ID NO 16) | KVSNRFS (SEQ ID NO 17) | SQSTHVP PWT (SEQ ID NO 18) |
| 1G3 | KASQDVS TAVA (SEQ ID NO 22) | SASYRYT (SEQ ID NO 23) | QQHYSTP PT (SEQ ID NO 24) |
| hz8G11 | RASQDIS NYLN (SEQ ID NO 28) | YTSRLHS (SEQ ID NO 29) | QQGITPP WT (SEQ ID NO 30) |

Tables 4 and 5 show the amino acid sequences of the heavy chain CDR (CDRH) and the light chain CDR (CDRL) of the developed antibodies.

Example 5: Specificity of Developed Antibody for HER2

It was investigated whether the developed five antibodies of the present disclosure specifically bind to HER2 belonging to the ErbB family proteins by ELISA. In order to confirm whether the developed antibody binds specifically to HER2 belonging to the ErbB family proteins, the extracellular domains of EGFR, HER2, HER3 and HER4 belonging to the ErbB family were examined via ELISA. The extracellular domain of EGFR (EGFR-ECD-Fc) was produced in the same manner as the HER2-ECD-Fc described above in Example 2, and the HER3 (R&D Systems, #348-RB-050) and HER4 (R&D Systems, #1131-ER-050) proteins were purchased. Cetuximab (CET), trastuzumab (TRA) and patritumab (AMG888, AMG) were used as control group antibodies binding to EGFR, HER2 and HER3, respectively.

Figure 4:
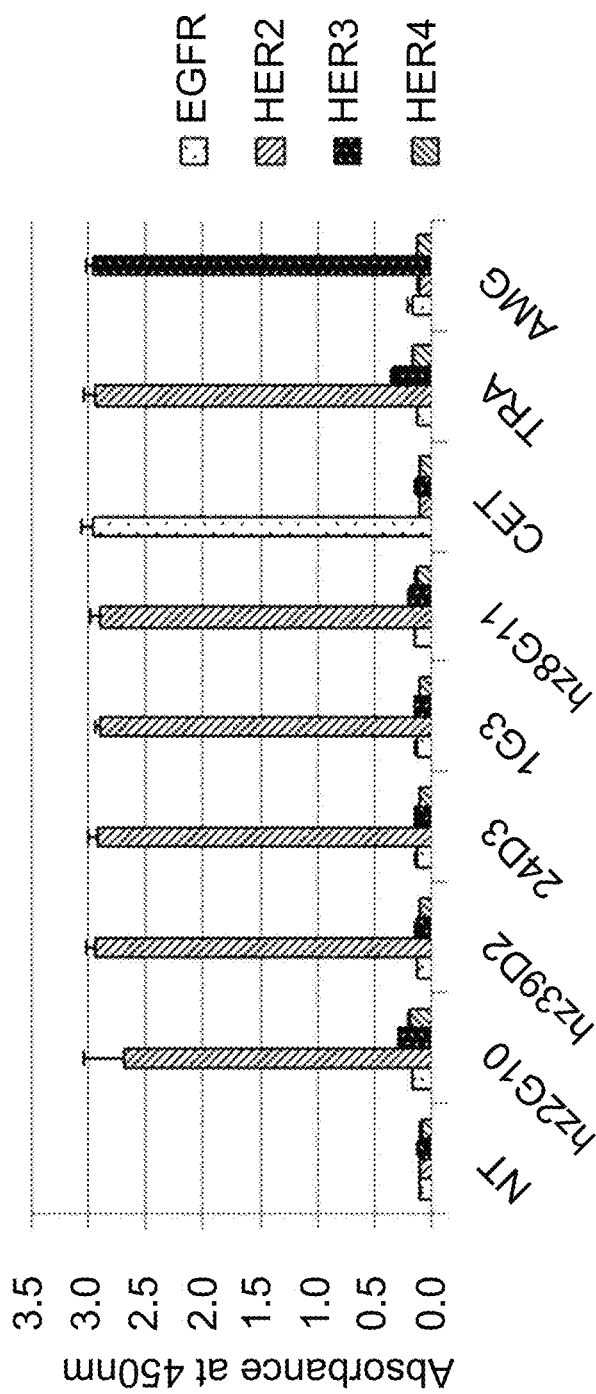
FIG. 4 is a bar graph showing the results of investigating the specificity of antibodies developed by expressing the ErbB family. Cetuximab (CET), trastuzumab (TRA) and patritumab (AMG888, AMG) were used as control groups binding to EGFR, HER2 and HER3, respectively.
Figure 5A:
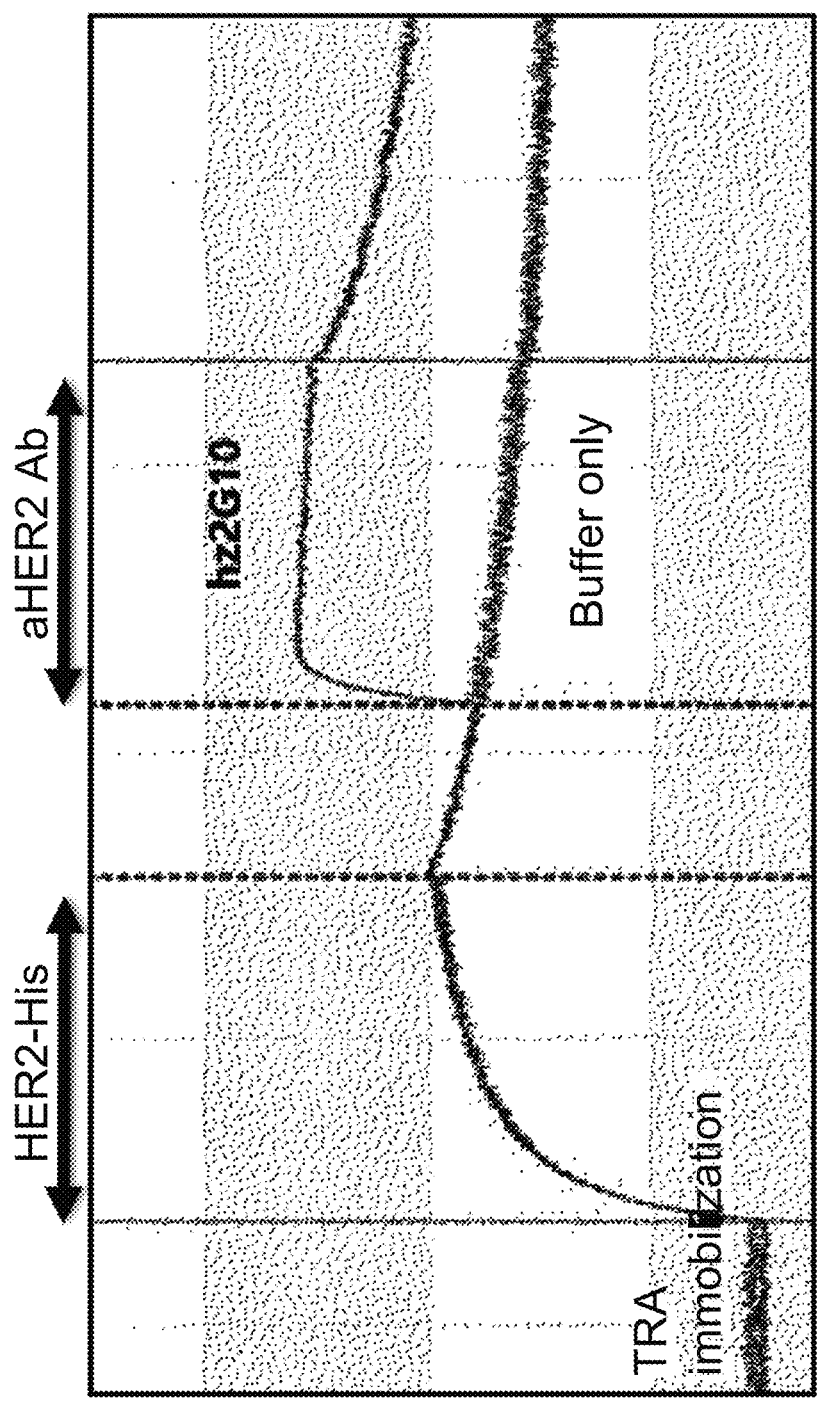
FIGS. 5A-5E are line graphs showing the results of comparing the epitopes of developed antibodies with trastuzumab. For comparison with the epitope of trastuzumab, trastuzumab and HER2-His were immobilized on a sensor chip and then the binding with five antibodies of the present disclosure was analyzed.
Figure 5B:
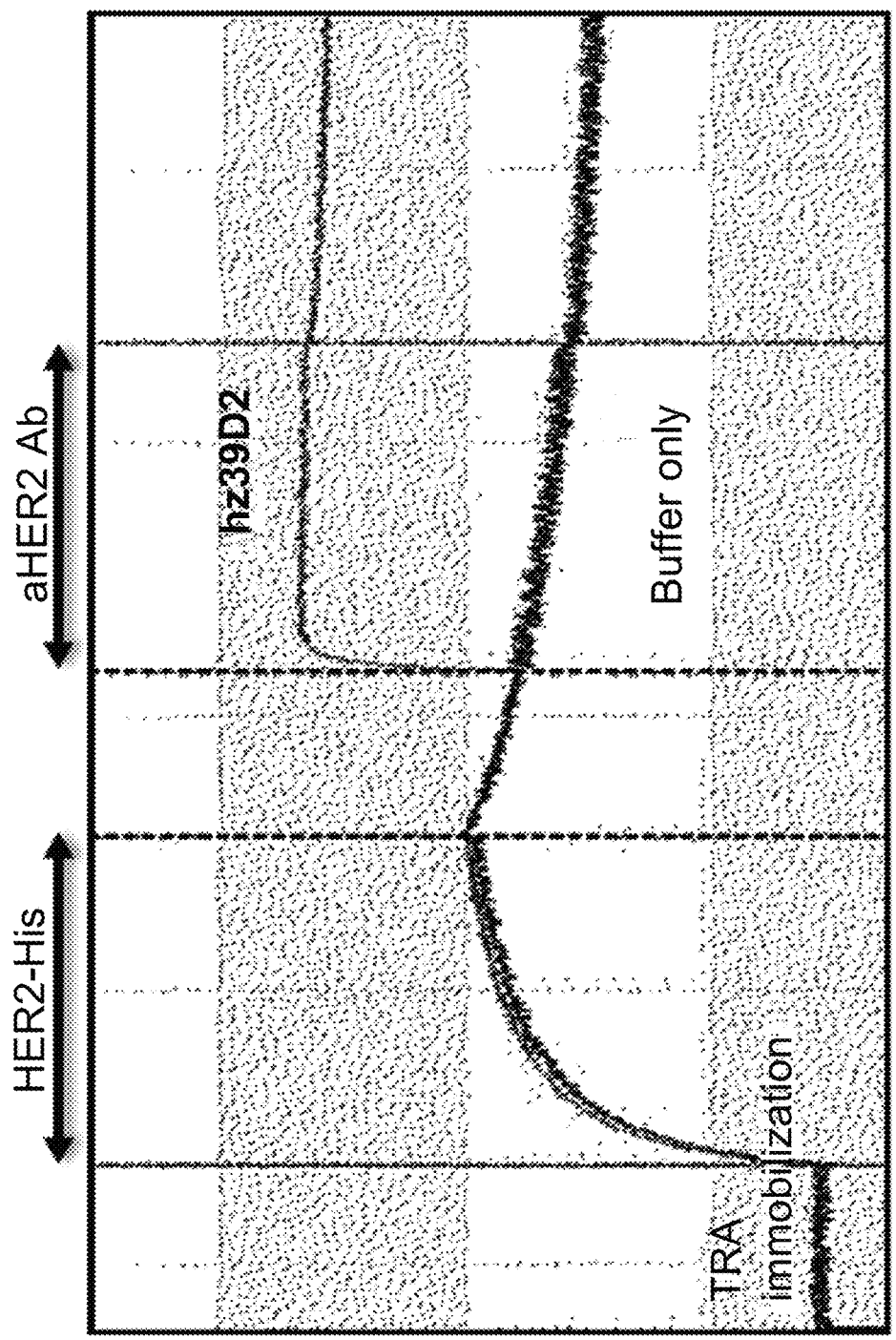
Figure 5C:
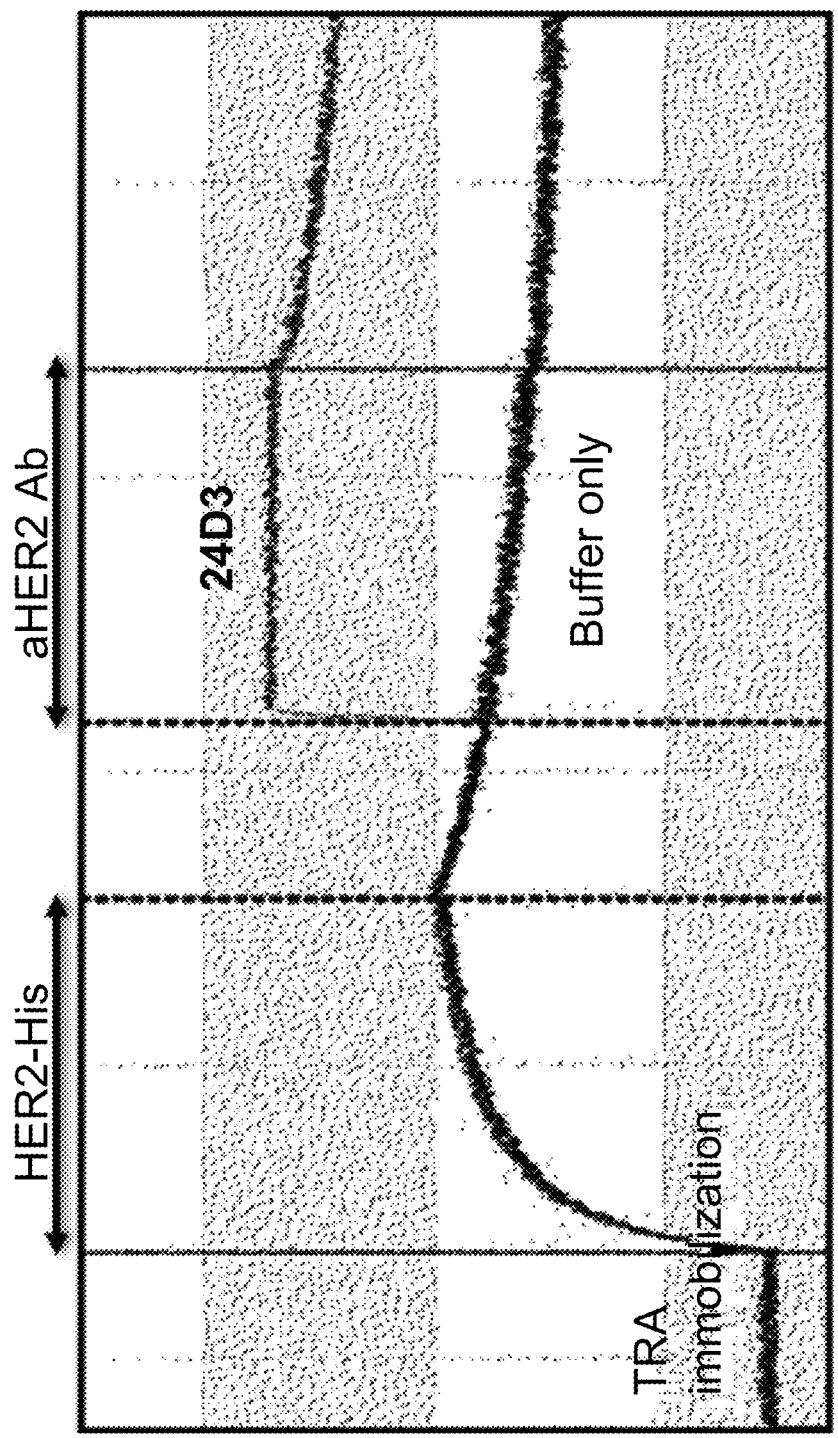
Figure 5D:
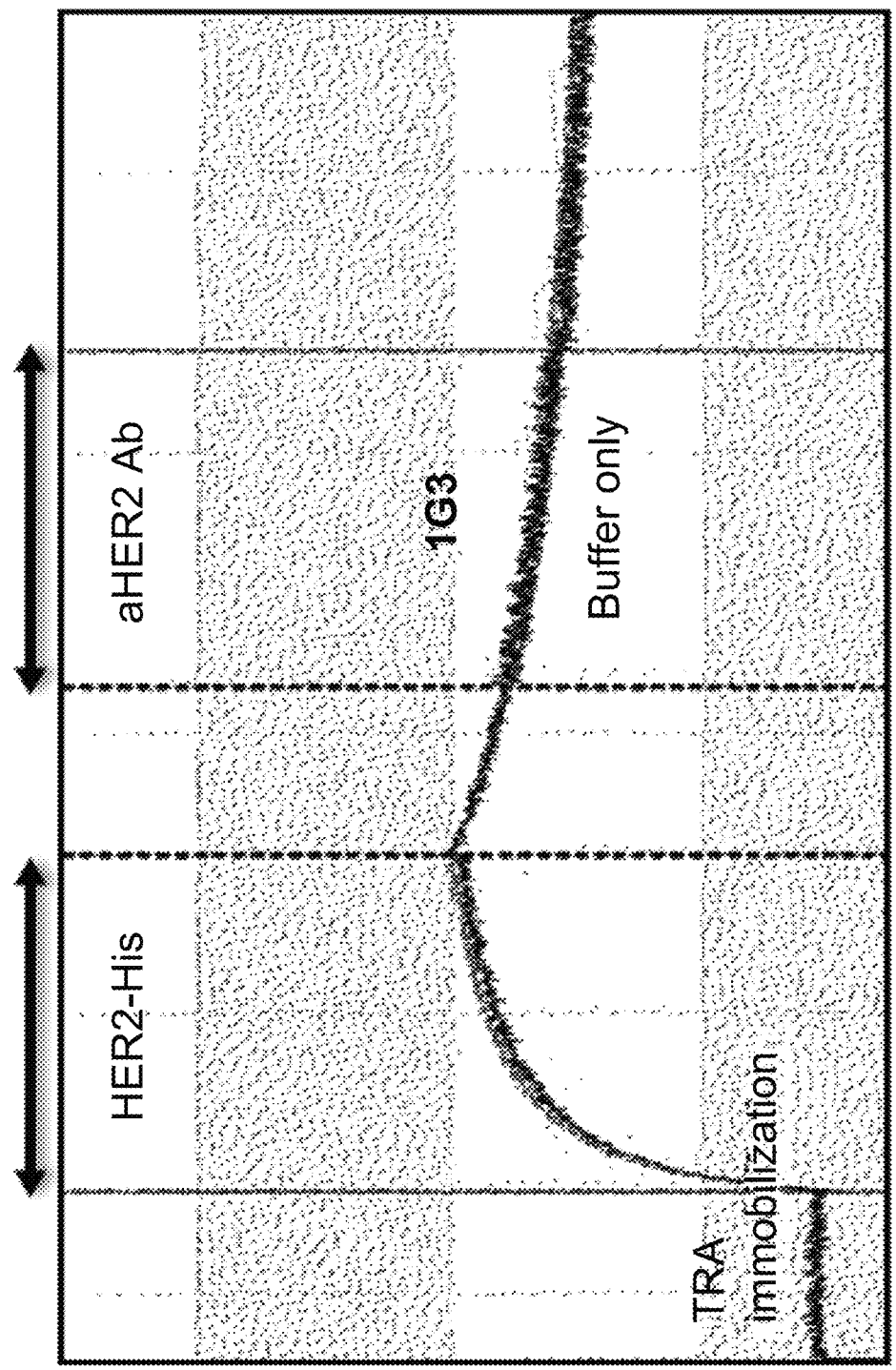
Figure 5E:
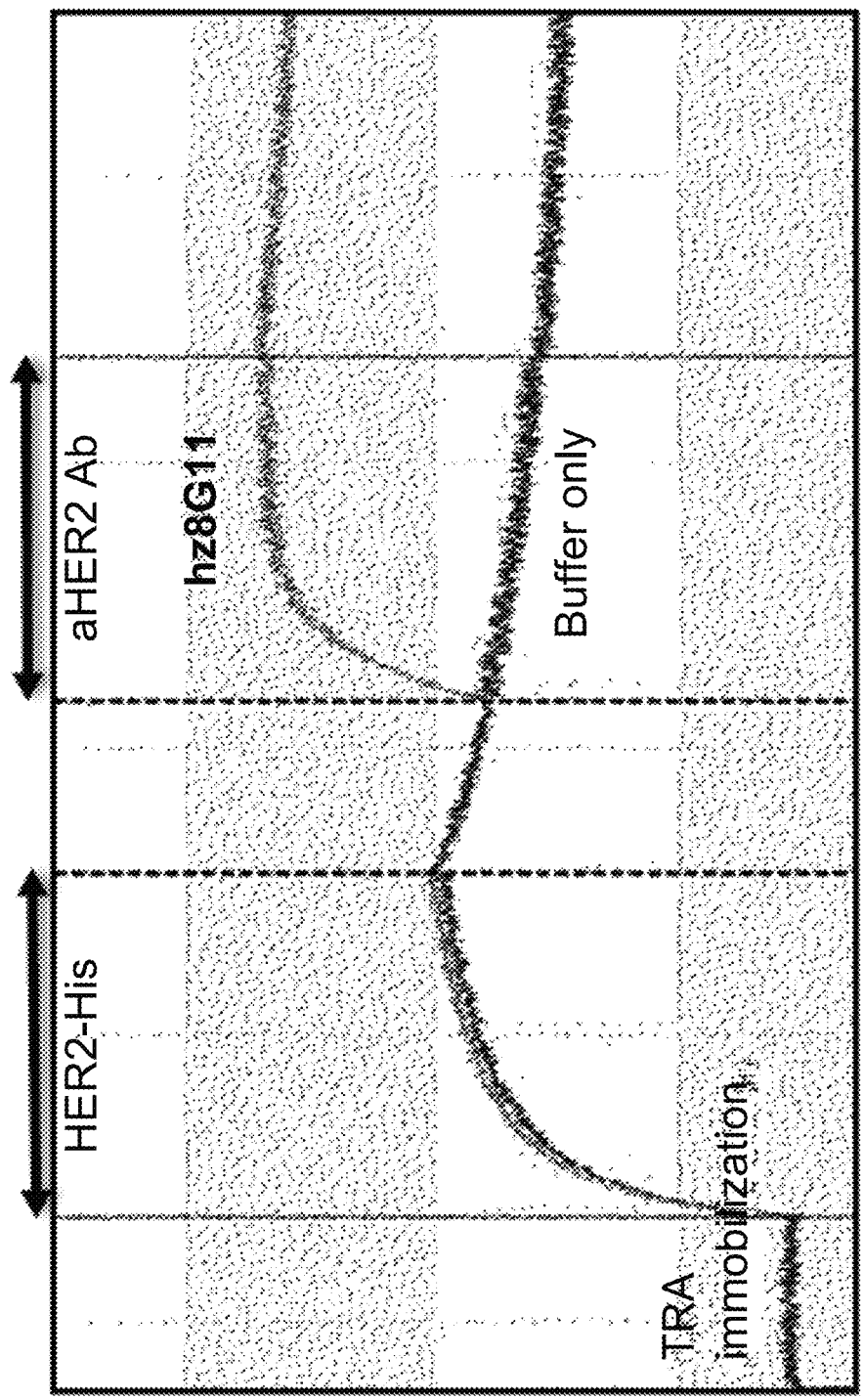

The result is shown in FIG. 4.

As seen from FIG. 4, it was confirmed that the five antibodies of the present disclosure bind specifically to HER2 among the human ErbB family proteins.

Example 6: Comparison of Epitopes of Developed Antibody and Trastuzumab

It is known that the anti-HER2 antibody trastuzumab binds to the domain 4 among the four domains of HER2 ECD. In order to investigate whether the developed antibodies and trastuzumab share the epitope for HER2, epitope binning was conducted using Octet (Pall ForteBio). Trastuzumab was immobilized onto an AR2G sensor chip (ForteBio, Cat. Nos. 18-5092 (tray), 18-5093 (pack), 18-5094 (case)) at a concentration of 10 µg/mL by amine coupling using ECD/NHS. After allowing the HER2-ECD-His protein to bind to the trastuzumab-immobilized sensor chip at a concentration of 10 g/mL for 10 minutes, the binding between trastuzumab and HER2-ECD was stabilized for 5 minutes. Then, the five antibodies of the present disclosure were bound at a concentration of 10 µg/mL for 10 minutes and the binding between the antigen and the antibodies was stabilized for 10 minutes. After the immobilization of trastuzumab, all the antibodies and antigen were diluted using a kinetics buffer (ForteBio, Cat No. 18-1092). The same buffer was used during the stabilization. If the additionally added antibody binds to the trastuzumab-bound HER2-ECD protein, it can be interpreted that the antibody does not share the epitope with trastuzumab.

The result is shown in FIGS. 5a-5e.

As seen from FIGS. 5a-5e, it was confirmed that the developed antibodies hz2G10, hz39D2, 24D3 and hz8G11 had different epitopes from that of trastuzumab because they were bound to the trastuzumab-bound HER2-ECD. In contrast, 1G3 did not bind to the trastuzumab-bound HER2-ECD, suggesting that it shares the epitope with trastuzumab.

Example 7: Development of hz39D2 Antibody with Increased Affinity

In order to develop antibodies with improved affinity based on the humanized 39D2 antibody (hz39D2), the inventors of the present disclosure have developed a phage antibody library with CDR3 of the light chain or heavy chain randomized (Phage display: a laboratory manual, Carlos Barbas III, et al., Cold Spring Harbor Laboratory Press). D and Y corresponding to D101 and Y102 of the CDR3 of the heavy chain according to Kabat numbering and P, W and T corresponding to P95, W96, T97 of the CDR3 of the light chain according to Kabat numbering were excluded from the randomization because they are commonly observed amino acids in human antibodies. Primers were synthesized such that adenine (A), cytosine (C), guanine (G) and thymine (T) were inserted randomly into the first and second positions of the codon corresponding to the amino acid to be randomized, with the same ratio, and guanine (G) or cytosine (C) was inserted into the third position at the same ratio. From the developed library, the clones with improved affinity were selected through biopanning using the HER2-ECD-His protein. The CDR sequence data of the finally selected three antibodies, hz39D2.14, hz39D2.22 and hz39D2.23, are summarized in Table 6 and Table 7. The amino acid residues modified to improve affinity are underlined.

TABLE 6

| Clones | CDRH1 | CDRH2 | CDRH3 |
|---|---|---|---|
| hz39D2 | NYGVN (SEQ ID NO 7) | WINTHTGEP TYAEEFKG (SEQ ID NO 8) | DDYYVRV DY (SEQ ID NO 9) |
| hz39D2.14 | NYGVN (SEQ ID NO 7) | WINTHTGEP TYAEEFKG (SEQ ID NO 8) | DEYYVRT DY (SEQ ID NO 71) |
| hz39D2.22 | NYGVN (SEQ ID NO 7) | WINTHTGEP TYAEEFKG (SEQ ID NO 8) | DEYYVRV DY (SEQ ID NO 72) |
| hz39D2.23 | NYGVN (SEQ ID NO 7) | WINTHTGEP TYAEEFKG (SEQ ID NO 8) | DEYYVRV DY (SEQ ID NO 73) |

TABLE 7

| Clones | CDRL1 | CDRL2 | CDRL3 |
|---|---|---|---|
| hz39D2 | KASQDIN SYLS (SEQ ID NO 10) | RANR LVD (SEQ ID NO 11) | LQYDEFP WT (SEQ ID NO 12) |
| hz39D2.14 | KASQDIN SYLS (SEQ ID NO 10) | RANR LVD (SEQ ID NO 11) | LQYDEFP WT (SEQ ID NO 12) |
| hz39D2.22 | KASQDIN SYLS (SEQ ID NO 10) | RANR LVD (SEQ ID NO 11) | LELDEFP WT (SEQ ID NO 73) |
| hz39D2.23 | KASQDIN SYLS (SEQ ID NO 10) | RANR LVD (SEQ ID NO 11) | LQLDEFP WT (SEQ ID NO 74) |

IgG antibodies were produced to verify the increased affinity of the three selected antibodies (hz39D2.14, hz39D2.22 and hz39D2.23). 2000 RU of goat anti-human IgG (Invitrogen, #H10500) was immobilized onto a CM5 sensor chip by ECD/NHS. Then, the antibodies were allowed to bind at a rate of 50 μL/min for 5 minutes and then stabilized for 5 minutes by flowing a buffer. After stabilizing the antibodies, the HER2-ECD-His protein was allowed to bind at a rate of 50 μL/min for 4 minutes and then separated by flowing a buffer for 15 minutes. After analyzing the concentration, the resultant was recycled using 10 mM glycine (pH 1.5) and then subjected to the subsequent assay. The affinity of the antibodies was analyzed using the BIAevaluation software. The analysis result is summarized in Table 8. As seen from Table 8, all of the three selected antibodies (hz39D2.14, hz39D2.22 and hz39D2.23) showed improved affinity as compared to hz39D2.

TABLE 8

| Clones | $K_a$ (1/Ms) | $K_d$ (1/s) | $K_D$ (M) |
|---|---|---|---|
| hz39D2 | 6.8E+04 | 2.5E−03 | 3.7E−08 |
| hz39D2.14 | 3.7E+04 | 3.0E−04 | 8.0E−09 |
| hz39D2.22 | 8.1E+04 | 1.6E−04 | 2.0E−09 |
| hz39D2.23 | 7.1E+04 | 2.0E−04 | 2.8E−09 |

Figure 6A:
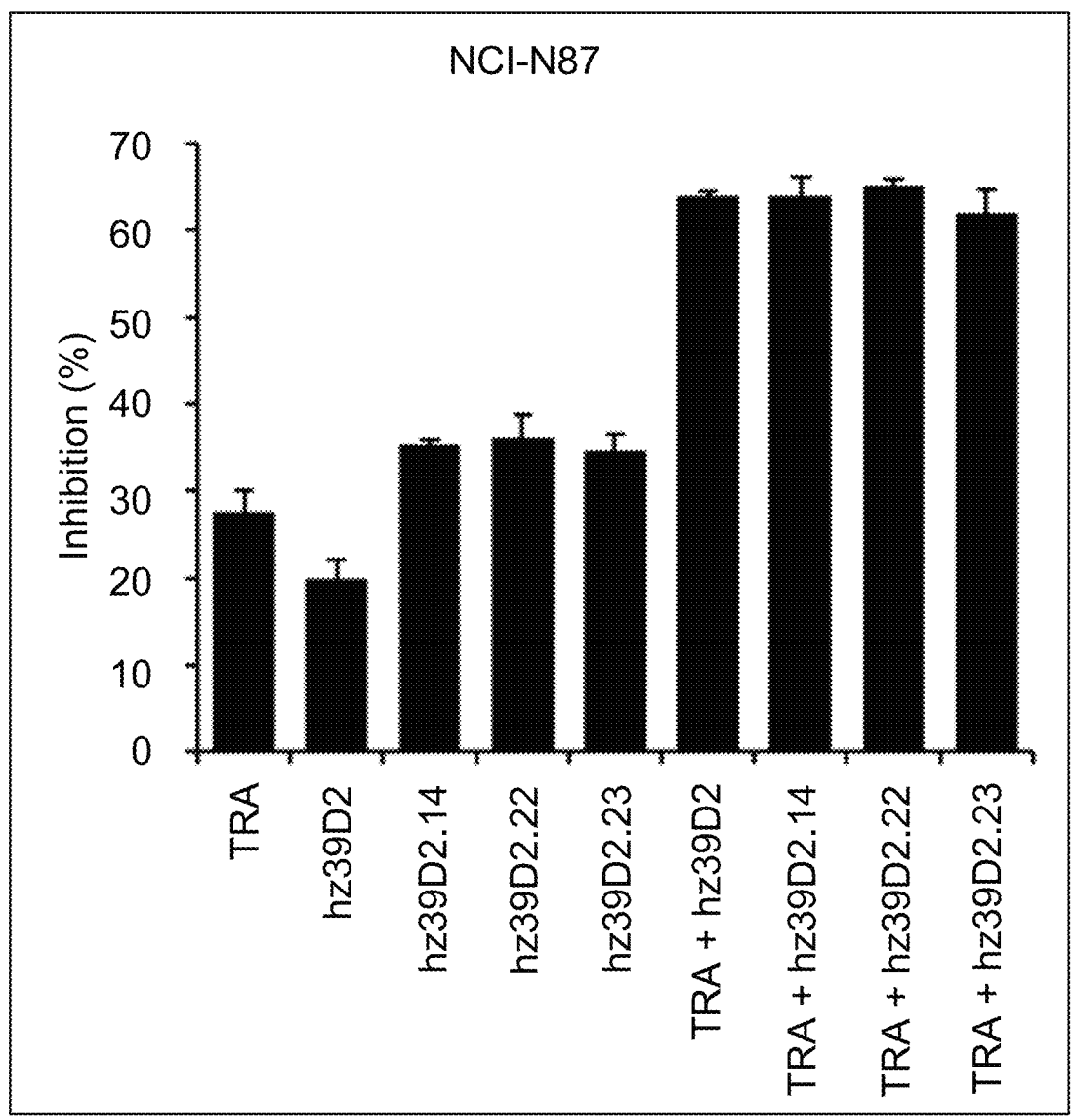
FIGS. 6A-6C are bar graphs showing the results of analyzing the effect of single administration of hz39D2 and affinity-improved clones thereof (hz39D2.14, hz39D2.22 and hz39D2.23) or co-administration with the trastuzumab antibody on the inhibition of the growth of HER2-overexpressed gastric cancer and breast cancer cells.
Figure 6B:
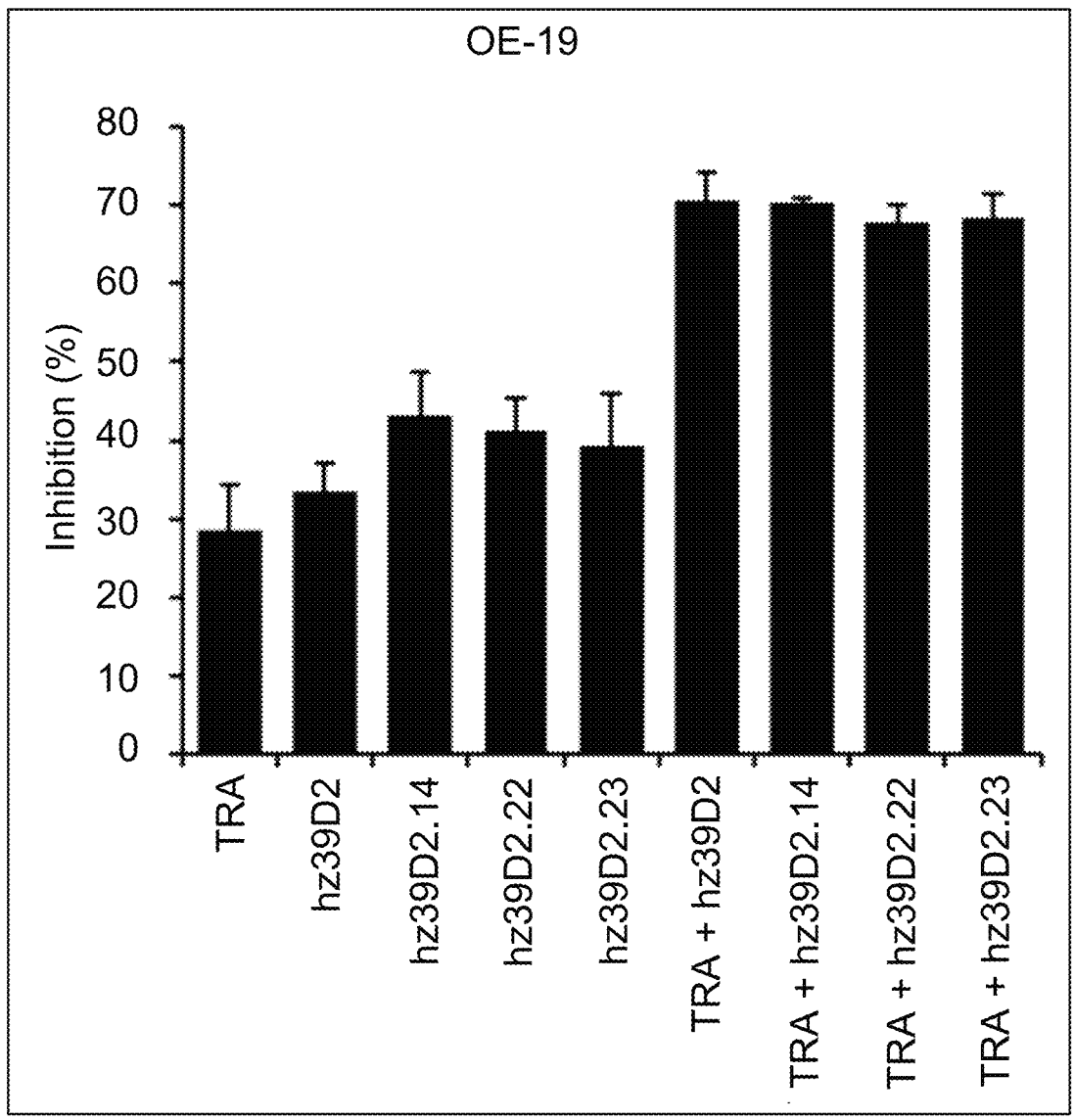
Figure 6C:
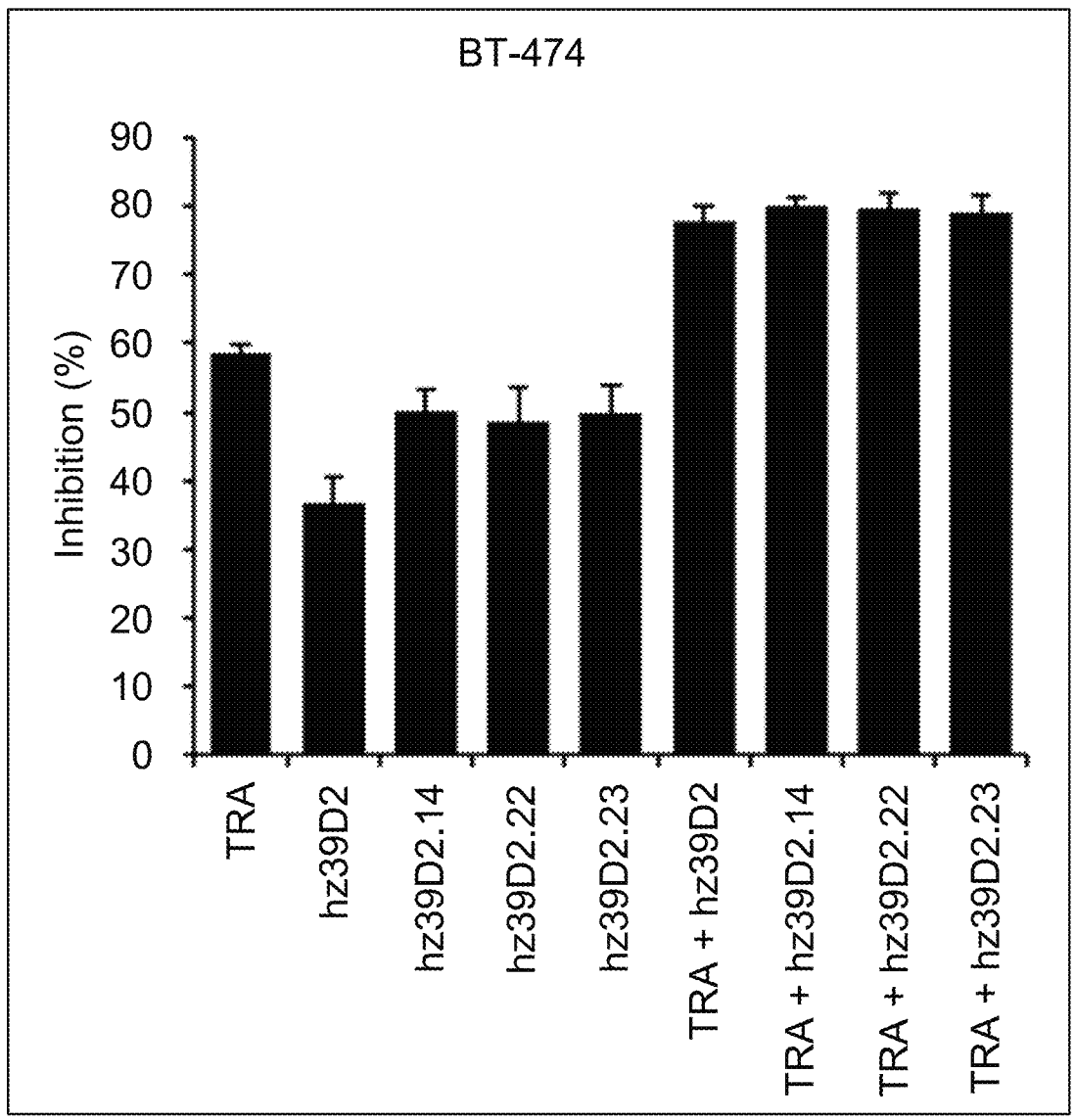
Figure 9B:
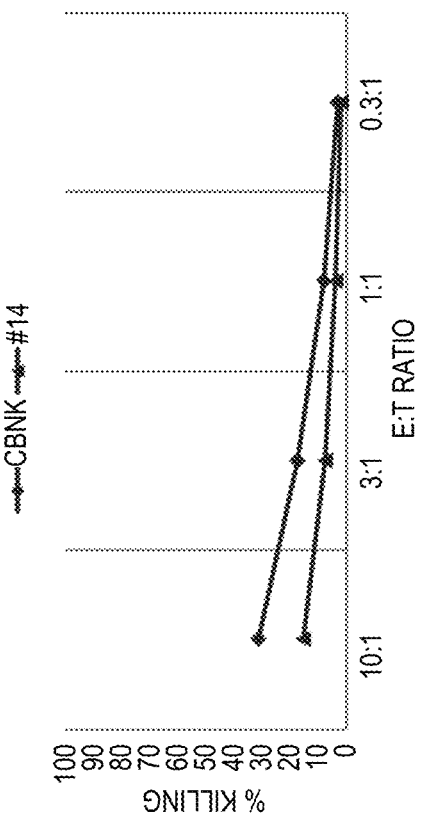
FIGS. 9A-9E are line graphs showing the results of a cell killing assay (Calcein releasing cytotoxicity assay) assessing the cytotoxicity of cord-blood derived NK cells expressing HER2-CAR construct clone #14 against HER2 positive target cancer cell lines.
Figure 9A:
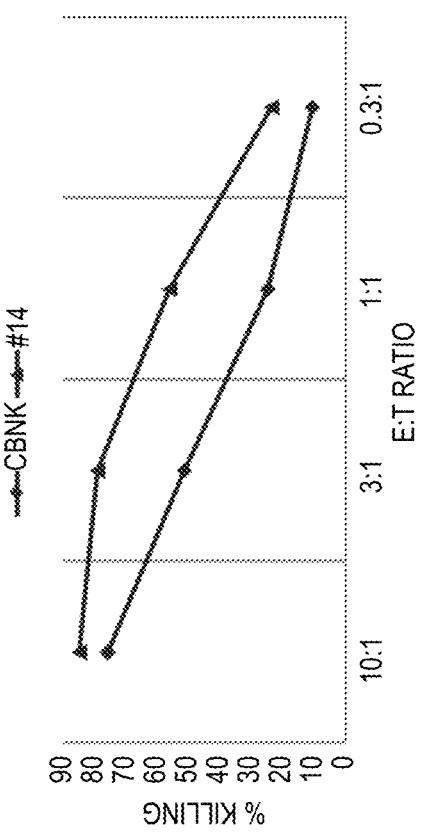
Figure 9C:
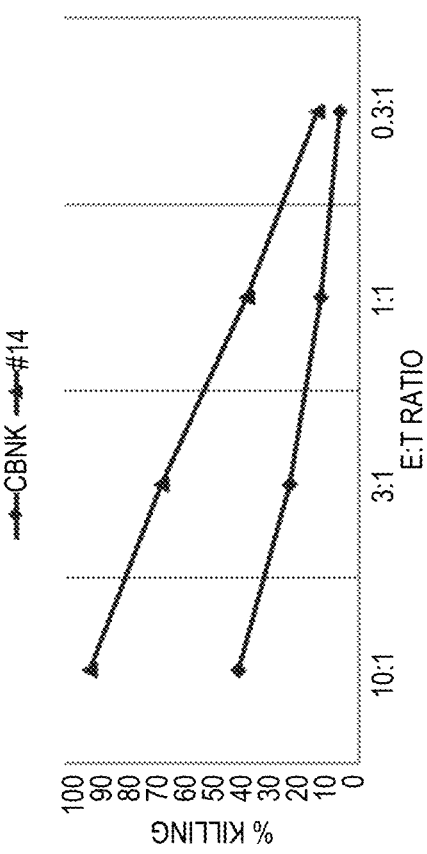
Figure 9D:
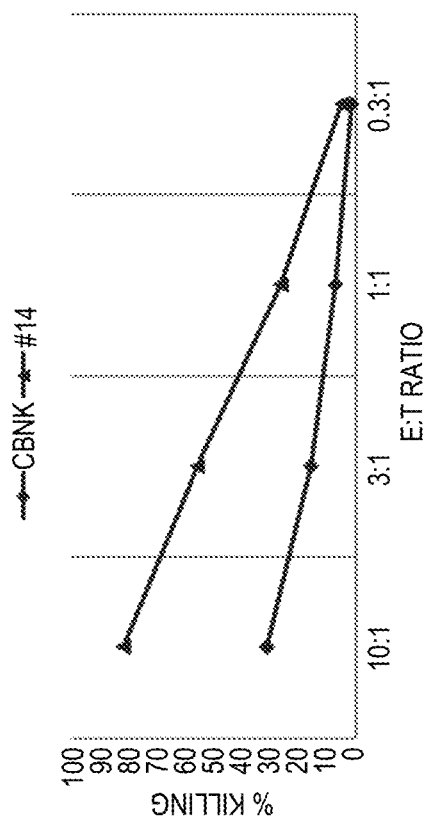
Figure 9E:
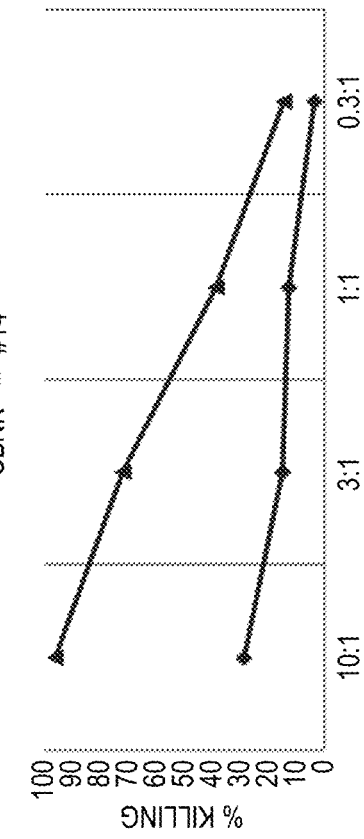

The anticancer effect of the three antibodies (hz39D2.14, hz39D2.22 and hz39D2.23) with improved affinity was analyzed using HER2-overexpressed NCI-N87 and OE-19 gastric cancer cells and BT-474 breast cancer cells. After treating the cells with each antibody at a concentration of 5 μg/mL either alone or in combination with trastuzumab, the viability of the cancer cells was analyzed (FIGS. 6a-6c). As seen from FIGS. 6a-6c, it was confirmed that the hz39D2.14, hz39D2.22, and hz39D2.23 antibodies with improved affinity showed improved effect of inhibiting cancer cell proliferation when treated alone.

Example 8: Construction of Chimeric Antigen Receptors (CAR) Targeting Human HER2

Various CAR domain structures were constructed, cloned into lentivral expression systems, expressed in Umbilical Cord Blood-derived Natural Killer cells and tested in assays of tumor cell engagement and cytotoxic killing. The Anti-Her2 antibody disclosed herein was constructed as a scFv structure and used in combination with various CAR costimulatory domains as described herein.

Plasmid Construction: A signal sequence comprising the scFv of Her2 specific hz39D2 (VL-GS linker-VH), a hinge and transmembrane domain of CD8a, and intracellular domains of 4-1BB, OX40, OX40 ligand, and CD3 (were each independently synthesized. These molecules were assembled in various combinations using splicing by overlap extension PCR (SOE-PCR). The sequences of the PCR products were confirmed by direct sequencing. Each PCR product was cut into Nhe1 and EcoRI, and then inserted into Nhe1 and EcoRI sites of a 3rd generation self-inactivating lentiviral expression vector such as MSCV-EF1α-GFP vector or EF1a-MCS vector.

Her2-Z CAR (Clone #2) (SEQ ID NO: 129) was produced by connecting: the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); human CD8α-derived hinge and transmembrane domains (nucleotides 1292-1507, GenBank NM 001768.6, SEQ ID NO: 116 and SEQ ID NO: 118); CD3ζ-derived intracellular signaling domain (nucleotides 299-634, GenBank NM 000734.3, SEQ ID NO: 122); and stop codon TGA.

Her2-BBZ CAR (Clone #3) (SEQ ID NO: 131) was produced by connecting: the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); human CD8α-derived hinge and transmembrane domains (nucleotides 1292-1507, GenBank NM 001768.6, SEQ ID NO: 116 and SEQ ID NO: 118); CD137 (4-1BB)-derived intracellular signaling domain (nucleotides 901-1026, GenBank NM 001561.5, SEQ ID NO: 124); CD3ζ-derived intracellular signaling domain (nucleotides 299-634, GenBank NM 000734.3, SEQ ID NO: 122; and stop codon TGA.

Her2-28Z CAR (Clone #6) (SEQ ID NO: 133) was produced by connecting the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); human CD8α-derived hinge domain (nucleotides 1292-

1435, GenBank NM 001768.6, SEQ ID NO: 116; CD28-derived transmembrane and intracellular signaling domains (nucleotides 679-882, GenBank NM 006139.3, SEQ ID NO: 120 and SEQ ID NO: 126); CD3ζ-derived intracellular signaling domain (nucleotides 299-634, GenBank NM 000734.3, SEQ ID NO: 122); and stop codon TGA.

Her2-28OX40LZ CAR (Clone #14) (SEQ ID NO: 135) was produced by connecting: the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); CD8α-derived hinge domain (nucleotides 1292-1435, GenBank NM 001768.6, SEQ ID NO: 116); CD28-derived transmembrane and intracellular signaling domains (nucleotides 679-882, GenBank NM 006139.3, SEQ ID NO: 120 and SEQ ID NO: 126); CD252 (OX40 ligand)-derived intracellular signaling domain (nucleotides 141-206, GenBank NM 003326.4, SEQ ID NO: 128); CD3ζ-derived intracellular signaling domain (nucleotides 299-634, GenBank NM 000734.3, SEQ ID NO: 122); and stop codon TGA.

The structures of the HER2 CAR constructs as disclosed herein are summarized in FIG. 7. The domains of the CARs disclosed herein were linked in series (in tandem) to one another and linked in frame. Virus Production and Gene Transfer: To prepare VSVG-pseudotyped lentivirus, 293T cells cultured in a DMEM medium were co-transfected with various types of vectors such as PCDH1-MSCV-Her2 specific hz39D2 scFv-construct-EF1-copGFP vector, EF1a-Her2 specific hz39D2 scFv-construct vector, PCDH1-MSCV-EF1-copGFP control vector, or EF1a-GFP control vector (for production of Mock infection virus using empty vector) together with HIV-based pPACKH1 lentivirus Package Kit (System Biosciences). For this purpose, Lipofectamine 2000 reagent (Invitrogen, Carlsbad, CA) was used. Each lentivirus was prepared by transfection of 80% dense HEK293T cells in a flask with the various Her2 specific hz39D2 scFv construct expression vectors or a control plasmid together with pPACKH1 lentivirus packaging plasmids. After 6 hours, the medium was replaced by a DMEM medium containing 10% FBS. The conditioned medium containing lentivirus was collected after 48 hours of transfection, followed by filtering with a 0.45 m filter unit (Milliopore, Billerica, MA, USA) in order to remove cell debris. A viral supernatant containing the virus was concentrated about 50 times by centrifugation at 3000 rpm and 4° C. for 20 minutes using Amicon Filter (Millipore). The concentrated virus was stored at −80° C.

For the lentiviral infection, PBMC derived NK cells or cord blood derived NK cells in an exponential growth phase were adjusted to a concentration of $1\times10^6$ cells/ml using Cellgro (Cellgenix) including 1% human plasma and 500 IU/mL interleukin-2, and then a lentiviral supernatant in 10 to 50 MOI was added in the presence of 4 μM BX795, 1:400 Lentiboost and 20 ng/ml IL-21 followed by centrifugation at 1000 g for 60 minutes. After centrifugation, the cells were left in a humidified incubator at 37° C. and 5% $CO_2$ conditions. After 24 hours of transduction, the culture medium was replaced: plate was centrifuged at 400 g for 5 minutes and transduction medium was aspirated. Equal volume fresh Cellgro (Cellgenix) including 1% human plasma and 500 IU/mL interleukin-2 was added for future use. Control cells were transduced with a vector only.

Expression Analysis of Anti-HER2-CAR (hz39D2 scFv): Her2 specific hz39D2 scFv CAR-transduced NK cells, the control vector-transduced NK (NK-Mock) or NK parent cells were washed twice with FACS buffer, and the washed cells were stained using 7-AAD (Beckman coulter), anti-CD3, anti-CD56, and recombinant histidine tagged human HER2 proteins (R&D systems) with PE-conjugated anti-histidine (Abcam) mAbs. An expression ratio and a mean fluorescence intensity (MFI) of the stained cells were measured using a BD LSRFortessa.

First, NK cells were gated in regard to singlet, and then gated in regard to 7AAD- and CD3−CD56+. The transduction efficiency of the Her2 specific hz39D2 scFv CAR constructs was determined by flow cytometric analysis of cells expressing CAR among CD3−CD56+ cells.

Example 9: Cytotoxic Activity of Anti-Her2 CAR Constructs in NK Cells

Cells: The human breast cancer cell line HCC1954, SKBR3 and MDA-MB 468, ovarian cancer cell line SKOV-3, gastric cancer cell line N87 and human erythroleukemic cell line K562 were obtained from the American Type Culture Collection (ATCC) (Manassas, VA, USA). HCC1954, N87, SKOV-3 and K562 were maintained in RPMI-1640 (ATCC) (Manassas, VA) with 10% fetal bovine serum (FBS; Gibco, Grand Island, NY, USA). SKBR3 and MDA-MB 468 were maintained in DMEM (Gibco, Grand Island, NY, USA) with 10% FBS. PBMC or cord blood derived NK cells and transduced NK cells were maintained in CellGro® serum-free media+1% human plasma+500 IU/mL interleukin-2. Human embryonic kidney fibroblast 293T cells were obtained from the ATCC and maintained in DMEM (Gibco, Grand Island, NY, USA) supplemented with 10% FBS % (Gibco, Grand Island, NY, USA).

Calcein Releasing Cytotoxicity Assay: Target cells were labeled at 37° C. for 1 hour with 30 μM calcein-acetoxymethyl ester (Calcein-AM; Molecular probes). After washing, the labeled target cells were dispensed to $1\times10^4$ cells per well in 96-well plates. Control or CAR transduced NK cells were harvested, washed, and then were added at different E/T (effector-to-target) ratios. After 2 hours, the plates were centrifuged at 2000 rpm for 3 minutes, and a supernatant of 100 μL was collected and subjected to measurement of calcein release using a fluorescence microplate reader (Victor3, PerkinElmer) at an excitation wavelength of 485 nm and an emission wavelength of 535 nm. Specific calcein release amount was calculated by the following equation: percent specific lysis=(test release−spontaneous release)×100/(maximal release−spontaneous release). For maximal lysis, a 1% Triton X-100 solution was used.

Comparison of CAR Constructs in vitro Her2+ Cell Killing: The cell killing activities of clone #2, #6 and #14 were compared against various target cells. Cord-blood derived NK (CBNK) cells were transduced with each construct using lentiviral vector system at 40 multiplicity of infection (MOI) at day 7 after culture, followed on day 11 by a positive magnetic activated cell sorting (MACS) process for HER-2-CAR-NK expressing cells. As controls, we used unmodified CBNK and mock-transduced CBNK that was transduced with lentivirus vector harboring GFP gene instead of the CAR genes. Killing assay (Calcein releasing cytotoxicity assay) was performed using HER2 positive target cancer cell lines: SKBR3 (breast cancer), HCC1954 (breast cancer, trastuzumab resistant), NCI-N87 (gastric cancer) at different ratios of effector to target cells (5:1, 2.5:1, 1:1). All of the HER-2-CAR-NKs showed higher cytotoxicity to HER-2 expressing target cells than non-transduced or mock vector transduced NK cells. Clone #14 showed unexpectedly the highest cytotoxicity to all three target cells (FIGS. 8A-8C).

The killing activity of clone #14 was further assessed by testing its cytotoxicity to various cancer cell lines: K562 (lymphoblast, HER-2 negative, but NK susceptible control), MDA-MB-468 (breast cancer, HER-2 negative), SKOV3 (ovarian cancer, HER-2 positive), NCI-N87 (gastric cancer, HER-2 positive), and trastuzumab-resistant cell line HCC1954 (breast cancer, HER-2 positive). The cytotoxicity of clone #14 was compared with unmodified CBNK at various ratios of effector to target cells (10:1, 3:1, 1:1 & 0.3:1). Clone #14 showed significantly higher and unexpected cytotoxicity against HER2 positive cancer cell lines than unmodified CBNKs. HER2-CAR-NK was also active on HCC1954 (breast cancer, HER-2 positive), which has previously seen to be resistant to trastuzumab mAb treatment (FIGS. 9A-9E).

Figures 10A, 10B:
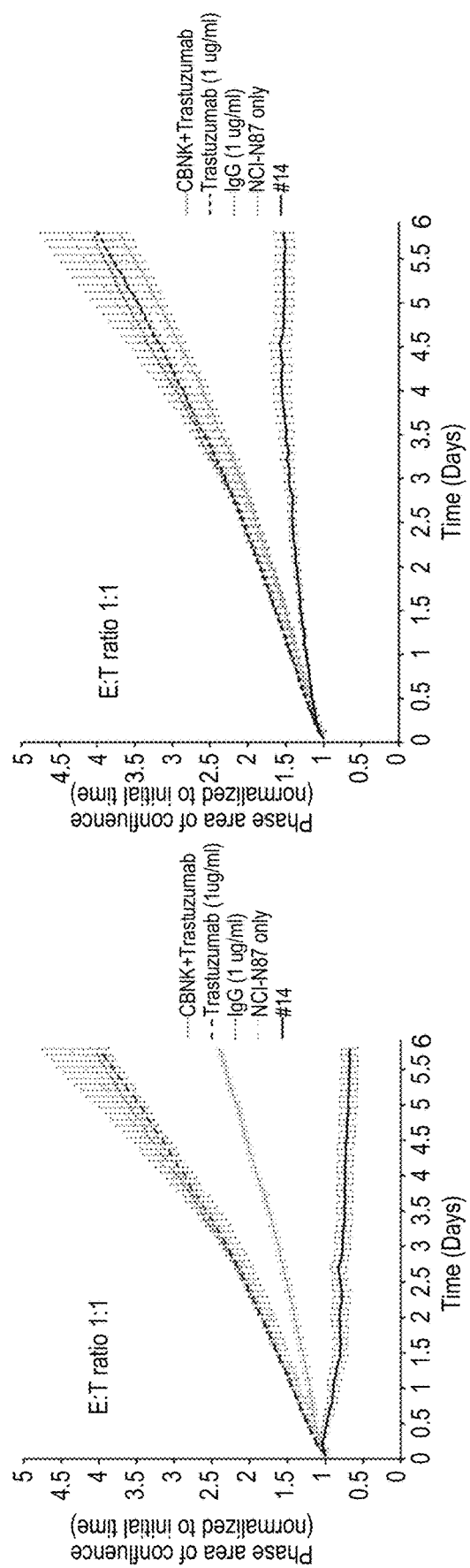
FIGS. 10A-10B are line graphs showing the long-term serial killing activity of HER2-CAR clones #6 and #14 assessed using the Incucyte live cell imaging system.

In vitro Long-Term Her2+ Cell Killing: The long-term serial killing activity of clones #6 & #14 was assessed using the Incucyte live cell imaging system. NCI-N87 Her2+ gastric carcinoma target cells were grown and monitored in the Incucyte system for 6 days in the presence of: control, non-specific IgG, trastuzumab (anti-Her2 monoclonal antibody), CBNK cells, CBNK cells in combination with trastuzumab, or CBNK transduced with clone #14 CAR construct. The experiment was completed at effector to the target (E:T) cellular ratios of 1:1 and 0.3:1. Unexpectedly, clone #14 killed significantly more Her2+ target cells than either CBNKs or CBNK in combination with tastuzumab for both the E:T 1:1 and 0.3:1 conditions (FIGS. 10A and 10B).

Example 10: NK Cell Activation by Anti-Her2-CAR Constructs in Response to Target Cells Intercellular Cytokine Staining (ICS) Assay for CD107a, IFN-γ, and TNF-α: To measure intracellular cytokines and CD107a of NK cells, NK cells were co-cultured with tumor targets at 1:1 ratio for 4 h in the presence of anti-CD107a-APC (H4A3; BD Biosciences, USA), GolgiStop™ and GolgiPlug™ (BD Bioscience, USA). After 4 hours, cells were washed with BD FACS flow buffer and stained with anti-CD3-FITC, anti-CD56-APC-eFluor®780, and 7-AAD permeabilized by BD CytoFix/CytoPerm™ and then stained with anti-IFN-7-PE (B27; BD Biosciences) and anti-TNF-α-PE-Cy7 (Mab11; eBioscience). Stained cells were acquired on LSR Fortessa and data analysis was conducted using FlowJo software (TreeStar Inc., OR).

Figure 11B:
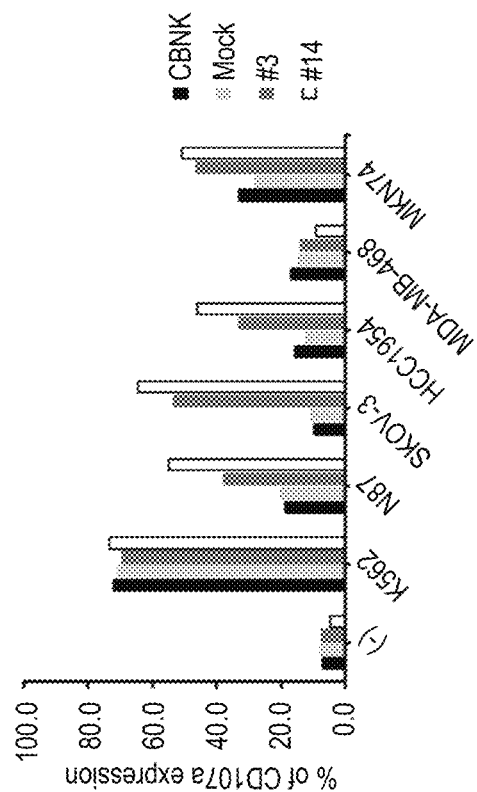
FIGS. 11A-11B are bar graphs showing the NK cell degranulation activity and cytotoxic cytokine expression with the various HER2-CAR constructs evaluated by comparing intercellular expression level of CD107a and IFN-7.
Figure 11A:
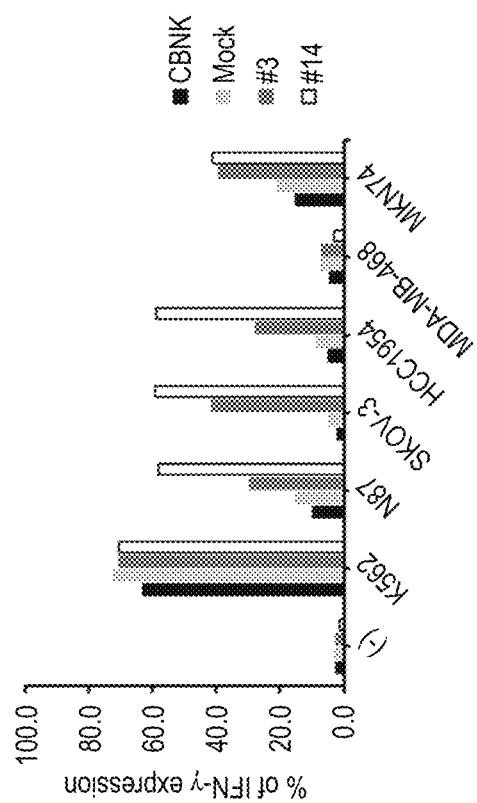

NK cell degranulation activity and cytotoxic cytokine expression with the various CAR constructs was evaluated by comparing intercellular expression level of CD107a & IFN-γ. Umbilical Cord blood-derived NK (CBNK) cells transduced with clone #3, clone #14 lentivirus were compared with control CBNK cells and CBNK cells with mock lentiviral transduction. NK cells expressing clone #3, clone #14 and control cells were co-cultured with target cancer cells: K562 (HER2-negative, but susceptible to NK cell), NCI-N87, SKOV3, HCC1954, MKN74 (HER-2 negative), and MDA-MB-468 (HER-2 negative) at 1:1 ratio of effector to target cells for 2 hrs, followed by FACS analysis gating CD56+/CD107a or CD56+/IFN-γ. Both clones #3 & #14 showed an increase in intercellular expression of CD107a & IFN-γ in response to HER-2 positive target cells. Unexpectedly, clone #14 showed consistently greater degranulation activity and IFN-γ expression than clone #3 (FIG. 11A and FIG. 11B).

Figure 12A:
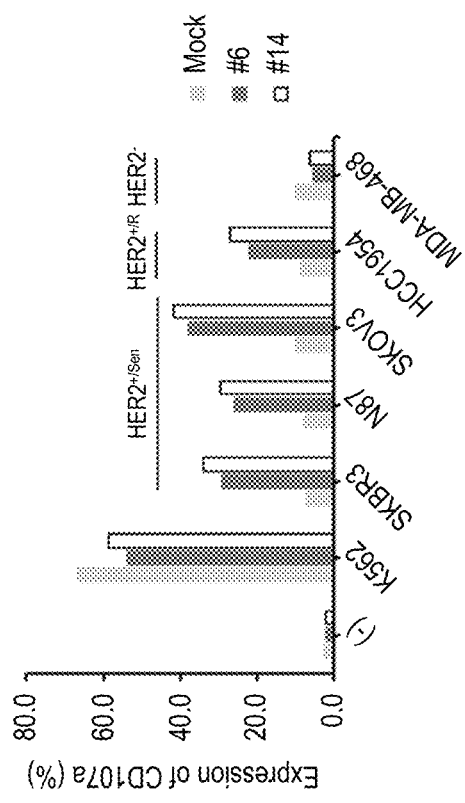
FIGS. 12A-12C are bar graphs showing NK cell degranulation activity and cytotoxic cytokine expression of HER2-CAR clones #6 and #14 evaluated by comparing intercellular expression level of CD107a, IFN-γ, and TNF-α.
Figure 12B:
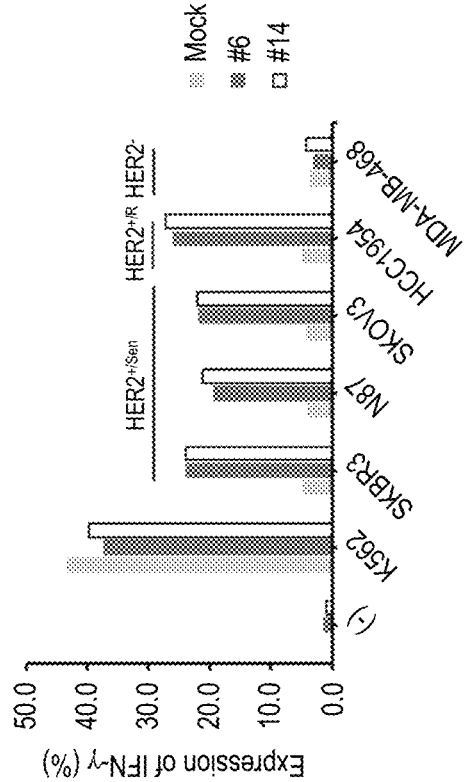
Figure 12C:
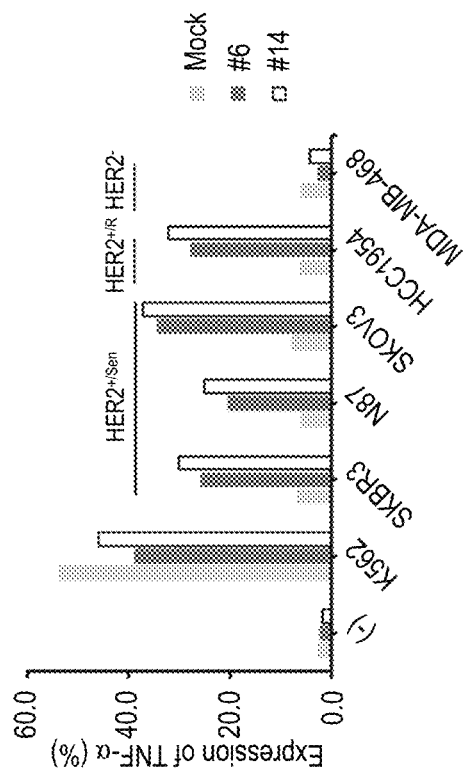

A similar assay was performed comparing Clone #6 and Clone #14 transduced CBNK cells with mock transduced CBNK cells. Again, degranulation and IFN-γ expression was unexpectedly greater in the anti-Her2 CAR transduced CBNK cells compared with control cells in response to Her2+ target cells. Further, intracellular expression of TNF-α was unexpectedly greater in the anti-Her2 CAR transduced CBNK cells compared with Control cells in response to Her2+ target cells (FIG. 12A, FIG. 12B, FIG. 12C).

Figure 13:
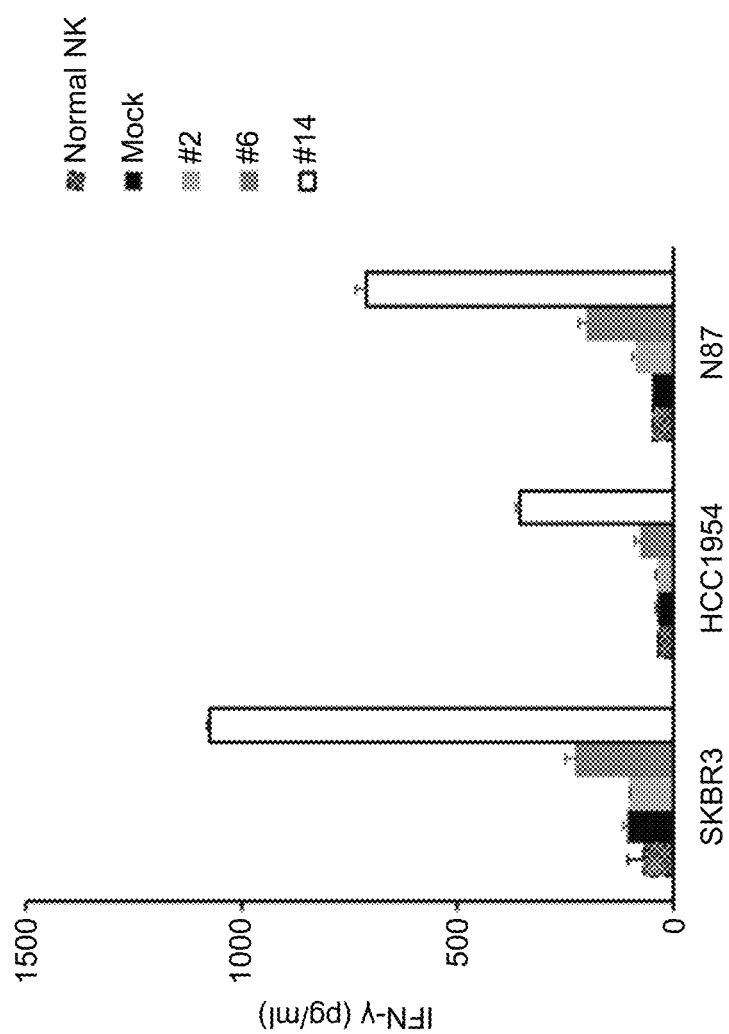
FIG. 13 is a bar graph showing the secretion of IFN-γ from anti-HER2-CAR-CBNKs (clones #2, #6, #14) when co-cultured with target cells.

IFN-γ Secretion: The secretion of IFN-γ from anti-HER2-CAR-CBNKs (clones #2, #6, #14) was compared by co-culturing with target cells. Cell culture supernatants from the 4 hr killing assay (FIG. 8A-8C) were assayed for secreted IFN-γ using an ELISA assay. CBNK cells expressing Clone #14 unexpectedly secreted significantly more IFN-γ when co-cultured with target cancer cells than all other clones and controls. Clone #6 consistently secreted more IFN-γ in response to target cancer cells in comparison with control cells and Clone #2 (FIG. 13).

Example 11: In Vivo Anti-Tumor Activity of Anti-Her2-CAR-NK Cells

Figure 14A:
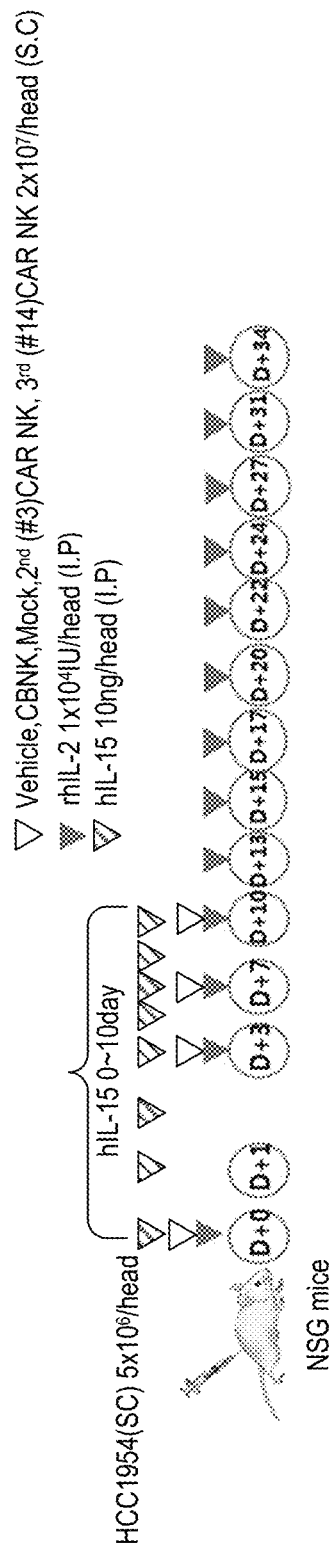
FIGS. 14A-14B are a scheme and line graph, respectively, showing the in vivo efficacy of anti-Her2-CAR clones #3 and #14 Xenograft models in NSG mice were generated by injecting $5 \times 10^6$ HCC1954 cells/mouse (HER-2 positive, trastuzumab resistant cells) subcutaneously. Tumor volume was assessed every 3-4 days after injection.
Figure 14B:
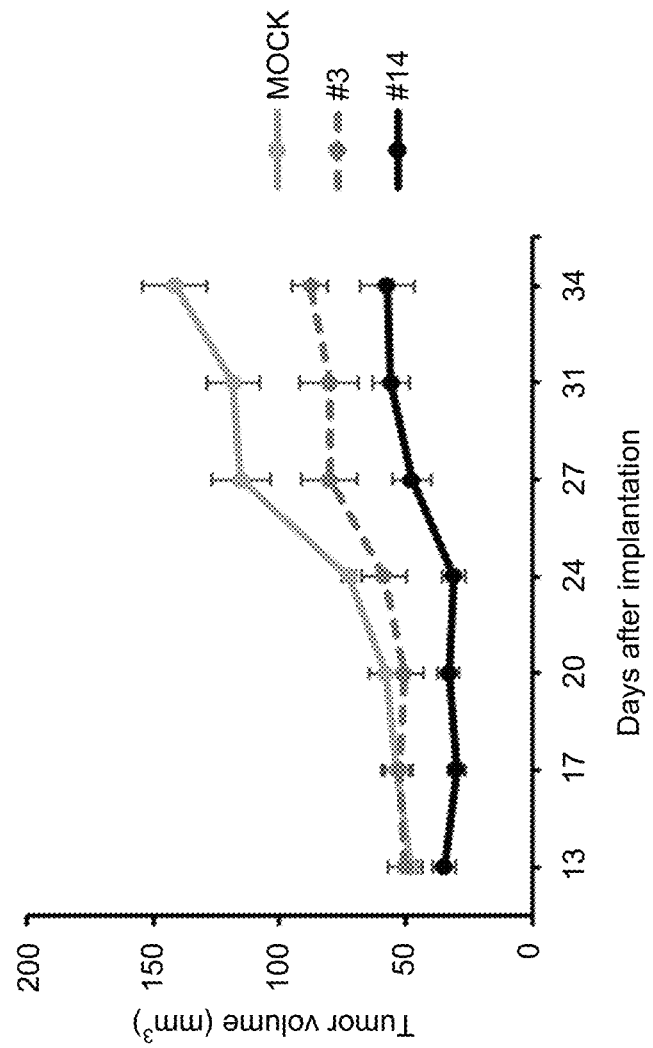

To evaluate in vivo efficacy of anti-Her2-CAR clones #3 and #14, Xenograft models in NSG mice were generated by injecting $5 \times 10^6$ HCC1954 cells/mouse (HER-2 positive, trastuzumab resistant cells) subcutaneously at Day 0. Subsequently, $2 \times 10^7$ cells of clone #3, #14, or mock-transduced CBNK were administered to the mice subcutaneously at day 0, 3, 7, 10. Additionally, Human IL-15 (10 ng/head) was intraperitoneally injected 8 times every 1-2 days up to day 10 and human IL-2 ($1 \times 10^4$ IU/head) was intraperitoneally injected 13 times every 2-4 days up to day 34. Tumor volume was assessed every 3-4 days after injection. Both clone #3 & #14 significantly suppressed tumor growth in mice on comparison with control, Mock-transduced CBNKs. Unexpectedly, clone #14 showed significantly better suppression of tumor growth than clone #3 (FIG. 14A and FIG. 14B).

Example 12: Culturing and Characterization of Anti-Her2-CAR-NK Cells

NK Cell Isolation From Umbilical Cord Blood or Peripheral Blood: CD3+ cells were removed by magnetic sorting system VarioMACS (Miltenyi Biotec, Germany) for NK cell enrichment from healthy donor derived UCB or PBMCs.

Generation of Feeder Cell Lines: HuT 78 cells were transduced with 4-1BBL, mTNF-α, or mbIL-21 in combination. The 4-1BBL insert was prepared from 4-1BB expressing vector (Origene, USA) by PCR. OX40L was synthesized from Bioneer (South Korea). mbIL-21 was synthesized with the sequence of IL-21 active protein, CD8 signal peptide, CD8 hinge, and CD8 transmembrane and further codon optimized. cDNA of mTNF-α was prepared by reverse transcription-polymerase chain reaction (RT-PCR) from PBMCs. TNF-α converting enzyme (TACE) recognition site mutation was introduced by replacing Ala-Val (A-V) with Pro-Val (P-V) by site directed mutagenesis kit (Agilent Technologies, USA). Inserted genes and lentiviral vectors (SBI, USA) were digested by EcoRI and BamHI (New England BioLabs, USA) and ligated by In-Fusion HD cloning kit (Clontech, USA). Lentiviral concentrate was produced in 293T by lipofectamine 2000 (Thermofisher Scientific, USA) and concentrated by Amicon Ultra-15 Centrifugal Filter Unit with Ultracel-100 membrane (Merckmillipore, USA). $0.5 \times 10^6$ cells/mL HuT 78 cells were suspended in 1 mL OPTU-MEM containing 50 uL lentiviral concentrate and 10 μg/mL polybrene (Santa Cruz Biotechnology, USA) and spinoculated at 1800 g, 320 for 90 minutes. HuT 78 cells transduced with lentiviral system were selected with antibiotics. 4-1BBL/mTNF-α mbIL-21 positive HuT 78 cells were isolated by flow cytometry-guided sorting (FACSMelody™ Cell Sorter, BD bioscience, USA).

Ex vivo Expansion and Cryopreservation of NK Cells: CD3+ depleted cells (1×10$^6$ cells/mL) were seeded in Cell-Gro SCGM medium (CellGenix, Germany) containing 1%-2% donor-plasma, 7-irradiated (2,000 rad) eHuT 78 (2.5×10$^6$ cells/mL) in CellGro SCGM medium containing 2% donor plasma, 1000 IU/mL IL-2 and 10 ng/mL anti-CD3 monoclonal antibody OKT3. Depending on culture duration, eHuT 78 cells were stimulated every 2 weeks. Cultured cells were fed with Cellgro SCGM containing 1% donor-plasma and 1000 IU/mL IL-2 (culture medium) to maintain cell concentration of 1-2×10$^6$ cells/mL for 14 days or 28 days. For cryopreservation of NK cells, harvested cells were suspended in freezing media and stored in a liquid nitrogen tank.

Immunostaining and Flow Cytometric Analysis: The following monoclonal antibodies were used to stain NK cells: anti-CD56-APC-eFluor®780 (CMSSB), and anti-CD62L-PE (DREG-56) (eBioscience, USA), anti-CD3-FITC (UCHT1), anti-CD14-FITC (M5E2) anti-CD16-PE (3G8), anti-DNAM-1-PE (DX11), anti-CD25-PE (M-A251), anti-CD44-PE (515), anti-CD56-PE-Cy5 (B159), anti-CXCR3-PE(1C6/CXCR3), anti-NKp30-PE (P30-15), anti-NKp44-PE (P44-8.1), anti-NKp46-PE (9E2/NKp46) antiOX40L-PE (ik-1), anti-4-1BBL-PE (C65-485), anti-4-1BB-PE (C65-485), anti-OX40-PE (ACT35), anti-CD27-PE (MT-271), anti-CD27L-PE (Ki-24), anti-CD30-PE (BerH8), anti-CD30L-PE, anti-CD3-PE-cy5.5 (SP34-2), anti-CD4-FITC (RPA-T4) (BD Biosciences, USA), anti-NKG2A-PE (131411), anti-NKG2C-PE (134591), anti-NKG2D-PE (149810), anti-TNF-α (membrane)-PE (6401) anti-TNF-α (membrane)-PE (6401), anti-TNFRII-PE (22235) (R&D systems, USA), anti-CD30L-PE (RM153) (Biolegend, USA). Live cells were gated with 7-AAD (Beckman-Coulter, USA). T cells and HuT 78 cells were stained with anti-TcRα/β-FITC (WT31), anti-CD2-PE (RPA-2.10), anti-CD7-FITC (4H9), anti-CD11a-FITC (G43-258), anti-CD25-PE (M-A251), anti-CD28-FITC (CD28.2), anti-CD44-PE (515) and anti-CD49d-PE (9F10) (BD Bioscience, USA). eHuT 78 cells were stained with anti-TNF-α (membrane)-PE (6401), (R&D systems, USA), antiOX40L-PE (ik-1), anti-4-1BBL-PE (C65-485) (BD bioscience, USA), and anti-IL21-PE (3A3-N2) (eBioscience, USA). Stained cells were acquired on LSR Fortessa and data were analyzed using FlowJo software (TreeStar Inc., OR).

Figure 15A:
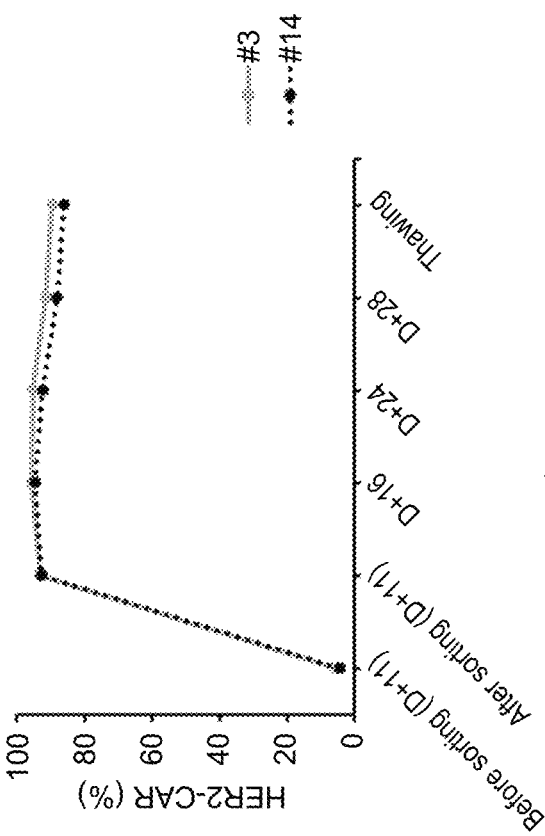
FIG. 15A is a line graph showing the proliferation of HER2-CAR-NK cells.

Comparison of Proliferation of HER2-CAR-NK Cells: The growth of CBNK cells, mock-transduced CBNK cells, or HER-2-CAR clones #6 and #14 was compared in culture for 28 days. During the culture period, cells were stimulated with irradiated feeder cells (eHut 78) twice at day 0 & day 14. Both clone #6 and #14 showed comparable growth pattern to unmodified and mock-transduced CBNKs (FIG. 15A).

Figure 15B:
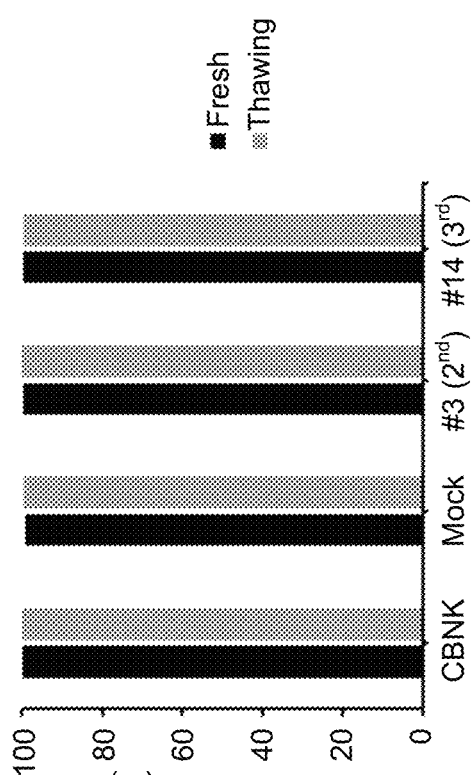
FIGS. 15B-15D are line graphs (FIG. 15B) and bar graphs (FIGS. 15C and 15D) showing the CAR expression levels, viability, and purity of HER2-CAR-NK cells during expansion, culture and cryopreservation.

Assessment of CAR Expression During Expansion, Culture, and Cryopreservation: To assess the CAR expression level in Lentiviral transduced CBNK cells, the HER-2 CAR population was analyzed by flow cytometry at day 11, day 16, day 24, day 28 and after freezing and thawing. Both clone #6 and #14 maintained more than 80% of CAR expression up to 28 day and through freezing and thawing (FIG. 15B).

Figure 15C:
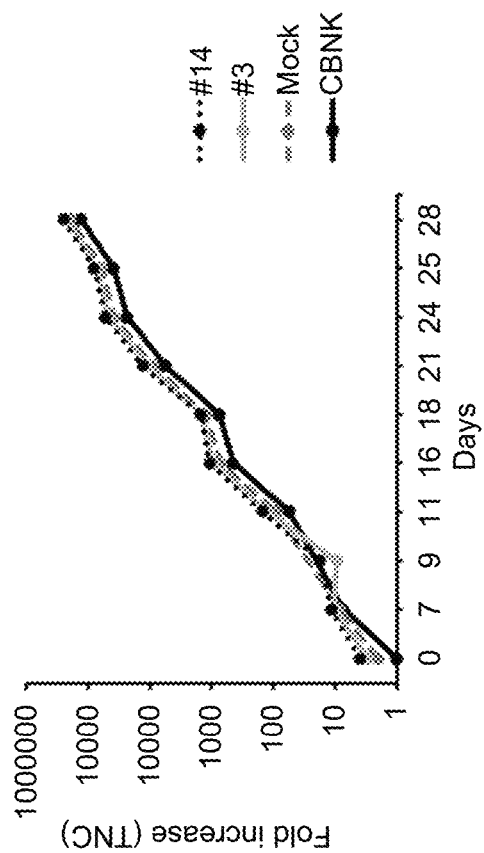
Figure 15D:
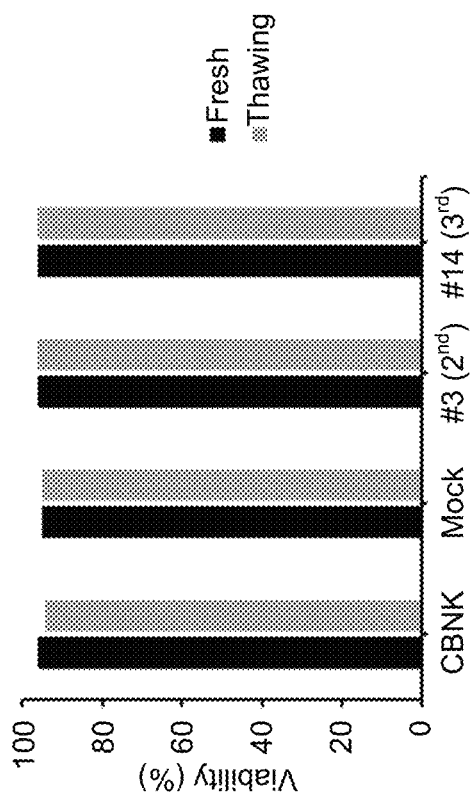

Viability of HER2-CAR-NK Cells During Expansion, Culture, and Cryopreservation: The cell viability for HER-2CAR-NK was analyzed after 28 day-culture and freezing and thawing using propidium iodide staining-based live cell counting. Both clone #6 and #14 showed more than 95% of cell viability and no viability changes were observed in the process of freezing and thawing at 28 days after culture (FIG. 15C and FIG. 15D).

Purity of HER2-CAR-NK Cells During Expansion Culture and Cryopreservation: The cell purity for HER-2CAR-NK was analysed after expansion culture and the freezing and thawing process using flow cytometry analysis. Counts for CD56+/CD3− cells were assessed. Both clone #6 and #14 maintained near 100% of CD56+/CD3− cell population at 28 days after culture and post the process of freezing and thawing process (FIG. 15D).

Figure 16:
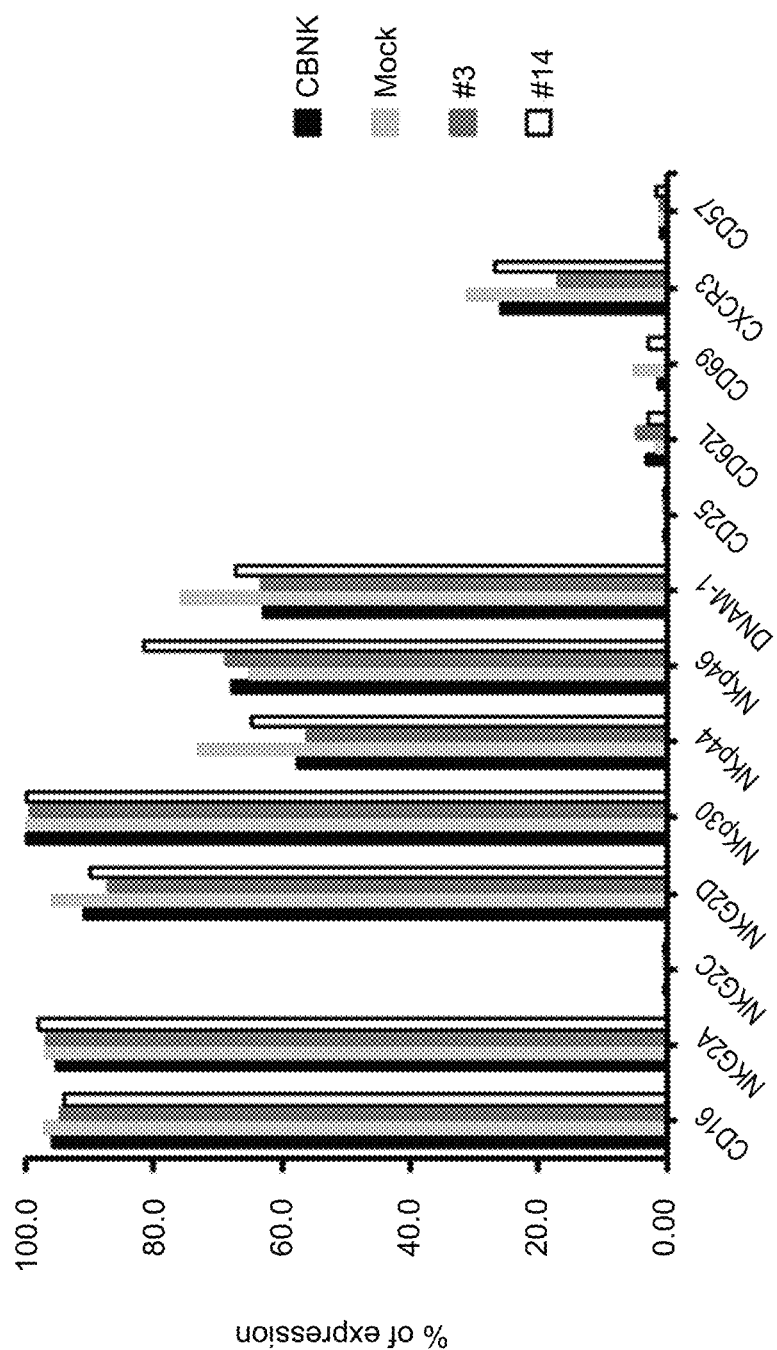
FIG. 16 is a bar graph showing the phenotypic cell surface marker expression of HER2-CAR-NK cells.

Phenotypic Cell Surface Marker Expression Analysis of HER2-CAR-NK Cells: The expression NK cell surface markers on unmodified, mock-transduced CBNK and clone #6 and #14 was assessed by flow cytometry analysis (CD16, NKG2A, NKG2C, NKG2D, NKp30, NKp44, NKp46, CD25, CD62L, CD69, CXCR3, CD57). The expression levels of all markers tested in both HER2-CAR-NK cells expressing clones #6 and #14 were comparable to those of control NK cells (FIG. 16).

What is claimed is:

1. A chimeric antigen receptor targeting human HER2, the chimeric antigen receptor comprising an amino acid sequence comprising:
   an extracellular antigen binding domain comprising a heavy chain variable region comprising the amino acid sequences of SEQ ID NO: 7, SEQ ID NO: 8, and SEQ ID NO: 9, and a light chain variable region comprising the amino acid sequences of SEQ ID NO: 10, SEQ ID NO: 11, and SEQ ID NO: 12;
   a hinge domain;
   a transmembrane domain; and
   an intracellular signaling domain comprising an OX40L intracellular signaling domain.

2. The chimeric antigen receptor of claim 1, wherein the OX40L intracellular signaling domain comprises an amino acid sequence having at least 90% sequence identity with SEQ ID NO: 127.

3. The chimeric antigen receptor of claim 2, wherein the OX40L intracellular signaling domain comprises the amino acid sequence of SEQ ID NO: 127.

4. The chimeric antigen receptor of claim 1, wherein the intracellular signaling domain further comprises a CD3z intracellular signaling domain.

5. The chimeric antigen receptor of claim 4, wherein the CD3z intracellular signaling domain comprises an amino acid sequence having at least 90% sequence identity with SEQ ID NO: 121.

6. The chimeric antigen receptor of claim 5, wherein the CD3z intracellular signaling domain comprises the amino acid sequence of SEQ ID NO: 121.

7. The chimeric antigen receptor of claim 1, wherein the intracellular signaling domain further comprises a CD28 intracellular signaling domain.

8. The chimeric antigen receptor of claim 7, wherein the CD28 intracellular signaling domain comprises an amino acid sequence having at least 90% sequence identity with SEQ ID NO: 125.

9. The chimeric antigen receptor of claim 8, wherein the CD28 intracellular signaling domain comprises the amino acid sequence of SEQ ID NO: 125.

10. The chimeric antigen receptor of claim 1, wherein the intracellular signaling domain further comprises a CD3z intracellular signaling domain and a CD28 intracellular signaling domain.

11. The chimeric antigen receptor of claim 10, wherein the OX40L intracellular signaling domain comprises an amino acid sequence having at least 90% sequence identity with SEQ ID NO: 127, the CD3z intracellular signaling domain comprises an amino acid sequence having at least 90% sequence identity with SEQ ID NO: 121, and the CD28 intracellular signaling domain comprises an amino acid sequence having at least 90% sequence identity with SEQ ID NO: 125.

12. The chimeric antigen receptor of claim 11, wherein the OX40L intracellular signaling domain comprises an amino acid sequence having the amino acid sequence of SEQ ID NO: 127, the CD3z intracellular signaling domain comprises an amino acid sequence having the amino acid sequence of SEQ ID NO: 121, and the CD28 intracellular signaling domain comprises an amino acid sequence having the amino acid sequence of SEQ ID NO: 125.

13. The chimeric antigen receptor of claim 1, wherein the hinge domain is a CD8a hinge domain and the transmembrane domain is a CD28 transmembrane domain.

14. The chimeric antigen receptor of claim 12, wherein the hinge domain is a CD8a hinge domain and the transmembrane domain is a CD28 transmembrane domain.

15. A nucleic acid encoding the chimeric antigen receptor of claim 1.

16. A vector comprising the nucleic acid of claim 15.

17. A cell expressing the chimeric antigen receptor of claim 1.

18. The cell of claim 17, wherein the cell is an immune cell.

19. The cell of claim 18, wherein the cell is a natural killer cell.

20. A method of treating a HER2 positive cancer, the method comprising: administering to a subject in need thereof the cell of claim 19.

* * * * *